United States Patent
Jose et al.

(10) Patent No.: US 10,285,702 B2
(45) Date of Patent: May 14, 2019

(54) BIORESORBABLE BIOPOLYMER ANASTOMOSIS DEVICES

(71) Applicants: Trustees of Tufts College, Medford, MA (US); Beth Israel Deaconess Medical Center, Inc., Boston, MA (US)

(72) Inventors: Rodrigo R. Jose, Medford, MA (US); Waseem K. Raja, Medford, MA (US); David L. Kaplan, Concord, MA (US); Ahmed Ibrahim, Brookline, MA (US); Samuel Lin, Dover, MA (US); Abdurrahman Abdurrob, Winchester, MA (US)

(73) Assignees: Trustees of Tufts College, Medford, MA (US); Beth Israel Deaconess Medical Center, Inc., Boston, MA (US)

( * ) Notice: Subject to any disclaimer, the term of this patent is extended or adjusted under 35 U.S.C. 154(b) by 307 days.

(21) Appl. No.: 14/785,047

(22) PCT Filed: Apr. 24, 2014

(86) PCT No.: PCT/US2014/035361
§ 371 (c)(1),
(2) Date: Oct. 16, 2015

(87) PCT Pub. No.: WO2014/176458
PCT Pub. Date: Oct. 30, 2014

(65) Prior Publication Data
US 2016/0095599 A1 Apr. 7, 2016

Related U.S. Application Data

(60) Provisional application No. 61/815,551, filed on Apr. 24, 2013.

(51) Int. Cl.
*A61B 17/11* (2006.01)
*A61L 27/50* (2006.01)
*A61B 17/00* (2006.01)

(52) U.S. Cl.
CPC ..... *A61B 17/11* (2013.01); *A61B 2017/00004* (2013.01); *A61B 2017/00526* (2013.01);
(Continued)

(58) Field of Classification Search
CPC .......... A61B 17/11; A61B 2017/00004; A61B 2017/00778; A61B 2017/00858;
(Continued)

(56) References Cited

U.S. PATENT DOCUMENTS 4,657,019 A * 4/1987 Walsh .................... A61B 17/11
606/153
4,693,249 A * 9/1987 Schenck ................ A61B 17/11
606/153
(Continued)

FOREIGN PATENT DOCUMENTS

WO WO-97/08315 A1 3/1997
WO WO-2004/000915 A2 12/2003
(Continued)

OTHER PUBLICATIONS

U.S. Appl. No. 61/791,501, filed Mar. 15, 2013, Kaplan.
(Continued)

Primary Examiner — Ryan J. Severson
(74) Attorney, Agent, or Firm — Quarles & Brady LLP

(57) ABSTRACT

A bioresorbable drug-eluting biopolymer suture-free blood vessel anastomosis devices can be deployed to join two blood vessels and resorbed by the body over a predetermined time period after the blood vessel has become joined. The anastomosis device can include a hollow tube that is inserted interconnect the two vessels to be jointed. A non-
(Continued)

piercing suture is wrapped around the vessel to secure the anastomosis. The anastomosis device can include hollow tube that extends along an axis from a first end to a second end. The ends can be fitted with elements that facilitate mechanical attachment of the vessel to the anastomosis device and provide for a secure seal.

20 Claims, 21 Drawing Sheets

(52) U.S. Cl.
CPC .............. *A61B 2017/00778* (2013.01); *A61B 2017/00858* (2013.01); *A61B 2017/00893* (2013.01); *A61B 2017/1107* (2013.01); *A61B 2017/1132* (2013.01); *A61L 27/502* (2013.01); *A61L 27/507* (2013.01)

(58) Field of Classification Search
CPC ..... A61B 2017/1107; A61B 2017/1132; A61F 2/064; A61F 2/848; A61F 2002/8483; A61F 2002/8486; A61L 27/3604; A61L 27/502; A61L 27/507
See application file for complete search history.

(56) References Cited

U.S. PATENT DOCUMENTS

| | | | |
|---|---|---|---|
| 4,806,355 A | 2/1989 | Goosen et al. | |
| 4,917,087 A * | 4/1990 | Walsh | A61B 17/11 606/153 |
| 4,931,057 A | 6/1990 | Cummings et al. | |
| 5,015,476 A | 5/1991 | Cochrum et al. | |
| 5,093,489 A | 3/1992 | Diamantoglou | |
| 5,245,012 A | 9/1993 | Lombari et al. | |
| 5,263,992 A | 11/1993 | Guire | |
| 5,270,419 A | 12/1993 | Domb | |
| 5,576,881 A | 11/1996 | Doerr et al. | |
| 5,902,800 A | 5/1999 | Green et al. | |
| 5,932,462 A | 8/1999 | Harris et al. | |
| 6,030,395 A * | 2/2000 | Nash | A61B 17/11 606/153 |
| 6,036,705 A * | 3/2000 | Nash | A61B 17/11 606/153 |
| 6,056,762 A * | 5/2000 | Nash | A61B 17/11 606/153 |
| 6,127,143 A | 10/2000 | Gunasekaran | |
| 6,245,537 B1 | 6/2001 | Williams et al. | |
| 6,267,776 B1 | 7/2001 | O'Connell | |
| 6,302,848 B1 | 10/2001 | Larson et al. | |
| 6,310,188 B1 | 10/2001 | Mukherjee | |
| 6,325,810 B1 | 12/2001 | Hamilton et al. | |
| 6,337,198 B1 | 1/2002 | Levene et al. | |
| 6,372,244 B1 | 4/2002 | Antanavich et al. | |
| 6,379,690 B2 | 4/2002 | Blanchard et al. | |
| 6,387,413 B1 | 5/2002 | Miyata et al. | |
| 6,395,734 B1 | 5/2002 | Tang et al. | |
| 6,402,767 B1 * | 6/2002 | Nash | A61B 17/11 606/153 |
| 6,666,873 B1 | 12/2003 | Cassell | |
| 7,842,780 B2 | 11/2010 | Kaplan et al. | |
| 8,142,454 B2 * | 3/2012 | Harrison | A61B 17/0483 606/153 |
| 8,187,616 B2 * | 5/2012 | Wang | A61K 9/5089 424/400 |
| 8,992,594 B2 * | 3/2015 | Soletti | A61B 17/11 623/1.13 |
| 9,504,575 B2 * | 11/2016 | Kaplan | A61F 2/2846 |
| 9,517,357 B2 * | 12/2016 | Omenetto | A61F 7/03 |
| 9,554,989 B2 * | 1/2017 | Kaplan | A61K 9/0019 |
| 2008/0009902 A1 | 1/2008 | Hunter et al. | |
| 2010/0028451 A1 | 2/2010 | Kaplan et al. | |
| 2010/0178304 A1 | 7/2010 | Wang et al. | |
| 2010/0279112 A1 | 11/2010 | Kaplan et al. | |
| 2011/0046686 A1 | 2/2011 | Kaplan et al. | |
| 2011/0171239 A1 | 7/2011 | Kaplan et al. | |
| 2012/0271405 A1 | 10/2012 | Soletti et al. | |
| 2013/0310908 A1 * | 11/2013 | Omenetto | A61F 7/03 607/114 |
| 2015/0045764 A1 | 2/2015 | Kaplan et al. | |
| 2015/0165092 A1 | 6/2015 | Kaplan et al. | |
| 2015/0183841 A1 * | 7/2015 | Lo | A61L 27/56 424/402 |
| 2015/0283298 A1 | 10/2015 | Kaplan et al. | |
| 2016/0095599 A1 * | 4/2016 | Jose | A61B 17/11 606/154 |

FOREIGN PATENT DOCUMENTS

| | | |
|---|---|---|
| WO | WO-2004/062697 A2 | 7/2004 |
| WO | WO-2005/012606 A2 | 2/2005 |
| WO | WO-2007/098951 A2 | 9/2007 |
| WO | WO-2008/118133 A2 | 10/2008 |
| WO | WO-2008/150861 A1 | 12/2008 |
| WO | WO-2009/023615 A1 | 2/2009 |
| WO | WO-2009/126689 A2 | 10/2009 |
| WO | WO-2011/005381 A2 | 1/2011 |
| WO | WO-2011/041395 A2 | 4/2011 |
| WO | WO-2013/142119 A1 | 9/2013 |
| WO | WO-2013/152265 A1 | 10/2013 |

OTHER PUBLICATIONS

Aarnio, P. et al., Vascular Clips in Anastomoses of Femoropopliteal Arterial Reconstruction, Int. J. Angiol., 9(2):62-64 (2000).
Abou Taam, S. et al., Experimental study of a novel mechanical connector for sutureless open arterial anastomosis, J. Vasc. Surg., 55(1):210-5 (2012).
Acharya, C. et al., Performance evaluation of a silk protein-based matrix for the enzymatic conversion of tyrosine to $_L$-DOPA, Biotechnol. J., 3:226-233 (2008).
Alghoul, M.S. et al., From simple interrupted to complex spiral: a systematic review of various suture techniques for microvascular anastomoses, Microsurgery, 31(1):72-80 (2011).
Altman, G.H. et al., Silk-based biomaterials, Biomaterials, 24:401-416 (2003).
Ameli, F.M. et al., Etiology and management of aorto-femoral bypass graft failure, J. Cardiovasc. Surg. (Torino), 28(6):695-700 (1987).
Baynosa, R.C. et al., Use of a novel penetrating, sutureless anastomotic device in arterial microvascular anastomoses, J. Reconstr. Microsurg., 24(1):39-42 (2008).
Bayraktar, O. et al., Silk fibroin as a novel coating material for controlled release of theophylline, European Journal of Pharmaceutics and Biopharmaceutics, 60:373-381 (2005).
Beris, A.E. et al., Digit and hand replantation, Arch. Orthop. Trauma Surg., 130(9):1141-7 (2010).
Bigdeli, A.K. et al., Interrupted nitinol U-Clips versus standard running suture for the central arterial T-graft anastomosis: a prospective randomized study, Eur. J. Cardiothorac. Surg., 40(2):e93-7 (2011).
Braughman, C. et al., Heparin stimulates elastogenesis: application to silk-based vascular grafts, Matrix Biol., 30(5-6):346-55 (2011).
Bui, D.T. et al., Free flap reexploration: indications, treatment, and outcomes in 1193 free flaps, Plast. Reconstr. Surg., 119(7):2092-100 (2007).
Camici, G.G., What is an optimal stent? Biological requirements of drug eluting stents, Kardiovaskulare Medizin, 11:22-5 (2008).
Chang, E.I. et al., Vascular anastomosis using controlled phase transitions in poloxamer gels, Nat. Med., 17(9):1147-52 (2011).
Charlson, M.E. and Isom, O.W., Clinical practice. Care after coronary-artery bypass surgery, N. Engl. J. Med., 348(15):1456-63 (2003).
Cho, A.B. et al., Fibrin glue application in microvascular anastomosis: comparative study of two free flaps series, Microsurgery, 29(1):24-8 (2009).

(56) References Cited

OTHER PUBLICATIONS

Colon Surgery Anastomosis Animation. Video [online]. NiTi Surgical Solutions. 2007 [retrieved on Sep. 9, 2014]. Retrieved from the internet: <URL: https://www.youtube.com/watch?v=sF2OmfpekCE>.
Demura, M. and Asakura, T., Immobilization of glucose oxidase with Bombyx mori silk fibroin by only stretching treatment and its application to glucose sensor, Biotechnol. Bioeng., 33(5):598-603 (1989).
Dibra, A. et al., Influence of stent surface topography on the outcomes of patients undergoing coronary stenting: a randomized double-blind controlled trial, Catheter. Cardiovasc. Interv., 65(3):374-80 (2005).
Dijke et al., Growth Factors for Wound Healing, Bio/Technology, 7:793-798 (1989).
Disa, J.J. et al., Efficacy of conventional monitoring techniques in free tissue transfer: an 11-year experience in 750 consecutive cases, Plast. Reconstr. Surg., 104(1):97-101 (1999).
Ducic, I. et al., Lower extremity free flap reconstruction outcomes using venous coupler, Microsurgery, 31(5):360-4 (2011).
Erbel, R. et al., Progress-AMS (Clinical Performance and Angiographic Results of Coronary Stenting with Absorbable Metal Stents) Investigators. Temporary scaffolding of coronary arteries with bioabsorbable magnesium stents: a prospective, non-randomised multicentre trial, Lancet, 369(9576):1869-75 (2007).
Erdmann, D. et al., Side-to-side sutureless vascular anastomosis with magnets, J. Vasc. Surg., 40(3):505-11 (2004).
Farooq, V. et al., Short-term and long-term clinical impact of stent thrombosis and graft occlusion in the SYNTAX trial at 5 years: Synergy Between Percutaneous Coronary Intervention with Taxus and Cardiac Surgery trial, J. Am. Coll. Cardiol., 62(25):2360-9 (2013).
French, B.N. and Rewcastle, N.B., Recurrent stenosis at site of carotid endarterectomy, Stroke, 8(5):597-605 (1977).
Goldstein, B.H. et al., Percutaneous balloon-expandable covered stent implantation for treatment of traumatic aortic injury in children and adolescents, Am. J. Cardiol., 110(10):1541-5 (2012).
Gonzalez, I. et al., Medium and long-term outcomes after bilateral pulmonary artery stenting in children and adults with congenital heart disease, Pediatr. Cardiol., 34(1):179-84 (2013).
Gonzalo, N. and Macaya, C., Absorbable stent: focus on clinical applications and benefits, Vasc. Health Risk Manag., 8:125-32 (2012).
Habara, S. et al., Core 6. Catheter-Based and Surgical Interventions, Session Title: Periprocedural Complications in PCI, Abstract 14109: Impact of Diabetes Mellitus on Angiographic Outcomes in Patients With Different Drug-Eluting Stents, Circulation, 124:A14109, 1 page (2011) retrieved from the internet on Feb. 25, 2016: <http://circ.ahajournals.org/content/124/Suppl_21/A14109.abstract?sid=89d8ae24-8355-4b55-9da5-54cb7618f82d>.
Hamilos, M. et al., Interference of drug-eluting stents with endothelium-dependent coronary vasomotion: evidence for device-specific responses, Circ. Cardiovasc. Interv., 1(3)193-200 (2008).
Hersel, U. et al., RGD modified polymers: biomaterials for stimulated cell adhesion and beyond, Biomaterials, 24(24):4385-415 (2003).
Hofmann, S., et al., Silk fibroin as an organic polymer for controlled drug delivery, Journal of Controlled Release, 111:219-227 (2006).
Hu, X. et al., Regulation of Silk Material Structure by Temperature-Controlled Water Vapor Annealing, Biomacromolecules, 12:1686-1696 (2011).
Huang, F. et al., In vitro and in vivo characterization of a silk fibroin-coated polyester vascular prosthesis, Artif. Organs., 32(12):932-41 (2008).
International Search Report for PCT/US2014/035361, 4 pages (dated Oct. 3, 2014).
Jamshidi, R. et al., Magnamosis: magnetic compression anastomosis with comparison to suture and staple techniques, J. Pediatr. Surg., 44(1):222-8 (2009).
Jin, I.J. et al., Water-Stable Silk Films with Reduced Beta-Sheet Content, Adv. Funct. Mater., 15:1241-1247 (2005).
Lawrence, B.D. et al., Effect of hydration on silk film material properties, Macromol. Biosci., 10(4):393-403 (2010).
Li, M. et al., Study on Porous Silk Fibroin Materials. II. Preparation and Characteristics of Spongy Porous Silk Fibroin Materials, Journal of Applied Polymer Science, 79:2192-2199 (2001).
Linneweber, J. et al., The effect of surface roughness on activation of the coagulation system and platelet adhesion in rotary blood pumps, Artif. Organs, 31(5):345-51 (2007).
Liu, L. et al., Experimental study of one-shot vascular anastomostic device for proximal vein graft anastomoses, Ann. Thorac. Surg., 82(1):303-6 (2006).
Lovett, M. et al., Gel spinning of silk tubes for tissue engineering, Biomaterials, 29(35):4650-4657 (2008).
Lovett, M. et al., Silk fibroin microtubes for blood vessel engineering, Biomaterials, 28:5271-5279 (2007).
Lu, Q. et al., Stabilization and release of enzymes from silk films, Macromol. Biosci., 10(4):359-68 (2010).
Lu, S. et al., Insoluble and flexible silk films containing glycerol, Biomacromolecules, 11(1):143-50 (2010).
Lu, S. et al., Stabilization of Enzymes in Silk Films, Biomacromolecules, 10:1032-1042 (2009).
Lucas, F. et al., The silk fibroins, Advances in Protein Chemistry, 13:107-242 (1958).
Mandal, B. et al., High-strength silk protein scaffolds for bone repair, Proceedings of the National Academy of Sciences USA, 109(20):7699-7704 (2012).
Meinel, L. et al., The inflammatory responses to silk films in vitro and in vivo, Biomaterials, 26(2):147-155 (2005).
Mickley, V., Stenosis and thrombosis in haemodialysis fistulae and grafts: the surgeon's point of view, Nephrol. Dial. Transplant., 19(2):309-11 (2004).
Min, S. et al., Preparation and Characterization of Crosslinked Porous Silk Fibroin Gel, Sen'I Gakkaishi, 54(2):85-92 (1997).
Miyairi, S. and Sugiura, M., Properties of β-Glucosidase Immobilized in Sericin Membrane, Journal of Fermentation Technology, 56(4):303-308 (1978).
Motwani, J.G. and Topol, E.J., Aortocoronary saphenous vein graft disease: pathogenesis, predisposition, and prevention, Circulation, 97(9):916-31 (1998).
Murphy, A. and Kaplan, D., Biomedical applications of chemically-modified silk fibroin, Journal of Materials Chemistry, 19(36):6443-6450 (2009).
Murphy, A.R. et al., Modification of Silk Fibroin Using Diazonium Coupling Chemistry and the Effects on hMSC Proliferation and Differentiation, Biomaterials, 29(19):2829-2838 (2008).
Nazarov, R. et al., Porous 3-D scaffolds from regenerated silk fibroin, Biomacromolecules, 5(3):718-26 (2004).
NIHR HSC. Bioresorbable stents for occlusive coronary artery disease. Birmingham: NIHR Horizon Scanning Centre (NIHR HSC). Horizon Scanning Review (2012).
Nishio, S. et al., Long-Term (>10 Years) clinical outcomes of first-in-human biodegradable poly-1-lactic acid coronary stents: Igaki-Tamai stents, Circulation, 125(19):2343-52 (2012).
Ojha, M. et al., Histology and morphology of 59 internal thoracic artery grafts and their distal anastomoses, Ann. Thorac. Surg., 70(4):1338-44 (2000).
Ormiston, J.A. and Serruys, P.W., Bioabsorbable coronary stents, Circ. Cardiovasc. Interv., 2(3):255-60 (2009).
Palmerini, T. et al., Stent thrombosis with drug-eluting and bare-metal stents: evidence from a comprehensive network meta-analysis, Lancet, 379(9824):1393-402 (2012).
Panilaitis, B. et al., Macrophage responses to silk, Biomaterials, 24(18):3079-85 (2003).
Pratt, G.F. et al., Technology-assisted and sutureless microvascular anastomoses: evidence for current techniques, Microsurgery, 32(1):68-76 (2012).
Pritchard, E. et al., Silk fibroin encapsulated powder reservoirs for sustained release of adenosine, Journal of Controlled Release, 144(2):159-167 (2010).
Ramcharitar, S. and Serruys, P.W., Fully biodegradable coronary stents : progress to date, Am. J. Cardiovasc. Drugs, 8(5):305-14 (2008).

(56) References Cited

OTHER PUBLICATIONS

Rockwood, D.N. et al., Materials Fabrication from *Bombyx mori* Silk Fibroin, Nature Protocols 6(10):1612-1631 (2011).
Schaffner P. and Dard, M.M., Structure and function of RGD peptides involved in bone biology, Cell Mol Life Sci., 60:119-32 (2003).
Schwartz, S.M. et al., The intima. Soil for atherosclerosis and restenosis, Circ. Res., 77(3):445-65 (1995), retrieved online on Feb. 18, 2016 <http://circres.ahajournals.org/content/77/3/445.full>.
Sofia, S. et al., Functionalized silk-based biomaterials for bone formation, Journal of Biomedical Materials Research, 54(1): 139-148 (2001).
Stick, C. et al., Venous pressure in the saphenous vein near the ankle during changes in posture and exercise at different ambient temperatures, Eur. J. Appl. Physiol. Occup. Physiol., 66(5):434-8 (1993).
Takahashi, K. et al., Induction of Pluripotent Stem Cells form Adult Human Fibroblasts by Defined Factors, Cell 131:861-872 (2007).
Taylor, J. et al., Use of the U-clip for microvascular anastomosis, Microsurgery, 26(8):550-1 (2006).
Ueda, K. et al. Bioabsorbable device for small-caliber vessel anastomosis, Microsurgery, 30(6):494-501 (2010).
Van Der Giessen, W.J. et al., Marked inflammatory sequelae to implantation of biodegradable and nonbiodegradable polymers in porcine coronary arteries, Circulation, 94(7):1690-7 (1996) retrieved from the internet on Feb. 19, 2016 <http://circ.ahajournals.org/content/94/7/1690.long>.
Vasic, N. et al., Long-term graft occlusion in aortobifemoral position, Vojnosanit Pregl., 70(8):740-6 (2013).
Vepari, C. and Kaplan, D.L., Silk as a Biomaterial, Prog. Polym. Sci., 32(8-9): 991-1007 (2007).
Von Schroeder, H.P. et al., The changes in intramuscular pressure and femoral vein flow with continuous passive motion, pneumatic compressive stockings, and leg manipulations, Clin. Orthop. Relat. Res., (266):218-26 (1991).
Wall, J. et al., Magnamosis IV: magnetic compression anastomosis for minimally invasive colorectal surgery, Endoscopy, 45(8):643-8 (2013).
Wang, X. et al., Controlled release from multilayer silk biomaterial coatings to modulate vascular cell responses, Biomaterials, 29(7):894-903 (2008).
Wang, X. et al., Growth factor gradients via microsphere delivery in biopolymer scaffolds for osteochondral tissue engineering, J. Control. Release., 134(2):81-90 (2009).
Wang, X. et al., Silk microspheres for encapsulation and controlled release, Journal of Controlled Release, 117(3):360-370 (2007).
Wenk, et al., Silk Fibroin Spheres as a Platform for Controlled Drug Delivery, Journal of Controlled Release, 132(1):26-34 (2008).
Wiklund, L. et al., A new mechanical connector for distal coronary artery anastomoses in coronary artery bypass grafting: a randomized, controlled study, J. Thorac. Cardiovasc. Surg., 129(1):146-50 (2005).
Wong, M.M. et al., Sirolimus stimulates vascular stem/progenitor cell migration and differentiation into smooth muscle cells via epidermal growth factor receptor/extracellular signal-regulated kinase/beta-catenin signaling pathway, Arterioscler. Thromb. Vasc. Biol., 33(10):2397-2406 (2013).
Written Opinion for PCT/US2014/035361, 14 pages (dated Oct. 3, 2014).
Ye, G. et al., Arterial anastomosis without sutures using ring pin stapler for clinical renal transplantation: comparison with suture anastomosis, J. Urol., 175(2):636-40 (2006).
Yu, J. et al., Induced Pluripotent Stem Cell Lines Derived from Human Somatic Cells, Science 318:1917-1920 (2007).
Zeebregts, C.J. et al., Five years' world experience with nonpenetrating clips for vascular anastomoses, Am. J. Surg., 187(6):751-60 (2004).
Zeebregts, C.J. et al., Randomized clinical trial of continuous sutures or non-penetrating clips for radiocephalic arteriovenous fistula, Br. J. Surg., 91(11):1438-42 (2004).
Zhang, W. et al., the use of injectable sonication-induced silk hydrogel for VEGF(165) and BMP-2 delivery for elevation of the maxillary sinus floor, Biomaterials, 32(35):9415-24 (2011).
Zhang, X. et al., Dynamic culture conditions to generate silk-based tissue-engineered vascular grafts, Biomaterials, 30(19):3213-23 (2009).
Zilberman, M. et al., Mechanical properties and in vitro degradation of bioresorbable fibers and expandable fiber-based stents, J. Biomed. Mater. Res. B Appl. Biomater., 74(2):792-9 (2005).
Zubilewicz, T. et al., Injury in vascular surgery—the intimal hyperplastic response, Med. Sci. Monit., 7(2):316-24 (2001).

\* cited by examiner

Figures 13A-F a) Newtons

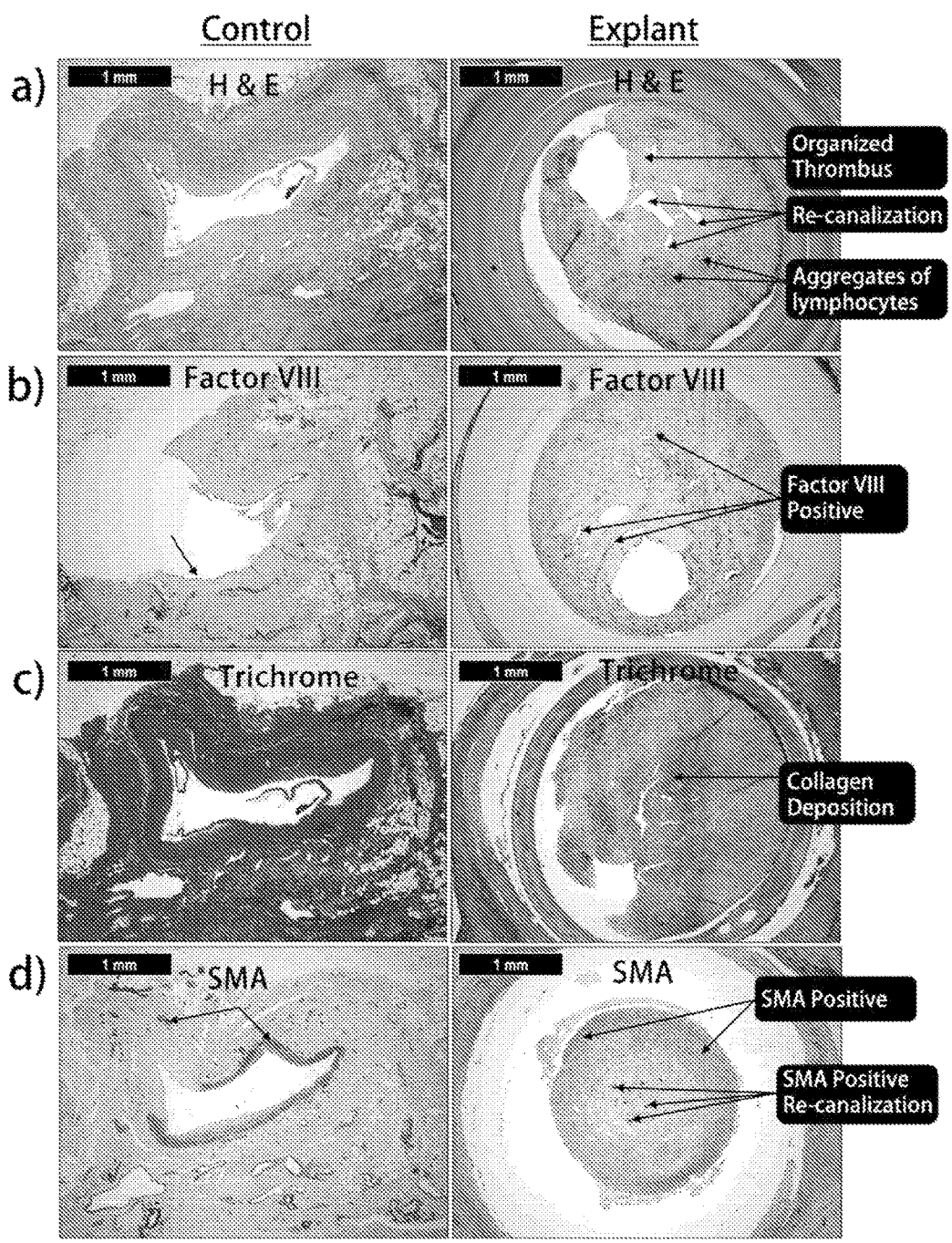
Figures 20A-D

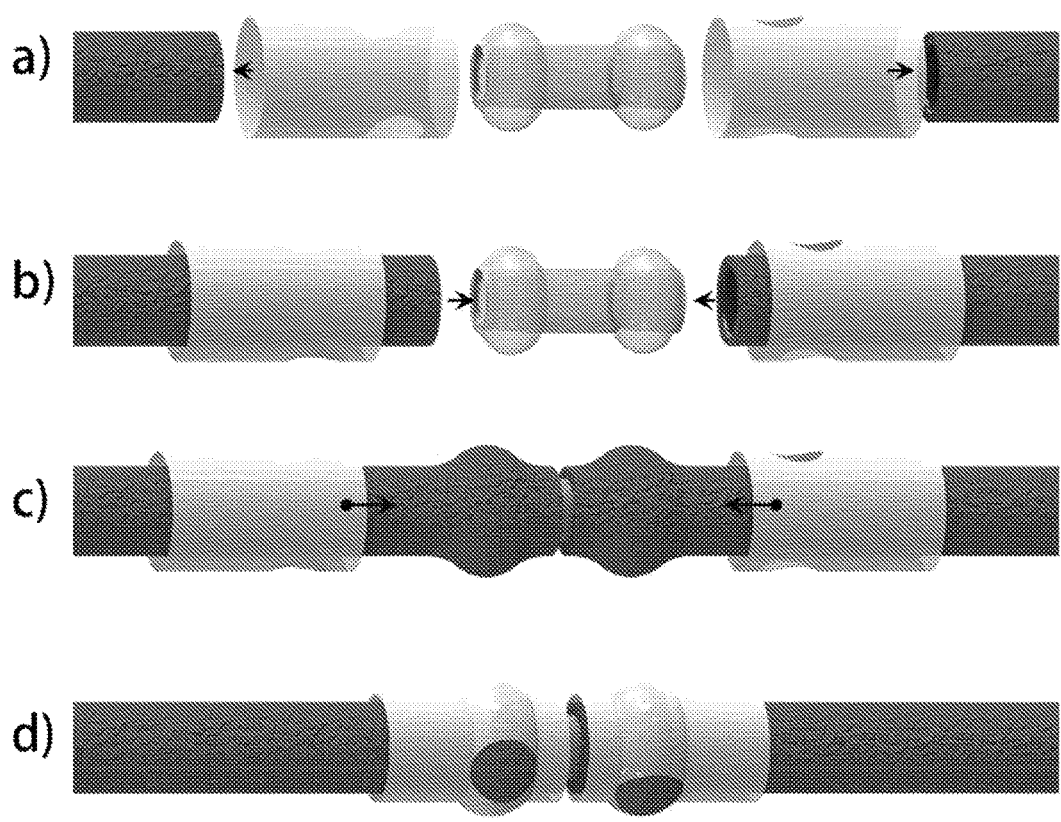
Figures 21 A-D

BIORESORBABLE BIOPOLYMER ANASTOMOSIS DEVICES

CROSS-REFERENCE TO RELATED APPLICATIONS

The present application claims the benefit of priority to U.S. Provisional Patent Application Ser. No. 61/815,551, filed Apr. 24, 2013, the entire contents of which are incorporated herein by reference.

STATEMENT REGARDING FEDERALLY SPONSORED RESEARCH

This invention was made with government support under grant EB002520 and 3 P41 EB002520-09S1 awarded by the National Institutes of Health. The government has certain rights in the invention.

BACKGROUND

Technical Field

The invention relates to bioresorbable drug-eluting biopolymer suture-free blood vessel anastomosis devices and methods and systems for facilitating vascular anastomosis. Specifically, the invention is directed to devices that can facilitate vascular anastomosis by providing a quick mechanical union without the need for suturing or tying knots. The bioresorbable biopolymer can include silk fibroin, e.g., silk fibroin and blend that includes silk fibroin, e.g., silk fibroin materials.

Description of Certain Art

Manual suturing is the standard as a technique that necessitates precise placement of sutures in the wall of blood vessels to approximate their ends [4-7]. Current microsurgical suturing techniques involve using fine (8-0 to 12-0) monofilament nylon sutures mounted on sharp round needles. Vessels are prepared under a microscope; vessels may be placed on a double approximating clamp so that the ends can be approximated under no tension [16,22].

Vessel couplers can enable the anastomosis of small diameter vessels in cardiothoracic, vascular, and transplant surgery as well as for microsurgical reconstructive procedures in plastic surgery. Manual suturing requires extreme technical precision to prevent long-term failure from foreign body reaction to the suture material and intimal hyperplasia [4-7]. These factors and others have contributed to persistent failure rates in 2-6% of cases [8,9]. Sutured anastomosis may be unreliable in small (<1.0 mm) or diseased vessels with a tendency to fracture and develop clot, as a contraindication to neovascularization. Furthermore, vascular grafts continue to undergo thrombosis resulting in vascular occlusion, prolonged hospital stays and death [10-15]. Even in experienced hands, microvascular anastomosis remains a challenging and time consuming procedure and has a steep learning curve for any surgeon in training. Reconstitution of blood supply via vessel anastomosis is technically challenging and requires expertise in meticulous microsuturing technique. Technical suturing errors such as uneven spacing, inversion of suture walls, and misalignment of the vessel intima can lead to anastomotic leaks and thrombosis which can be disastrous. For these reasons, alternatives to traditional sutured microvascular anastomosis have been actively investigated [16]. Different devices such as microclips, staples or magnets have been used in an attempt to overcome the technical difficulties of sutures (most of them have been designed for large-caliber vessels greater than 2 mm in diameter) but have been found to be traumatic to blood vessels resulting in failure rates comparable to or higher than those of sutured anastomosis [17-21]. Sutureless vascular anastomosis is a technique gaining interest for decreasing operative time and complexity [21].

SUMMARY

The present invention provides methods and systems that utilize bioresorbable drug-eluting biopolymer materials to construct suture-free blood vessel anastomosis devices. The devices according to various embodiments of the invention can facilitate vascular anastomosis by providing a quick mechanical union without the need for suturing or tying knots and by providing grafting material to span distances which would otherwise prevent direct coaptation of the vessel segments. The biopolymer blend can be non-injuring to the vessel lumen yet is able to maintain patency while prevent kinking or twisting of the vessel. Disclosed embodiments can be grouped into several different anastomosis device families, which vary by anastomosis mechanism. These embodiments complement each other and provide options for a broader range of vessel joining applications. Each of the anastomosis mechanisms according to the invention can provide different sets of application specific benefits at varying levels of cost to security, drug elution, or implantation speed. Although the mechanical assemblies are structurally different, the design components can be fabricated using the same bulk material, for example, silk fibroin and blends including silk fibroin materials.

Aastomosis devices according to various embodiments of the invention can provide complete restorability, complex drug elution, and highly tunable mechanical properties by using polymer materials. These polymer based implants benefit from their extensive use in tissue engineering. Unlike metallic counterparts, polymer materials have been developed as scaffolds with control, manipulation, and tailoring cellular processes and integration. In addition, resorbable materials can be used to enable sutureless anastomosis devices according to some embodiments of the invention be resorbed by the body over time.

Degradation of resorbable magnesium alloys progresses as pronounced surface pitting inhibits endothelialization [23] which limits use as implant material [24]. Additionally, alloys are limited to a thin polymer matrix for drug delivery [25]. Rather than the simple corrosion degradation of magnesium implants, silk fibroin:glycerol blends can facilitate controllable tissue integration and implant resorption/degradation. Poly-L-lactic acid which degrades by bulk erosion via hydrolysis of bonds between repeating lactide units [26,27] has been shown to suffer from shrinkage after vascular implantation in vivo [23]. Tyrosine-derived polycarbonate, which metabolizes to amino acids, ethanol, and carbon dioxide [23] produced major adverse vascular events in vivo, such as, myocardial infarction [23]. Poly(anhydride ester) salicylic acid [28] releases salicylic acid as bonds are hydrolyzed during surface erosion absorption [23], but has produced intimal hyperplasia and restenosis in vivo [23]. Additionally, polyglycolic acid/polylactic acid, polycaprolactone, polyhydroxybutyrate/valerate, polyorthoester, and polyethylencoxide/polybutylene terephthalate have induced inflammatory reactions and fibrocellular proliferation within 2.5- to 3.0-mm diameter coronary arteries [29].

In contrast to these polymers, silk fibroin has been reported to be less immunogenic and inflammatory and has been reported to be used successfully in small diameter blood vessels in a number of animal studies [30-32]. Unlike the tyrosine-derived polycarbonate, salicylate, and magnesium alloys, our silk fibroin material swells slightly after hydrated, in physiological conditions [33]. This property of silk fibroin improves vessel fitment and makes them more secure, in contrast to the shrinking observed with polylactic acid implants [23]. Our design and material have been developed after surveying the advancements and limitations of competitive approaches. Our device is uniquely suited to minimize implant induced injury and promote vascular healing. The polymer implant has high radial strength yet is compliant at the tissue interface. The silk fibroin-based system prevents vessel stenosis at the site of anastomosis and delivers sophisticated drug treatments enabling complete resorption and healthy vessel remodeling. The micropermeable material allows nutrient exchange but will not allow erosion of the vessel wall eliminating hyperplasia driven restenosis. Silk fibroin Biomaterial Systems The flexibility of silk fibroin processing allows for the formation of silk fibroin films and other more complex composite materials [34].

Slow Degradation—Silk fibroin biomaterials degrade to amino acids slowly over the course of weeks to years [31], without chemical or photoinitiated crosslinking, unlike collagens and many other polymeric biomaterials.

Biocompatibility—Silk fibroins have been used as sutures for decades (FDA approved) are biocompatible and are less immunogenic and inflammatory than other common degradable polymers (collagens or polyesters such as PLGA) [32,35]. There are no known bioburdens in silk fibroins, unlike persistent concerns with collagens [36]. Silk fibroin medical devices have recently expanded into new applications based on FDA approval (Serica, Inc., recently purchased by Allergan, Inc.).

Mechanical Properties and Sterilization—Silk fibroins offer robust mechanical properties in many formats [36,37]. These materials can also be autoclaved for sterilization without loss of mechanical integrity [36].

Functionalization—Proteins can be adsorbed to silk fibroin, or chemically linked. For example, silk fibroin matrices can be functionalized with cell growth factors and peptides with direct control over placement and density of these factors using nontoxic and biocompatible chemistries [38-40].

Stabilization and Controlled Release of Therapeutics In Silk fibroin—The bioresorbable silk fibroin can deliver greater drug payloads and more complex drug release over longer time periods thereby limiting the occurrence of localized restenosis throughout the process of implant resorption [41,42]. Polarized drug elution can provide more control of endothelial stimulation and inhibition of smooth muscle. Enzymes, antibiotics, vaccines and antibodies can be entrapped in silk fibroin protein biomaterials, resulting in remarkable stabilization even at relatively high temperatures and without specialized storage conditions [43-45]. For example, stabilization of antibiotics and enzymes for months or up to one year at 37° C. underscores the versatility and potential of this technology. We have also demonstrated that various therapeutics to regulate vascular cell responses can be incorporated into silk fibroin materials and in turn, regulate endothelial and vascular cell outcomes [331,46,47]. In addition silk fibroin materials can control the release profile of many biological samples including proteins [43, 45,48,49].

Chronic Interfacial Injury—We can fine tune the stiffness of the material to match natural vessels. Each film will exhibit time dependent reductions in stiffness throughout the degradation in vivo. In particular, this enables us to pinpoint the optimal implant mechanical stiffness which is time-dependent with respect to endothelialization and prevention of adventitial angiogenic hyperplasia. The optimal mechanical properties will reduce proliferative thickening and inflammation, subsequently reducing vessel healing time. This will in turn reduce the required implant mechanical radial strength, which would have been needed to combat the implant induced restenosis at later time points, and ultimately allow for implant resorption and degradation of mechanical function.

These and other capabilities of the invention, along with the invention itself, will be more fully understood after a review of the following figures, detailed description, and claims.

BRIEF DESCRIPTION OF THE DRAWING

The Drawing included herein is comprised of the following several Figures:

FIGS. 20 (A-D) (a) H & E staining of the occlusion developed within the device (b) Factor VIII demonstrate the recanalization is lined with endothelial cells (c) Trichrome staining reveal collagen has been deposited within the occlusion (d) Cells within the occlusion and recanalization are positive for smooth muscle actin suggesting smooth muscle hyperplasia.

FIGS. 21 (A-D) Schematic of components and method of anastomosis.

DETAILED DESCRIPTION OF PREFERRED EMBODIMENTS

The present invention is directed to biorsorbable biopolymer suture-free blood vessel anastomosis devices and methods for their use. In some embodiments, such anastomosis devices are also capable of releasing therapeutics, anti-coagulants, or other active agents. In accordance with various embodiments of the invention, anastomosis devices can provide vascular anastomosis using a mechanical union without the need for suturing or tying knots. In accordance with various embodiments of the invention, anastomosis devices can span distances which would otherwise prevent direct coaptation of the vessel segments.

Exemplary Devices

Figure 1:
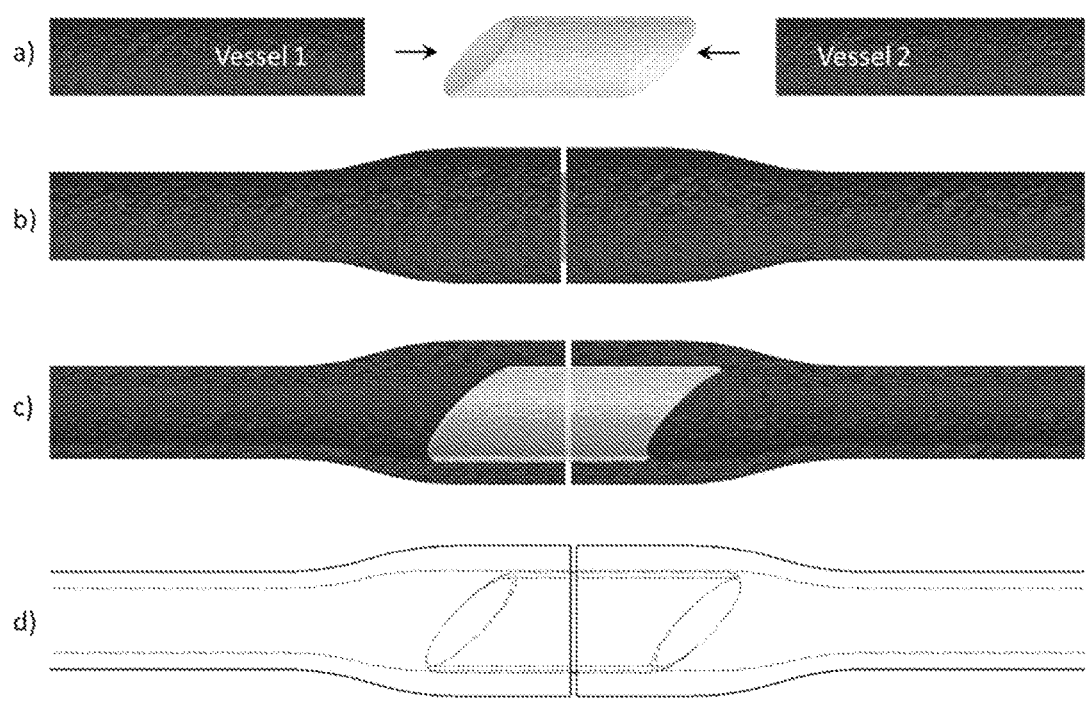
FIG. 1 shows a polymer anastomosis device according to a first embodiment of the invention.

FIG. 1 shows an anastomosis device 100 according to some embodiments of the invention. In this embodiment, the anastomosis device 100 includes a hollow tube 110 formed of a polymeric material that extends along a longitudinal axis from a first end 112 to a second end 114 and each end can be pressed into the lumen of opposing vessel segments a shown in FIGS. 1b, 1c and 1d. The one or both ends 112, 114 can be cut 90° to the longitudinal axis or can include a non-piercing 45° beveled tip to facilitate implantation. A non-piercing suture 120 can be wrapped around the vessel to secure the anastomosis device at one or both ends. The suture can be fabricated by coating fine-drawn dextrose rods with HFIP solubilized silk fibroin. This embodiment of the invention can used to join vessel segments that have very small diameters. For example, this embodiment can be used in lymphatics or micro-channeling where 100 to 500 μm lumen vessels are to be joined. In accordance with some embodiments of the invention, the wall thickness of the hollow tube can be in the range from 50 to 150 μm. Upon removal of clamps and restoration of blood flow, blood passes from the proximal vessel segment through the lumen of the implanted hollow tube then into the distal vessel segment. Blood flow contacts the luminal surface of the anastomosis device which can be coated or bulk loaded with a variety of established vascular antithrombotic, anti-proliferative, or antibiotic drugs. This embodiment of the invention can be implanted very quickly and can facilitate anastomosis in small diameter vessels, for example, in the range from 100 to 500 μm. This embodiment can also be used where the vessel segment length is very limited and in application where it is desirable to span short vessel segment gaps to serve dual functions, as a grafting material as well as performing anastomosis. In some embodiments, the device 100 of FIG. 1 is prepared from a bulk material that is 100% silk and is derived by solubilizing the protein in HFIP, for example as described herein.

Figure 2:
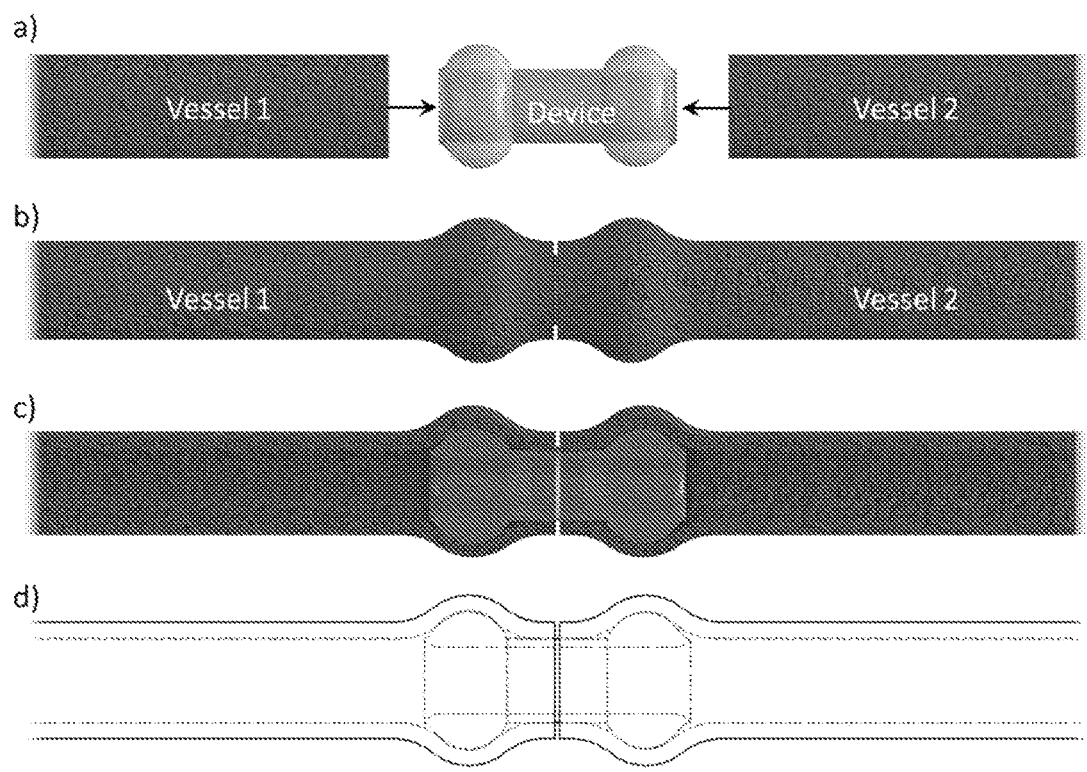
FIG. 2 shows a polymer anastomosis device according to a second embodiment of the invention.

FIG. 2 shows an anastomosis device 200 according to some embodiments of the invention. In this embodiment, the anastomosis device 200 includes a hollow tube 210 formed of a polymeric material that extends along a longitudinal axis from a first cod 212 to a second end 214 and each end can be pressed into the lumen of opposing vessel segments as shown in FIGS. 2b, 2c and 2d. One or both ends 212, 214 can include spherical barbs or bulges which can be pressed into the lumen of opposing vessel segments. In accordance with some embodiments of the invention, the diameter of the spherical barbs can be in the range of 110% to 140% of the vessel inner diameter, for example, approximately 125% of the vessel inner diameter in order to provide increased frictional retaining forces on the outside surface of the anastomosis device. Each end of the device can include a rounded tip 212, 214 which can aid in sealing and securing the anastomosis device without inducing chronic injury at the implant/tissue interface. After the spherical tips have been inserted, a non-piercing suture 220 can be wrapped around each vessel to secure the vessel to the anastomosis device 200. For example, this embodiment can be used where 500 to 5000 μm lumen vessels are to be joined. In accordance with some embodiments of the invention, the wall thickness of the hollow tube 210 can be in the range from 100 to 250 μm. Upon removal of clamps and restoration of blood flow, blood passes from the proximal vessel segment through the lumen of the implanted hollow tube then into the distal vessel segment. Blood flow contacts the luminal surface of the anastomosis device which can be coated or bulk loaded which a variety of established vascular antithrombotic, anti-proliferative, or antibiotic drugs. This embodiment of the invention can be implanted very quickly and can facilitate anastomosis where vessel segment length is very limited. Where necessary, the anastomosis devices according to this embodiment can span short vessel segment gaps to serve dual functions as a grafting material as well as performing anastomosis. This embodiment of the invention can provide improved connection security over that of the device shown in FIG. 1. In some particular embodiments, the device 200 of FIG. 2 is prepared from a bulk material that comprises or consists of a silk:glycerol blend in a dry weight ratio of 75:25, for example fabricated as described herein.

Figure 3:
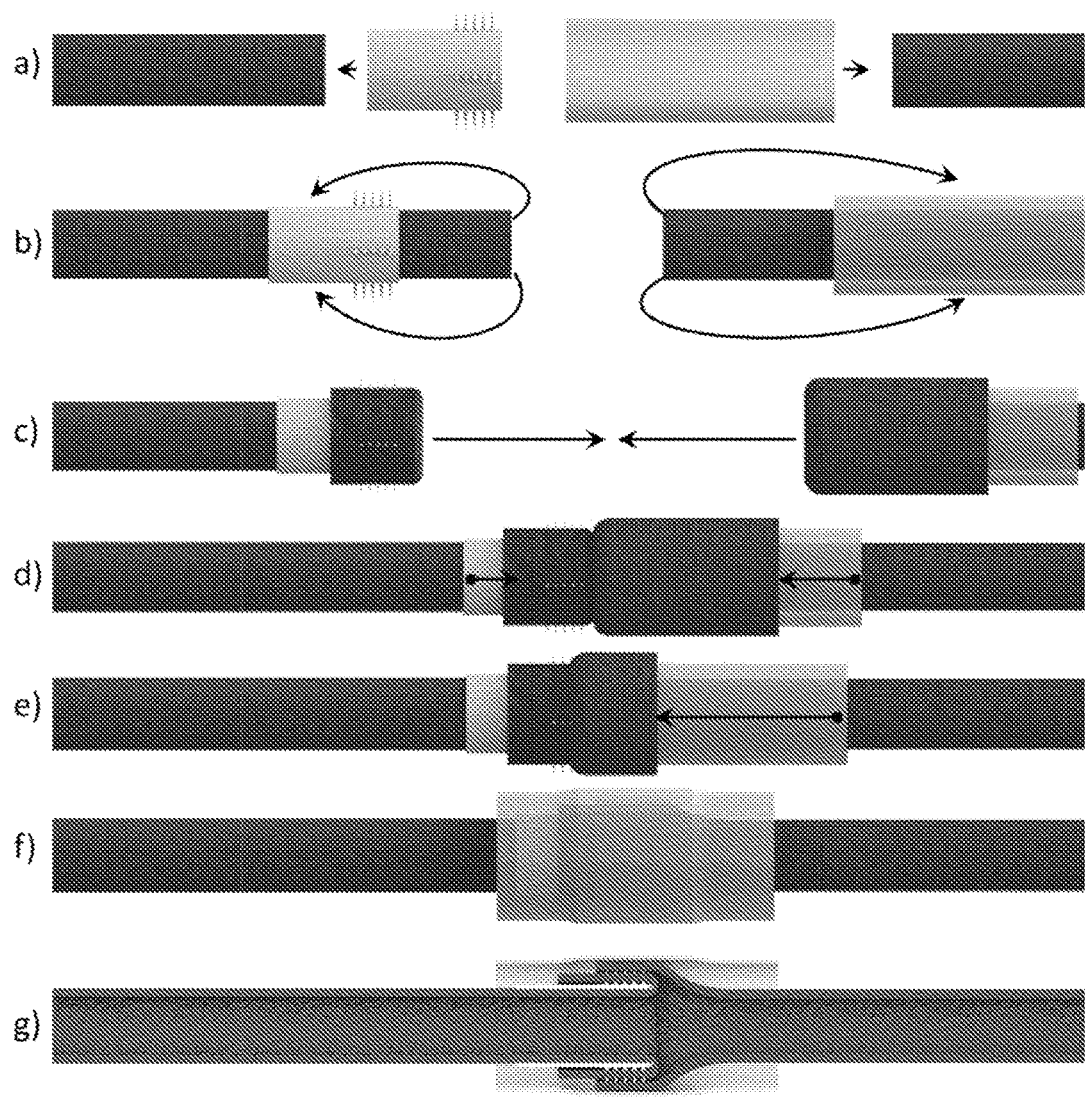
FIG. 3 shows a polymer anastomosis device according to a third embodiment of the invention.

FIG. 3 shows an anastomosis device 300 according to some embodiments of the invention. In this embodiment, the anastomosis device 300 includes a first tube 310 formed of a polymeric material that extends along a longitudinal axis and has one or more circumferential rows of microneedles 312 protruding radially outward at one or more locations along tube 310 and a second tube 314 formed of a polymeric material. The length and diameter of the microneedles 312 can be determined by the characteristics of the vessel walls, including, for example, the vessel wall thickness. In accordance with some embodiments of the invention, the preferred microneedle 312 length can be approximately 180% of the vessel wall thickness. In accordance with some embodiments of the invention, the wall thickness of the first tube 310 can be in the range from 100 µm to 400 µm and in some embodiments, approximately 250 rpm. In some particular embodiments, the device 300 of FIG. 3 is prepared from a bulk material that comprises or consists of a silk:glycerol blend in a dry weight ration of 75:25, for example fabricated as described herein.

Figure 4:
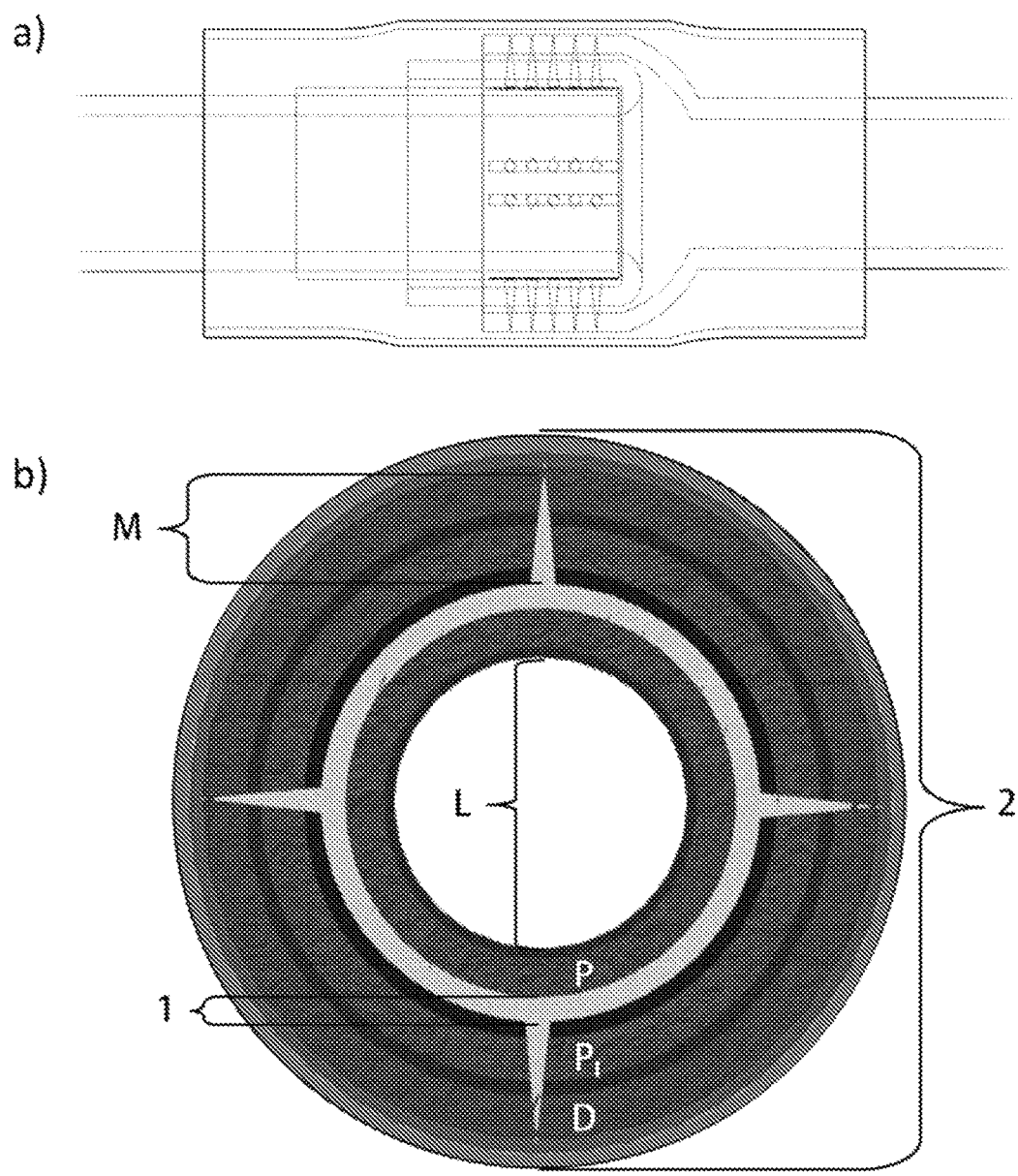
FIG. 4 shows a cross-sectioned view of the polymer anastomosis device shown in FIG. 3.

FIG. 4 shows a cross-section of the anastomosis device shown in FIG. 3. In accordance with some embodiments, the second tube 314 can be configured with an inner diameter that enables it to be positioned over the first tube 310 and the array of microneedles 312 as well as one or more layers of vessel wall. In accordance with some embodiments of the invention, the second tube 314 can have an inner diameter equivalent to the outer diameter of the first tube 310 (e.g., L+P+P+1+1), plus the height, M, of the microneedles 314. In accordance with some embodiments of the invention, the wall thickness of the second tube 310 can be in the range from 100 µm to 200 µm and in some embodiments, approximately 150 µm.

FIGS. 3a-3g show an anastomosis procedure according to some embodiments of the invention. In accordance with the invention, the first tube 310 can be slid around the proximal vessel segment, vessel 1, and the second tube 314 can be slid around the distal vessel segment, vessel 2 as shown in FIG. 3a. Next, the proximal vessel, vessel 1 can be inverted around the first tube 310, and the distal vessel, vessel 2 can be inverted around second tube 314 as shown in FIG. 3b. The inverted vessel segment ends can be brought together concentrically as shown in FIG. 3c. While supporting the first tube 310 and the inverted proximal segment of the proximal vessel, vessel 1 steady, the second tube 314 can be slide over the first tube 310 and the microneedles 312, which will unroll the inverted portion of the distal vessel segment over the first tube 310 and the microneedles 312 as shown in FIGS. 3d and 3e. The microneedles 312 can pierce and fix the vessels in place and the assembly can be maintained by compression fitting the second tube 314 over the first tube 310, completing anastomosis as shown in FIGS. 3f and 3g. The proximal segment remains inverted around Part 1, exposing the inner surface of the proximal segment of vessel 1 in direct contact with inner surface of the distal vessel segment, vessel 1 and also concentrically wraps the first tube 310. As shown in FIG. 4, the microneedles 312 of the first tube 310 can penetrate through both vessel walls.

Upon removal of clamps and restoration of blood flow, blood passes from the proximal vessel segment directly to the lumen of the distal vessel segment. Blood flow contacts only the endothelial surfaces of blood vessels and does not contact the anastomosis device, which nearly eliminates thrombotic risk. In accordance with this embodiment of the invention, the device 300 including the microneedles 312 can be coated or bulk loaded with a variety of established vascular antithrombotic, anti-proliferative, or antibiotic drugs. The anastomosis devices according to this embodiment of the invention can be used where vessels having a lumen diameter of approximately 2500 µm or greater are to be joined. In addition, this embodiment of the invention can be used in pairs in conjunction with vascular grafting materials and procedures. Where necessary, devices according to this embodiment can span short vessel segment gaps to serve dual function as a grafting material as well as performing anastomosis. The anastomosis produced according to this embodiment of the invention can be very secure. The implantation speed of the anastomosis device according to this embodiment of the invention can be in the range from 1 to 7 minutes.

Figure 5:
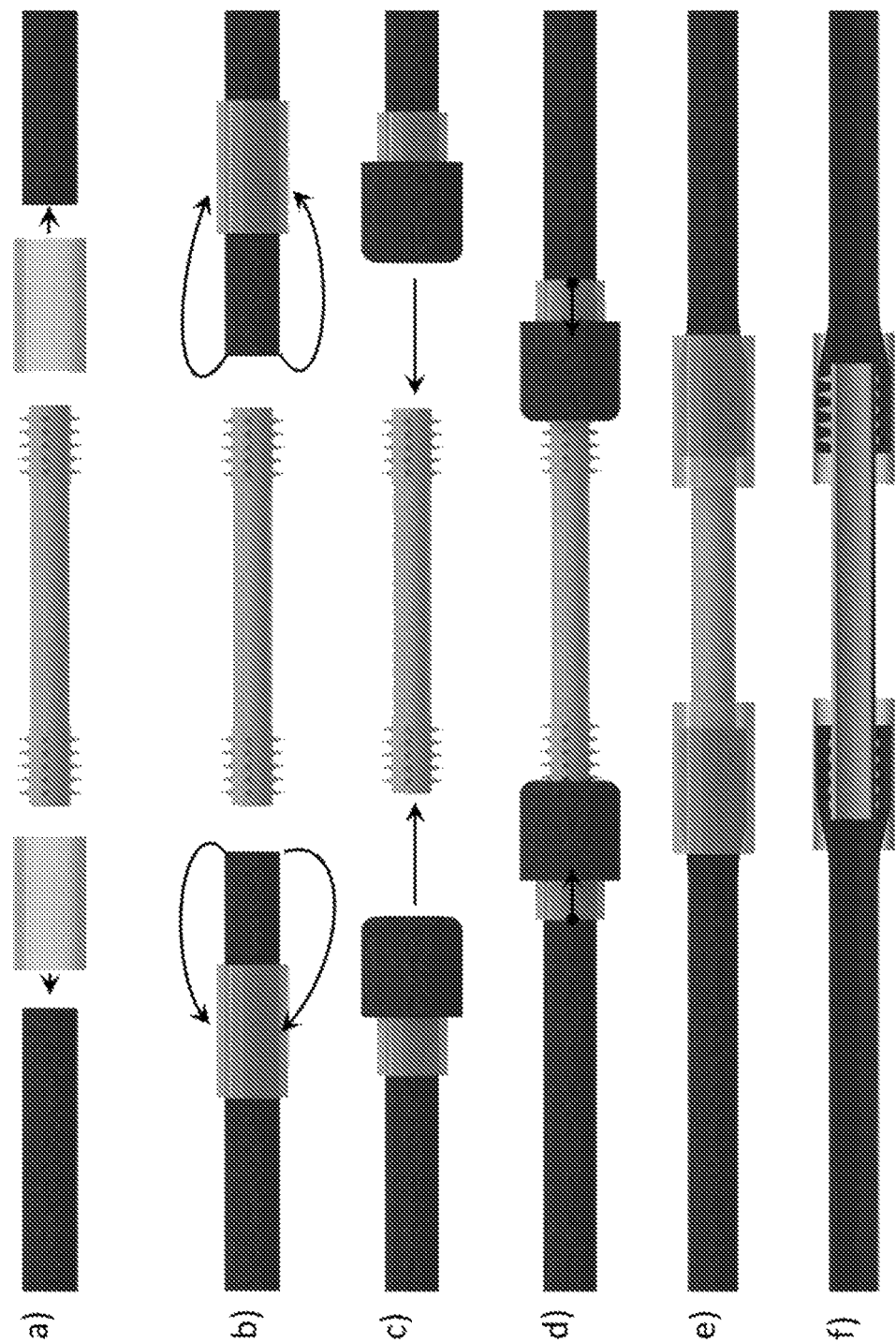
FIG. 5 shows a polymer anastomosis device according to a fourth embodiment of the invention.

FIG. 5 shows an anastomosis device 500 according to some embodiments of the invention. In this embodiment, the anastomosis device 500 includes a first tube 510 formed of a polymeric material that extends along a longitudinal axis from a first end 512 to a second end 514 and has one or more circumferential rows of microneedles 512A, protruding radially outward at the first end 512 and microneedles 514A, protruding radially outward at the second end 514, a second tube 514 formed of a polymeric material and a third tube 516 formed of a polymeric material. In some particular embodiments, the device 500 of FIG. 5 is prepared from a bulk material that comprises or consists of a silk:glycerol blend in a dry weight ration of 75:25, for example fabricated as described herein.

FIG. 5 also shows an anastomosis procedure according to some embodiments of the invention. In accordance with the invention, the second tube 516 can be slid around the proximal vessel segment, vessel 1, and the third tube 518 can be slid around the distal vessel segment as shown in FIG. 5a. Next, the proximal vessel, vessel 1 can be inverted around second tube 516, and the distal vessel, vessel 2 can be inverted around third tube 518 as shown in FIG. 5b. The inverted vessel segment ends can be brought together concentrically at each end 512 and 514 of the first tube 310 as shown in FIG. 5c. While holding the first tube 510 steady, the second tube 516 can slid over the first end 512, which will unroll the inverted proximal vessel segment over the microneedles 512A at the first end 512 of the first tube 510 as shown in FIGS. 5d-5e. Similarly, the third tube 518 can slid over the second end 514, which will unroll the inverted distal vessel segment over the microneedles 514A at the second end 514 of the first tube 510 as shown in FIGS. 5d-5c. The microneedles 512A and 514A can pierce and fix the vessels in place and the assembly can be maintained by compression fitting the second tube 516 over the first end 512 and the third tube 518 over the second end 514, completing anastomosis as shown in FIGS. 5e-5f.

Upon removal of clamps and restoration of blood flow, blood passes from the proximal vessel segment through the lumen of the first tube 510 then into the distal vessel segment. Blood flow contacts the luminal surface of the anastomosis device 500 which can be coated or bulk loaded with a variety of established vascular antithrombotic, antiproliferative, or antibiotic drugs. Where necessary, devices according to this embodiment can span short vessel segment gaps to serve dual function as grafting material as well as performing anastomosis. The anastomosis devices according to this embodiment of the invention can be used where vessels having a lumen diameter of approximately 2500 µm or greater are to be joined. The anastomosis produced according to this embodiment of the invention can be very secure. The implantation speed of the anastomosis device according to this embodiment of the invention can be in the range from 2 to 9 minutes.

Figure 6:
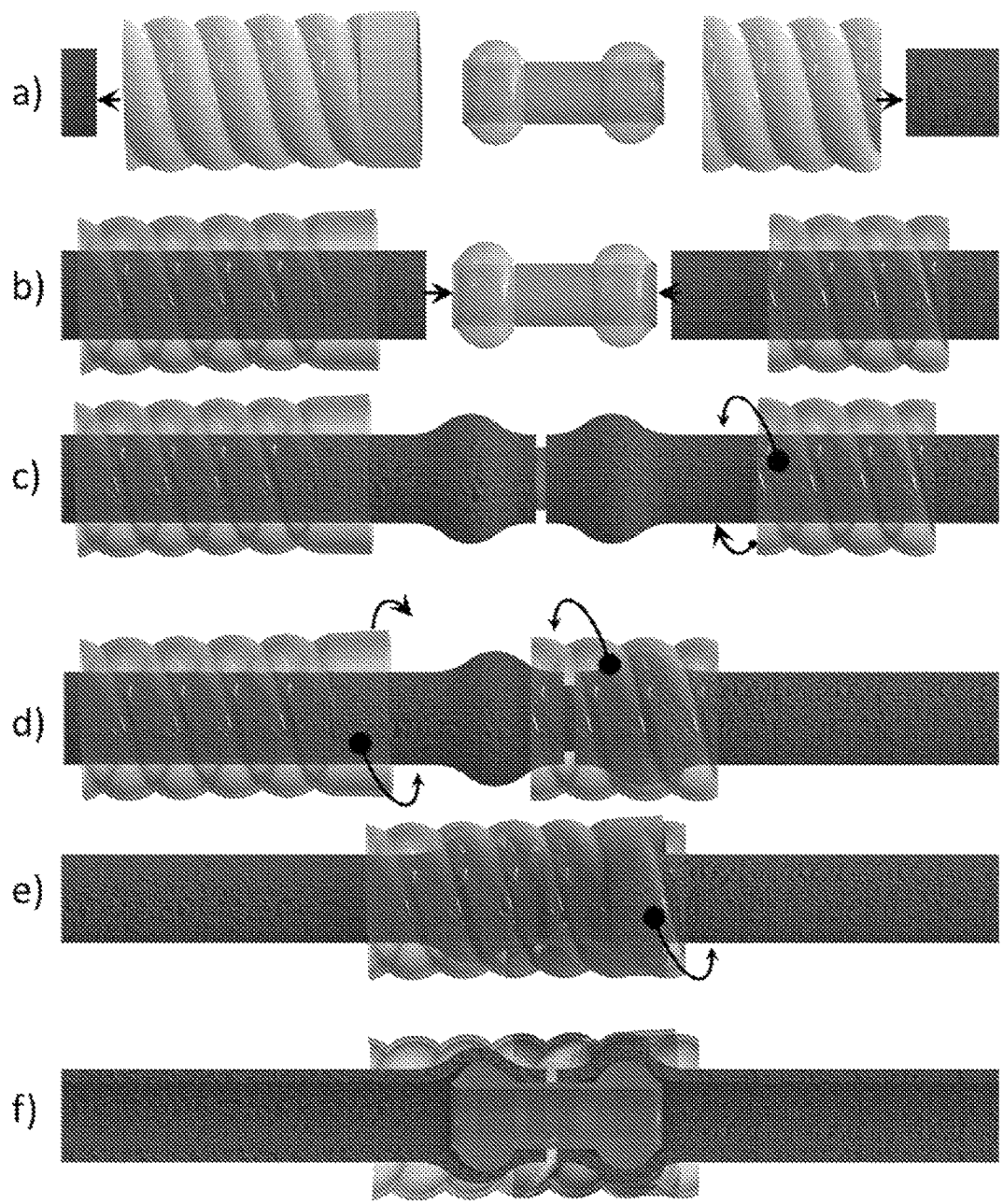
FIG. 6 shows a polymer anastomosis device according to a fifth embodiment of the invention.
Figure 7:
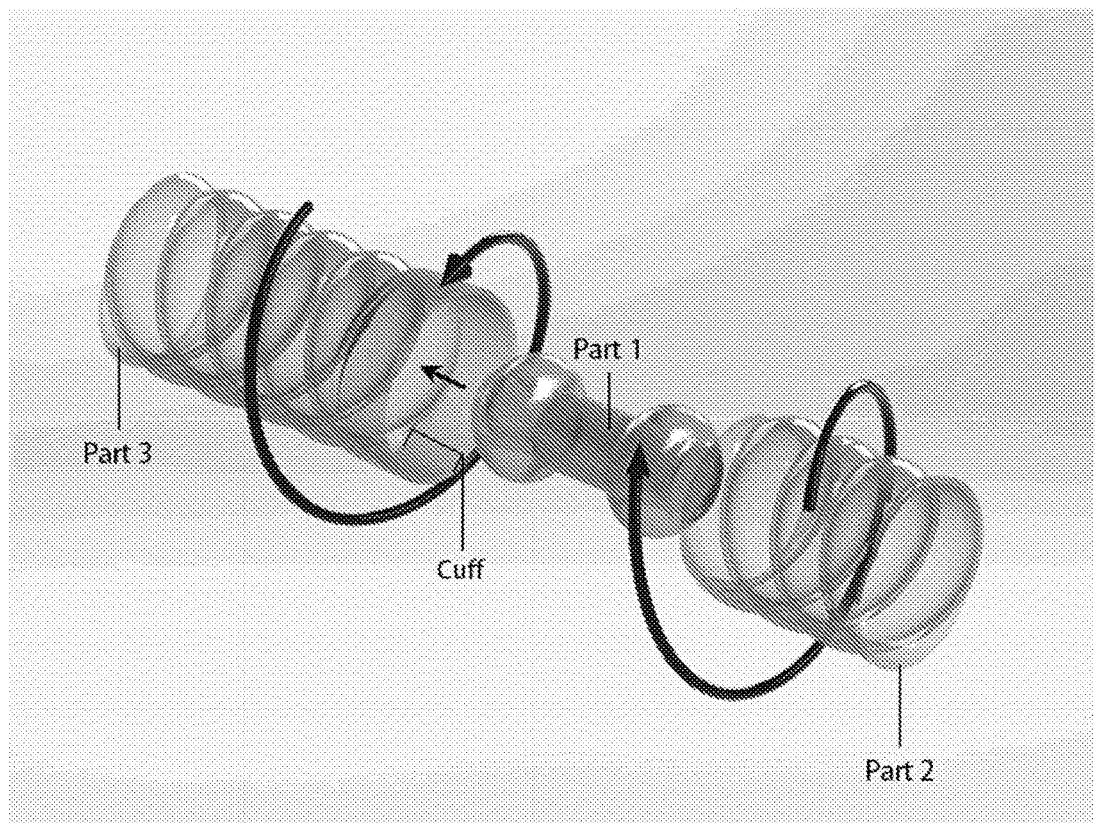
FIG. 7 shows a diagrammatic exploded view of a polymer anastomosis device according to the fifth embodiment of the invention.

FIGS. 6 and 7 show an anastomosis device 600 according to some embodiments of the invention. In this embodiment, the anastomosis device 600 includes a first tube 610 formed of a polymeric material that extends along a longitudinal axis from a first end 612 to a second end 614 and each end 612, 614 can be pressed into the lumen of opposing vessel segments as shown in FIGS. 6c, 6d, 6e and 6f. One or both ends 612, 614 can include spherical barbs or bulges which can be pressed into the lumen of opposing vessel segments. In accordance with some embodiments of the invention, the diameter of the spherical barbs can be in the range of 110% to 140% of the vessel lumen diameter, for example, approximately 125% of the vessel lumen diameter in order to provide increased frictional retaining forces on the outside surface of the anastomosis device. Each end of the device can include a rounded tip 612, 614 which can aid in sealing and securing the anastomosis device without inducing chronic injury at the implant/tissue interface. The anastomosis device 600 can also include a first tubular sheath 616 formed of a polymeric material and a second tubular sheath 618 formed of a polymeric material. The first tubular sheath 616 and the second tubular sheath 618 can each include a single or double helical thread channel that can be sized to mate with the spherical tip on each end 612 and 614 of the first tube 610. The inner thread flank of each tubular sheath 616 and 618, progresses to the thread root at a curvature matching the exterior of each spherical tip on the ends 612 and 614 of the first tube 610. This enables each tubular sheath 616 and 618 to be threaded over each respective spherical tip on the ends 612 and 614 of the first tube 610 after each tip is inserted into the lumen of the respective vessels as shown in FIGS. 6c-6d. In accordance with some embodiments of the invention, the wall thickness of the first tube 610 can be in the range from 100 µm to 300 µm and in some embodiments, approximately 150 µm to 250 µm. In accordance with some embodiments of the invention, the wall thickness of the first tubular sheath 616 and the second tubular sheath 618 can be in the range from 100 µm to 300 µm and in some embodiments, approximately 150 µm. In some particular embodiments, the device 600 of FIGS. 6 and 7 is prepared from a bulk material that comprises or consists of a silk:glycerol blend in a dry weight ratio of 75:25, for example fabricated as described herein.

FIG. 6 also shows an anastomosis procedure according to some embodiments of the invention. In accordance with the invention, the second tubular sheath 616 can be slid around the proximal vessel segment, vessel 1, and the third tubular sheath 618 can be slid around the distal vessel segment as shown in FIG. 6a. Next, the spherical tip on first end 612 can be inserted into the lumen of the proximal vessel, vessel 1, and the spherical tip on second end 614 can be inserted into the lumen of the distal vessel as shown in FIGS. 6b and 6c. Next, the second tubular sheath 618 can be is slid toward the second end 614 of the first tube 610 and rotated around the anastomosis to securely lock the distal vessel, vessel 2 to the spherical tip on the second end 614 of the first tube 610 as shown in FIG. 6d. Next, the first tubular sheath 616 can be is slid toward the first end 612 of the first tube 610 and rotated around the anastomosis to securely lock the proximal vessel, vessel 1 to the spherical tip on the first end 612 of the first tube 610 as shown in FIGS. 6e and 6f. The first tubular sheath 616 can include a cuff or extension to facilitate circumferential alignment with second tubular sheath 618 so that the first tubular sheath 616 can be fastened around the second tubular sheath 618, thereby locking the position of the vessels and implant.

Upon removal of clamps and restoration of blood flow, blood passes from the proximal vessel segment through the lumen of the first tube 610 then into the distal vessel segment. Blood flow contacts the luminal surface of the anastomosis device 600 which can be coated or bulk loaded with a variety of established vascular antithrombotic, antiproliferative, or antibiotic drugs. Where necessary, devices according to this embodiment can span short vessel segment gaps to serve dual function as grafting material as well as performing anastomosis. The anastomosis devices according to this embodiment of the invention can be used where vessels having a lumen diameter of approximately 500 µm to 5000 µm or greater are to be joined. The anastomosis produced according to this embodiment of the invention can be very secure and the helical sheath can provide protection for tissue in-growth. The implantation speed of the anastomosis device according to this embodiment of the invention can be in the range from 1 to 6 minutes.

Each of the embodiments of the invention can be fabricated using silk fibroin materials and blends that include silk fibroin. The use these silk fibroin materials can provide the ability to load and deliver therapeutic compounds and 100% degradability of the silk fibroin material over time. While each of the embodiments can be fabricated using bulk materials consisting of 100% silk fibroin (for example, the embodiment of FIG. 1), fabricating the embodiments using bulk materials that include a blend of silk fibroin and a plasticizer, such as glycerol can also be used. In some particular embodiments, for example, a device is prepared from a bulk material that comprises or consists of a silk:glycerol blend in a dry weight ration of 75:25, for example fabricated as described herein.

Evaluation of Devices

In accordance with some embodiments of the invention, the anastomosis seal was evaluated using a peristaltic pump. In this example, porcine carotid arteries were excised and mounted inline of a pump-driven aqueous flow loop using barb fittings, and secured circumferentially with silk fibroin sutures. The arteries were transected and anastomosed using each of the embodiments described here for comparison. Flow was increased by 100 mL·min$^{-1}$ each hour until reaching 1600 mL·min$^{-1}$, which is 7 times greater than physiological flow and velocity.

Figure 11:
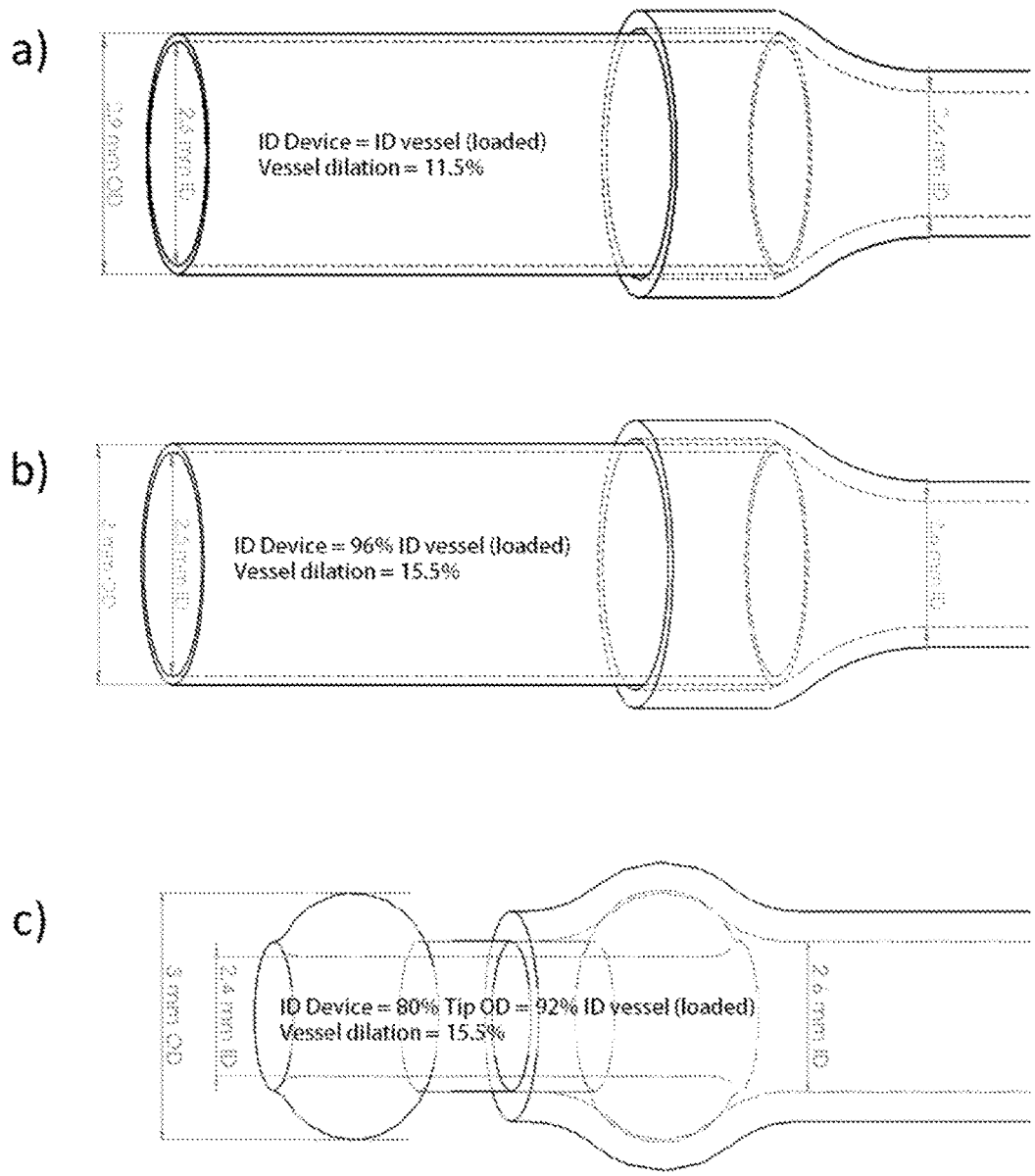
FIGS. 11a, 11b and 11c show optimized diameter sizing of polymer anastomosis devices according to some of the embodiments of the invention.

In accordance with some embodiments of the invention, the target vessel diameters can be clinically evaluated prior to implantation. With this information, anastomosis devices can be sized appropriately. Flow studies have found seals perform optimally when the device internal diameter (I.D.) is equal to the loaded I.D. of the blood vessel, and the blood vessel wall is displaced an additional 11.5% by the implant wall. For example, as shown in FIG. 11a, if the vessel I.D. is 2.6 mm, then an appropriately sized anastomosis device would have an I.D. of 2.6 mm but an outer diameter (O.D.) of 2.9 mm and a wall thickness of 150 µm. However, mechanical evaluation has shown the walls of these anastomosis devices to produce superior strength when the thickness is in the range of 250 µm to 300 µm. For this reason, it is desirable to incorporate thicker implant walls. After reevaluation, optimal fitting in the blood vessel from the previous example exhibiting a loaded I.D. of 2.6 mm, can be accomplished using a anastomosis device having an I.D. of 2.5 mm but an outer diameter (O.D.) of 3 mm (and a wall thickness of 250 µm), producing an additional 15.5% dilation rather than 11.5%. Preliminary surgical implantations have revealed that the embodiments of FIGS. 2 and 6, which use spherical tips as part of the anastomosis mechanism, require reconsideration of the implant dimensions to facilitate the procedure and provide acceptable scaling. Where the spherical tip over-dilates the target vessel in the range of 15%, the internal diameter of the implant can be equivalent to 80% of the sphere outer diameter. This facilitates implantation, sealing, and securing of the anastomosis. Preliminary in vitro flow testing of anastomosis devices according to the embodiments shown in FIGS. 3 and 5, has suggested compression of the load-dilated vessel wall to 90% can be used to produce a secure seal.

Materials

Silk Fibroin

In accordance with some embodiments of the invention, the bulk material, i.e., polymeric material, of the anastomosis device comprises silk fibroin. As used herein, the term "silk fibroin" or "fibroin" includes silkworm fibroin and insect or spider silk protein. See e.g., Lucas et al., 13 Adv. Protein Chem. 107 (1958). Any type of silk fibroin can be used according to aspects of the present invention. Silk fibroin produced by silkworms, such as *Bombyx mori*, is the most common and represents an earth-friendly, renewable resource. For instance, silk fibroin used in can be attained by extracting sericin from the cocoons of *B. mori*. Organic silkworm cocoons are also commercially available. There are many different silks, however, including spider silk (e.g., obtained from *Nephila clavipes*) transgenic silks, genetically engineered silks (recombinant silk), such as silks from bacteria, yeast, mammalian cells, transgenic animals, or transgenic plants, and variants thereof, that can be used. See for example, WO 97/08315 and U.S. Pat. No. 5,245,012, content of both of which is incorporated herein by reference in its entirety. In some embodiments, silk fibroin can be derived from other sources such as spiders, other silkworms, bees, and bioengineered variants thereof. In some embodiments, silk fibroin can be extracted from a gland of silkworm or transgenic silkworms. See for example, WO2007/098951, content of which is incorporated herein by reference in its entirety. In some embodiments, silk fibroin is free, or essentially free, of sericin.

The silk fibroin solution can be prepared by any conventional method known to one skilled in the art. For example, *B. mori* cocoons are boiled for about 30 minutes in an aqueous solution. In one embodiment, the aqueous solution is about 0.02M $Na_2CO_3$. The cocoons are rinsed, for example, with water to extract the sericin proteins and the extracted silk fibroin is dissolved in an aqueous salt solution. Salts useful for this purpose include lithium bromide, lithium thiocyanate, calcium nitrate or other chemicals capable of solubilizing silk fibroin. In some embodiments, the extracted silk fibroin is dissolved in about 8M-12 M LiBr solution. The salt is consequently removed using, for example, dialysis.

If necessary, the solution can then be concentrated using, for example, dialysis against a hygroscopic polymer, for example, PEG, a polyethylene oxide, amylose or sericin. In some embodiments, the PEG is of a molecular weight of 8,000-10,000 g/mol and has a concentration of about 10% to about 50% (w/v). A slide-a-lyzer dialysis cassette (Pierce, MW CO 3500) can be used. However, any dialysis system can be used. The dialysis can be performed for a time period sufficient to result in a final concentration of aqueous silk fibroin solution between about 10% to about 30%. In most cases dialysis for 2-12 hours can be sufficient. See, for example, International Patent Application Publication No. WO 2005/012606, the content of which is incorporated herein by reference in its entirety.

Alternatively, the silk fibroin solution can be produced using organic solvents. Such methods have been described, for example, in Li, M., et al., *J. Appl. Poly Sci.* 2001, 79, 2192-2199; Min, S., et al. *Sen'I Gakkaishi* 1997, 54, 85-92; Nazarov, R. et al., *Biomacromolecules* 2004 May-June; 5(3):718-26, content of all which is incorporated herein by reference in their entirety. An exemplary organic solvent that can be used to produce a silk fibroin solution includes, but is not limited to, hexafluoroisopropanol (HFIP). See, for example, International Application No. WO2004/000915, content of which is incorporated herein by reference in its entirety. Accordingly, in some embodiments, the solution comprising the silk fibroin comprises an organic solvent, e.g., HFIP. In some other embodiments, the solution comprising the silk fibroin is free or essentially free of organic solvents.

Generally, any amount of silk fibroin can be present in the solution. For example, amount of silk fibroin in the solution can be from about 1% (w/v) to about 50% (w/v) of silk fibroin, e.g., silk fibroin. In some embodiments, the amount of silk fibroin in the solution can be from about 1% (w/v) to about 35% (w/v), from about 1% (w/v) to about 30% (w/v), from about 1% (w/v) to about 25% (w/v), from about 1% (w/v) to about 20% (w/v), from about 1% (w/v) to about 15% (w/v), from about 1% (w/v) to about 10% (w/v), from about 5% (w/v) to about 25% (w/v), from about 5% (w/v) to about 20% (w/v), from about 5% (w/v) to about 15% (w/v). Exact amount of silk fibroin in the silk fibroin solution can be determined by drying a known amount of the silk fibroin solution and measuring the mass of the residue to calculate the solution concentration.

Additives

In some embodiments, the bulk material of the anastomosis device comprises one or more (e.g., one, two, three, four, five or more) additives. Without wishing to be bound by a theory, additives can provide one or more desirable properties to the anastomosis device, e.g., strength, flexibility, ease of processing and handling, biocompatibility, bioresorability, lack of air bubbles, surface morphology, and the like. The additive can be covalently or non-covalently linked with silk fibroin and can be integrated homogenously or heterogeneously within the bulk material. The additive can be in any physical form. For example, the additive can be in the form of a particle (e.g., microparticle or nanoparticle), a fiber, a film, a gel, a mesh, a mat, a non-woven mat, a powder, a liquid, or any combinations thereof. The bulk material of the anastomosis device containing the additive can be formulated by mixing one or more additives with the silk fibroin-fibroin solution used to make the stent.

Without limitations, the additive can be selected from the group consisting of anti-proliferative agents, biopolymers, nanoparticles (e.g., gold nanoparticles), proteins, peptides, nucleic acids (e.g., DNA, RNA, siRNA, modRNA), nucleic acid analogs, nucleotides, oligonucleotides, peptide nucleic acids (PNA), aptamers, antibodies or fragments or portions thereof (e.g., paratopes or complementarity-determining regions), antigens or epitopes, hormones, hormone antagonists, growth factors or recombinant growth factors and fragments and variants thereof, cell attachment mediators (such as RGD), cytokines, enzymes, small molecules, antibiotics or antimicrobial compounds, toxins, therapeutic agents and prodrugs, small molecules and any combinations thereof.

Ratio of the silk fibroin to the total amount of additives in the bulk material can range from 100:1 to 1:100. For example, the ratio of silk fibroin to additive can range from 50:1 to 1:50, from 25:1 to 1:25, from 20:1 to 1:20, from 15:1 to 1:15, from 10:1 to 1:10, or from 5:1 to 1:5. In some embodiments, the ratio of silk fibroin to additive can be from 5:1 to 1:1. In one embodiment, the ratio of silk fibroin to additive can be 3:1. The ratio can be molar ratio, weight ratio, or volume ratio.

In some embodiments, the additive is a plasticizer. As used herein, the term "plasticizer" is intended to designate a compound or a mixture of compounds that can increase flexibility, processability and extensibility of the polymer in which it is incorporated. A plasticizer can reduce the viscosity of the melt, lower the second order transition temperatures and the elastic modulus of the product. Suitable plasticizers include, but are not limited to, low molecular weight polyols having aliphatic hydroxyls such as ethylene glycol; propylene glycol; propanetriol (i.e., glycerol); glyceryl monostearate; 1,2-butylene glycol; 2,3-butylene glycol; styrene glycol; polyethylene glycols such as diethylene glycol, triethylene glycol, tetraethylene glycol and other polyethylene glycols having a molecular weight of about 1,000 or less; polypropylene glycols of molecular weight 200 or less; glycol ethers such as monopropylene glycol monoisopropyl ether; propylene glycol monoethyl ether; ethylene glycol monoethyl ether, diethylene glycol monoethyl ether; ester-type plasticizers such as sorbitol lactate, ethyl lactate, butyl lactate, ethyl glycolate, allyl glycolate; and amines such as monoethanolamine, diethanolamine, triethanolamine, monoisopropanolamine, triethylenetetramine, 2-amino-2-methyl-1,3-propanediol, polymers and the like. In one embodiment, the plasticizer can include glycerol.

In some embodiments, the additive is a polymer. In some embodiments, the polymer is a biocompatible polymer. As used herein, the term "biocompatible polymer" refers to any polymeric material that does not deteriorate appreciably and does not induce a significant immune response or deleterious tissue reaction, e.g., toxic reaction or significant irritation, over time when implanted into or placed adjacent to the biological tissue of a subject, or induce blood clotting or coagulation when it comes in contact with blood. Exemplary biocompatible polymers include, but are not limited to, a poly-lactic acid (PLA), poly-glycolic acid (PGA), poly-lactide-co-glycolide (PLGA), polyesters, poly(ortho ester), poly(phosphazine), poly(phosphate ester), polycaprolactone, gelatin, collagen, fibronectin, keratin, polyaspartic acid, alginate, chitosan, chitin, hyaluronic acid, pectin, polyhydroxyalkanoates, dextrans, and polyanhydrides, polyethylene oxide (PEO), poly(ethylene glycol) (PEG), triblock copolymers, polylysine, alginate, polyaspartic acid, any derivatives thereof and any combinations thereof. Other exemplary biocompatible polymers amenable to use according to the present disclosure include those described for example in U.S. Pat. Nos. 6,302,848; 6,395,734; 6,127,143; 5,263,992; 6,379,690; 5,015,476; 4,806,355; 6,372,244; 6,310,188; 5,093,489; No. U.S. 387,413; U.S. Pat. Nos. 6,325,810; 6,337,198; 6,267,776; 5,576,881; 6,245,537; 5,902,800; and 5,270,419, content of all of which is incorporated herein by reference.

In some embodiments, the biocompatible polymer is PEG or PEO. As used herein, the term "polyethylene glycol" or "PEG" means an ethylene glycol polymer that contains about 20 to about 2000000 linked monomers, typically about 50-1000 linked monomers, usually about 100-300. PEG is also known as polyethylene oxide (PEO) or polyoxyethylene (POE), depending on its molecular weight. Generally PEG, PEO, and POE are chemically synonymous, but historically PEG has tended to refer to oligomers and polymers with a molecular mass below 20,000 g/mol, PEO to polymers with a molecular mass above 20,000 g/mol, and POE to a polymer of any molecular mass. PEG and PEO are liquids or low-melting solids, depending on their molecular weights. PEGs are prepared by polymerization of ethylene oxide and are commercially available over a wide range of molecular weights from 300 g/mol to 10,000,000 g/mol. While PEG and PEO with different molecular weights find use in different applications, and have different physical properties (e.g. viscosity) due to chain length effects, their chemical properties are nearly identical. Different forms of PEG are also available, depending on the initiator used for the polymerization process—the most common initiator is a monofunctional methyl ether PEG, or methoxypoly(ethylene glycol), abbreviated mPEG. Lower-molecular-weight PEGs are also available as purer oligomers, referred to as monodisperse, uniform, or discrete PEGs are also available with different geometries.

As used herein, the term PEG is intended to be inclusive and not exclusive. The term PEG includes poly(ethylene glycol) in any of its forms, including alkoxy PEG, difunctional PEG, multiarmed PEG, forked PEG, branched PEG, pendent PEG (i.e., PEG or related polymers having one or more functional groups pendent to the polymer backbone), or PEG With degradable linkages therein. Further, the PEG backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as R(-PEG-OH)m in which R represents the core moiety, such as glycerol or pentaerythritol, and m represents the number of arms. Multiarmed PEG molecules, such as those described in U.S. Pat. No. 5,932,462, which is incorporated by reference herein in its entirety, can also be used as biocompatible polymers.

Some exemplary PEGs include, but are not limited to, PEG20, PEG30, PEG40, PEG60, PEG80, PEG100, PEG115, PEG200, PEG300, PEG400. PEG500, PEG600, PEG1000, PEG1500, PEG2000, PEG3350, PEG4000, PEG4600, PEG5000, PEG6000, PEG8000, PEG11000, PEG12000, PEG15000, PEG20000, PEG250000, PEG500000, PEG100000, PEG2000000 and the like. In some embodiments, PEG is of MW 10,000 Dalton. In some embodiments, PEG is of MW 100,000, i.e. PEO of MW 100,000.

In some embodiments, the polymer is a biodegradable polymer. As used herein, the term "biodegradable" describes a material which can decompose under physiological conditions into breakdown products. Such physiological conditions include, for example, hydrolysis (decomposition via hydrolytic cleavage), enzymatic catalysis (enzymatic degradation), and mechanical interactions. As used herein, the term "biodegradable" also encompasses the term "bioresorbable", which describes a substance that decomposes under physiological conditions to break down to products that undergo bioresorption into the host-organism, namely, become metabolites of the biochemical systems of the host organism. As used herein, the terms "bioresorbable" and "bioresorption" encompass processes such as cell-mediated degradation, enzymatic degradation and/or hydrolytic degradation of the bioresorbable polymer, and/or elimination of the bioresorbable polymer from living tissue as will be appreciated by the person skilled in the art.

The term "biodegradable polymer", as used herein, refers to a polymer that at least a portion thereof decomposes under physiological conditions. The polymer can thus be partially decomposed or fully decomposed under physiological conditions. Exemplary biodegradable polymers include, but are not limited to, polyanhydrides, polyhydroxybutyric acid, polyorthoesters, polysiloxanes, polycaprolactone, poly(lactic-co-glycolic acid), poly(lactic acid), poly(glycolic acid), and copolymers prepared from the monomers of these polymers.

In some embodiments, the additive comprises a bioinert material. As used herein, the term "bioinert" refers to any material that once placed in vivo has minimal interaction with its surrounding tissue. Exemplary bioinert materials include, but are not limited to, gold, stainless steel, titanium, alumina, partially stabilized zirconia, and ultra-high molecular weight polyethylene.

In some embodiments, the additive can be selected from the group consisting of polyethylene oxide (PEO), polyethylene glycol (PEG), collagen, fibronectin, keratin, polyaspartic acid, polylysine, alginate, chitosan, chitin, hyaluronic acid, pectin, polycaprolactones, polylactic acid, polyglycolic acid, polyhydroxyalkanoates, dextrans, polyanhydrides, and any combinations thereof.

In some embodiments, the additive can be a silk fibroin particle or powder. Various methods of producing silk fibroin particles (e.g., nanoparticles and microparticles) are known in the art. See for example, PCT Publication No. WO 2011/041395 and No. WO 2008/118133; U.S. App. Pub. No. U.S. 2010/0028451; U.S. Provisional Application Ser. No. 61/719,146, filed Oct. 26, 2012; and Wenk et al. J Control Release, Silk fibroin spheres as a platform for controlled drug delivery, 2008; 132: 26-34, content of all of which is incorporated herein by reference in their entirety.

In some embodiments, the additive is a silk fibroin fiber. In some embodiments, silk fibroin fibers could be chemically attached by redissolving part of the fiber in HFIP and attaching to stent. Use of silk fibroin fibers is described in, for example, US patent application publication no. US20110046686, content of which is incorporated herein by reference.

In some embodiments, the silk fibroin fibers are microfibers or nanofibers. In some embodiments, the additive is micron-sized silk fibroin fiber (10-600 μm). Micron-sized silk fibroin fibers can be obtained by hydrolyzing the degummed silk fibroin or by increasing the boing time of the degumming process. Alkali hydrolysis of silk fibroin to obtain micron-sized silk fibroin fibers is described for example in Mandal et al., PNAS, 2012, doi: 10.1073/pnas.1119474109; U.S. Provisional Application No. 61/621,209, filed Apr. 6, 2012; and PCT application no. PCT/US13/35389, filed Apr. 5, 2013, content of all of which is incorporated herein by reference. Because regenerated silk fibroin fibers made from HFIP silk fibroin solutions are mechanically strong, the regenerated silk fibroin fibers can also be used as additive.

In some embodiments, the silk fibroin fiber is an unprocessed silk fibroin fiber e.g., raw silk fibroin or raw silk fibroin fiber. The term "raw silk fibroin" or "raw silk fibroin fiber" refers to silk fibroin fiber that has not been treated to remove sericin, and thus encompasses, for example, silk fibroin fibers taken directly from a cocoon Thus, by unprocessed silk fibroin fiber is meant silk fibroin, obtained directly from the silk fibroin gland. When silk fibroin, obtained directly from the silk fibroin gland, is allowed to dry, the structure is referred to as silk fibroin I in the solid state. Thus, an unprocessed silk fibroin fiber comprises silk fibroin mostly in the silk fibroin I conformation. A regenerated or processed silk fibroin fiber on the other hand comprises silk fibroin having a substantial silk fibroin II or beta-sheet crystallinity.

Biologically Active Agents

In some embodiment, the bulk material of the anastomosis device can comprise a biologically active agent. As used herein, the term "biological activity" or "bioactivity" refers to the ability of a molecule or composition to affect a biological sample. Biological activity can include, without limitation, elicitation of a stimulatory, inhibitory, regulatory, toxic or lethal response in a biological assay. For example, a biological activity can refer to the ability of a compound to modulate the effect/activity of an enzyme, block a receptor, stimulate a receptor, modulate the expression level of one or more genes, modulate cell proliferation, modulate cell division, modulate cell morphology, or any combination thereof. In some instances, a biological activity can refer to the ability of a compound to produce a toxic effect in a biological sample. The bulk material of the anastomosis device containing the active agent can be formulated by mixing one or more active agents with the silk fibroin solution used to make the stent.

Without limitations, the active agent can be selected from small organic or inorganic molecules; saccharines; oligosaccharides; polysaccharides; biological macromolecules; peptides; proteins; peptide analogs and derivatives; peptidomimetics; antibodies and antigen binding fragments thereof; nucleic acids; nucleic acid analogs and derivatives; glycogens or other sugars; immunogens; antigens; an extract made from biological materials such as bacteria, plants, fungi, or animal cells; animal tissues; naturally occurring or synthetic compositions; and any combinations thereof. The active agent can be hydrophobic, hydrophilic, or amphiphilic.

As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight of less than 5000 Daltons (5 kD), preferably less than 3 kD, still more preferably less than 2 kD, and most preferably less than 1 kD. In some cases it is highly preferred that a small molecule have a molecular mass equal to or less than 700 Daltons.

Total amount of active agent in the bulk material can be from about 0.1 wt % to about 0.99 wt %, from about 0.1 wt % to about 70 wt %, from about 5 wt % to about 60 wt %, from about 10 wt % to about 50 wt %, from about 15 wt % to about 45 wt %, or from about 20 wt % to about 40 wt %, of the total weight of the bulk material.

Without wishing to be bound by a theory, the active agent can be covalently or non-covalently associated with the bulk material. In some embodiments, the active agent is distributed homogenously in the bulk material, e.g., silk fibroin matrix. In some embodiments, the active agent is absorbed/adsorbed on a surface of the stent.

Examples of biologically active compounds include, but are not limited to: cell attachment mediators, such as collagen, elastin, fibronectin, vitronectin, laminin, proteoglycans, or peptides containing known integrin binding domains e.g. "RGD" integrin binding sequence, or variations thereof, that are known to affect cellular attachment (Schaffner P & Dard, Cell Mol Life Sci., 2003, 60(1):119-32 and Hersel U. et al., Biomaterials, 2003, 24(24):4385-415); YIGSR peptides;

biologically active ligands; and substances that enhance or exclude particular varieties of cellular or tissue ingrowth.

In some embodiments, the active agent is a growth factor or cytokine. A non-limiting list of growth factors and cytokines includes, but is not limited, to stem cell factor (SCF), granulocyte-colony stimulating factor (G-CSF), granulocyte-macrophage stimulating factor (GM-CSF), stromal cell-derived factor-1, steel factor, VEGF, TGFβ, platelet derived growth factor (PDGF), angiopoeitins (Ang), epidermal growth factor (EGF), bFGF, HNF, NGF, bone morphogenic protein (BMP), fibroblast growth factor (FGF), hepatocye growth factor, insulin-like growth factor (IGF-1), interleukin (IL)-3, IL-1α, IL-1β, IL-6, IL-7, IL-8, IL-11, and IL-13, colony-stimulating factors, thrombopoietin, ecrythropoietin, fit3-ligand, and tumor necrosis factors (TNFα and TNFβ). Other examples are described in Dijke et al., "Growth Factors for Wound Healing", Bio/Technology, 7:793-798 (1989); Mulder G D, Haberer P A, Jeter K F, eds. Clinicians' Pocket Guide to Chronic Wound Repair. 4th ed. Springhouse, PA: Springhouse Corporation; 1998:85; Ziegler T. R., Pierce, G. F., and Herndon, D. N., 1997, International Symposium on Growth Factors and Wound Healing: Basic Science & Potential Clinical Applications (Boston, 1995, Serono Symposia USA), Publisher Springer Verlag.

In some embodiments, the active agent can be selected from anti-infectives such as antibiotics and antiviral agents; chemotherapeutic agents (i.e. anticancer agents); anti-rejection agents; anti-proliferative agents; analgesics and analgesic combinations; anti-inflammatory agents; erythropoietin (EPO); interferon α and γ; interleukins; tumor necrosis factor α and β; insulin, antibiotics; adenosine; cytokines; integrins; selectins; cadherins; insulin; hormones such as steroids; cytotoxins; prodrugs; immunogens; or lipoproteins.

In some embodiments, the active agent is a therapeutic agent. As used herein, the term "therapeutic agent" refers to a biological or chemical agent used for treating, curing, mitigating, or preventing deleterious conditions in a subject. The term "therapeutic agent" also includes substances and agents for combating a disease, condition, or disorder of a subject, and includes drugs, diagnostics, and instrumentation. "Therapeutic agent" also includes anything used in medical diagnosis, or in restoring, correcting, or modifying physiological functions. The terms "therapeutic agent" and "pharmaceutically active agent" are used interchangeably herein.

The therapeutic agent is selected according to the treatment objective and biological action desired. General classes of therapeutic agents include anti-microbial agents such as adrenergic agents, antibiotic agents or antibacterial agents, antiviral agents, anthelmintic agents, anti-inflammatory agents, antineoplastic agents, antioxidant agents, biological reaction inhibitors, botulinum toxin agents, chemotherapy agents, diagnostic agents, gene therapy agents, hormonal agents, mucolytic agents, radioprotective agents, radioactive agents including brachytherapy materials, tissue growth inhibitors, tissue growth enhancers, and vasoactive agents. The therapeutic agent can be selected from any class suitable for the therapeutic objective. For example, if the objective is treating a disease or condition associated narrowing in a blood vessel or other tubular organ or structure, the therapeutic agent can include antithrombotic or fibrinolytic agents.

Exemplary pharmaceutically active compound include, but are not limited to, those found in *Harrison's Principles of Internal Medicine*, 13th Edition, Eds. T. R. Harrison et al. McGraw-Hill N.Y., NY; Physicians' Desk Reference, 50th Edition, 1997, Oradell New Jersey, Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete content of all of which are herein incorporated in its entirety.

In some embodiments, the therapeutic agent can be selected from the group consisting of anti-infectives, chemotherapeutic agents, anti-rejection agents, analgesics and analgesic combinations, anti-inflammatory agents, hormones, growth factors, antibiotics, antiviral agents, steroids, bone morphogenic proteins, bone morphogenic-like proteins, epidermal growth factor, fibroblast growth factor, platelet erived growth factor (PDGF), insulin-like growth factor, transforming growth factors, vascular endothelial growth factor, and any combinations thereof.

In some embodiments, the therapeutic agent is an anti-thrombotic or fibrinolytic agent selected from the group consisting of anticoagulants, anticoagulant antagonists, antiplatelet agents, thrombolytic agents, thrombolytic agent antagonists, and any combinations thereof.

In some embodiments, the therapeutic agent is thrombogenic agent selected from the group consisting of thrombolytic agent antagonists, anticoagulant antagonists, pro-coagulant enzymes, pro-coagulant proteins, and any combinations thereof. Some exemplary thrombogenic agents include, but are not limited to, protamines, vitamin K1, amiocaproic acid (amicar), tranexamic acid (amstat), anagrelide, argatroban, cilstazol, daltroban, defibrotide, enoxaparin, fraxiparine, indobufen, lamoparan, ozagrel, picotamide, plafibride, tedelparin, ticlopidine, triflusal, collagen, and collagen-coated particles.

In some embodiments, the therapeutic agent is a vasodilator. A vasodilator can be selected from the group consisting of alpha-adrenoceptor antagonists (alpha-blockers), agiotensin converting enzyme (ACE) inhibitors, angiotensin receptor blockers (ARBs), beta2-adrenoceptor agonists (β2-agonists), calcium-channel blockers (CCBs), centrally acting sympatholytics, direct acting vasodilators, endothelin receptor antagonists, ganglionic blockers, nitrodilators, phosphodiesterase inhibitors, potassium-channel openers, renin inhibitors, and any combinations thereof. Exemplary vasodilator include, but are not limited to, prazosin, terazosin, doxazosin, trimazosin, phentolamine, phenoxybenzamine, benazepril, captopril, enalapril, fosinopril, lisinopril, moexipril, quinapril, ramipril, candesartan, eprosartan, irbesartan, losartan, olmesartan, telmisartan, valsartan, Epinephrine, Norepinephrine, Dopamine, Dobutamine, Isoproterenol, amlodipine, felodipine, isradipine, nicalrdipine, nifedipine, nimodipine, nitrendipine, clonidine, guanabenz, guanfacine, α-methyldopa, hydralazine, Bosentan, trimethaphan camsylate, isosorbide dinitrate, isosorbide mononitrate, nitroglycerin, erythrityl tetranitrate, pentaerythritol tetranitrate, sodium nitroprusside, milrinone, inamrinone (formerly amrinone), cilostazol, sildenafil, tadalafil, minoxidil, aliskiren, and analogs, derivatives, prodrugs, and pharmaceutically acceptable salts thereof.

In some embodiments, the active agent is an anti-restenosis or restenosis inhibiting agent. Suitable anti-restenosis agents include: (1) antiplatelet agents including: (a) thrombin inhibitors and receptor antagonists, (b) adenosine disphosphate (ADP) receptor antagonists (also known as purinoceptor$_1$ receptor antagonists), (c) thromboxane inhibitors and receptor antagonists and (d) platelet membrane glycoprotein receptor antagonists; (2) inhibitors of cell adhesion molecules, including (a) selectin inhibitors and (b) integrin inhibitors; (3) anti-chemotactic agents; (4) interleukin receptor antagonists (which also serve as anti-pain/anti-inflammation agents); and (5) intracellular signaling inhibitors including: (a) protein kinase C (PKC) inhibitors and protein tyrosine kinase inhibitors, (b) modulators of intracellular protein tyrosine phosphatases, (c) inhibitors of src homology$_2$ (SH2) domains, and (d) calcium channel antagonists. Exemplary specific restenosis-inhibiting agents include microtubule stabilizing agents such as rapamycin, mitomycin C, TAXOL®, paclitaxel (I.e., paclitaxel, paxlitaxel analogs, or paclitaxel derivatives, and mixtures thereof). For example, derivatives suitable for use in the anastomosis device include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, and 2'-O-ester with N-(dimethylaminoethyl) glutamide hydrochloride salt.

In some embodiments, the active agent is an anti-coagulation agent. As used herein, the term "anti-coagulation agent" refers to any molecule or composition that promotes blood coagulation or activates the blood coagulation cascade or a portion thereof. Exemplary anti-coagulation agents include, for example, phospholipids such as, e.g., negatively charged phospholipids; lipoproteins such as, e.g., thromboplastin, and the like; proteins such as tissue factor, activated serin proteases such as Factors IIa (thrombin), VII, VIIa, VIII, IX, IXa, Xa, XIa, XII, XIIa, von Willebrand factor (vWF), protein C, snake venoms such as PROTAC® enzyme, Ecarin, Textarin, Noscarin, Batroxobin, Thrombocytin, Russell's viper venom (RVV), and the like; polyvalent cations; calcium ions; tissue factor, silica; kaolin; bentonite; diatomaceous earth; ellagic acid; celitc; and any mixtures thereof.

In some embodiments, the agent is a nitric oxide or a prodrug thereof.

Without wishing to be bound by a theory, incorporating an active agent in the bulk material of the anastomosis device enables the delivery of active agent in a controlled released manner. Maintaining the active agent in an active form throughout the process of incorporating the agent in the silk fibroin-fibroin matrix enables it to be active upon release from the stent. Controlled release of the active agent permits active agent to be released sustainably over time, with controlled release kinetics. In some instances, the active agent is delivered continuously to the site where treatment is needed, for example, over several weeks. Controlled release over time, for example, over several days or weeks, or longer, permits continuous delivery of the bioactive agent to obtain preferred treatments. The controlled delivery is advantageous because it protects the bioactive agent from degradation in vivo in body fluids and tissue, for example, by proteases.

Controlled release of the active agent from the anastomosis device can be designed to occur over time, for example, over 12 hours or 24 hours. The time of release may be selected, for example, to occur over a time period of about 12 hours to 24 hours; about 12 hours to 42 hours; or, e.g., about 12 to 72 hours. In another embodiment, release can occur for example on the order of about 1 day to 15 days. The controlled release time can be selected based on the condition treated. For example, longer times can be more effective for wound healing, whereas shorter delivery times can be more useful for some cardiovascular applications.

Controlled release of the active agent from the anastomosis device in vive can occur, for example, in the amount of about 1 ng to 1 mg/day. In other embodiments, the controlled release can occur in the amount of about 50 ng to 500 ng/day, about 75 ng to 250 ng/day, about 100 ng to 200 ng/day, or about 125 ng to 175 ng/day.

In some embodiments, the active agent is an enzyme that hydrolyzes silk fibroin. Without wishing to be bound by a theory, such enzymes can be used to control the degradation of the anastomosis device after implantation into a subject. Controlled degradation of silk fibroin-fibroin based scaffolds with enzymes embedded therein is described in, for example, U.S. Provisional Application No. 61/791,501, filed Mar. 15, 2013, content of which is incorporated herein by reference in its entirety.

Cells

In some embodiments, the bulk material of the anastomosis device can comprise a cell. Anastomosis device with the bulk material comprising a cell can be used for organ repair, organ replacement or regeneration. Cells amenable to be incorporated into the composition include, but are not limited to, stem cells (embryonic stem cells, mesenchymal stem cells, neural stem cells, bone-marrow derived stem cells, hematopoietic stem cells, and induced pluripotent stem cells); pluripotent cells; chondrocytes progenitor cells; pancreatic progenitor cells; myoblasts; fibroblasts; chondrocytes; keratinocytes; neuronal cells; glial cells; astrocytes; pre-adipocytes; adipocytes; vascular endothelial cells; hair follicular stem cells; endothelial progenitor cells; mesenchymal cells; smooth muscle progenitor cells; osteocytes; parenchymal cells such as hepatocytes; pancreatic cells (including Islet cells); cells of intestinal origin; and combination thereof, either as obtained from donors, from established cell culture lines, or even before or after molecular genetic engineering. Without limitations, the cells useful for incorporation into the composition can come from any source, for example human, rat or mouse. In some embodiments, the cell can from a subject into which the anastomosis device is to be implanted.

In some embodiments, the cell is a genetically modified cell. A cell can be genetically modified to express and secrete a desired compound, e.g. a bioactive agent, a growth factor, differentiation factor, cytokines, and the like. Methods of genetically modifying cells for expressing and secreting compounds of interest are known in the art and easily adaptable by one of skill in the art.

Differentiated cells that have been reprogrammed into stem cells can also be used. For example, human skin cells reprogrammed into embryonic stem cells by the transduction of Oct3/4, Sox2, c-Myc and Klf4 (Junying Yu, et. al., *Science,* 2007, 318, 1917-1920 and Takahashi K. et. al., *Cell,* 2007, 131, 1-12).

When using a anasomosis device with cells, it can be desirable to add other materials to promote the growth, differentiation or proliferation of the cell. Exemplary materials known to promote cell growth include, but not limited to, cell growth media, such as Dulbecco's Modified Eagle Medium (DMEM), fetal bovine serum (FBS), non-essential amino acids and antibiotics, and growth and morphogenic factors such as fibroblast growth factor (e.g., FGF 1-9), transforming growth factors (TGFs), vascular endothelial growth factor (VEGF), epidermal growth factor (EGF), platelet derived growth factor (PDGF), insulin-like growth factor (IGF-I and IGF-II), bone morphogenetic growth factors (e.g., BMPs 1-7), bone morphogenetic-like proteins (e.g., GFD-5, GFD-7, and GFD-8), transforming growth factors (e.g., TGF-α, TGF-β I-III), nerve growth factors, and related proteins. Growth factors are known in the art, see. e.g., Rosen & Thies, CELLULAR & MOL. BASIS BONE FORMATION & REPAIR (R. G. Landes Co.).

Material Properties and Modification
Crystallinity

Optionally, the conformation of the silk fibroin in the anastomosis device can be altered before, during or after formation of the device. The induced conformational change alters the crystallinity of the silk fibroin, e.g., Silk fibroin II beta-sheet crystallinity. Without wishing to be bound by a theory, it is believed that degradation of the bulk material or optional release of an additive (e.g., an active agent) from the bulk material varies with the beta-sheet content of the silk fibroin. The conformational change can be induced by any methods known in the art, including, but not limited to, alcohol immersion (e.g., ethanol, methanol), water annealing, shear stress (e.g., by vortexing), ultrasound (e.g., by sonication), pH reduction (e.g., pH titration and/or exposure to an electric field) and any combinations thereof. For example, the conformational change can be induced by one or more methods, including but not limited to, controlled slow drying (Lu et al., 10 Biomacromolecules 1032 (2009)); water annealing (Jin et al., Water-Stable Silk fibroin Films with Reduced β-Sheet Content, 15 Adv. Funct. Mats. 1241 (2005); Hu et al. Regulation of Silk fibroin Material Structure by Temperature-Controlled Water Vapor Annealing, 12 Biomacromolecules 1686 (2011)); stretching (Demura & Asakura, Immobilization of glucose oxidase with *Bombyx mori* silk fibroin by only stretching treatment and its application to glucose sensor, 33 Biotech & Bioengin. 598 (1989)); compressing; solvent immersion, including methanol (Hofmann et al., Silk fibroin as an organic polymer for controlled drug delivery, 111 J Control Release. 219 (2006)), ethanol (Miyairi et al., Properties of b-glucosidase immobilized in sericin membrane. 56 J. Fermen. Tech. 303 (1978)), glutaraldehyde (Acharya et al., Performance evaluation of a silk fibroin protein-based matrix for the enzymatic conversion of tyrosine to L-DOPA. 3 Biotechnol J. 226 (2008)), and 1-ethyl-3-(3-dimethyl aminopropyl) carbodiimide (EDC) (Bayraktar et al., Silk fibroin as a novel coating material for controlled release of theophylline. 60 Eur J Pharm Biopharm. 373 (2005)); pH adjustment, e.g., pH titration and/or exposure to an electric field (see, e.g., U.S. Patent App. No. US2011/0171239); heat treatment; shear stress (see, e.g., International App. No.: WO 2011/005381), ultrasound, e.g., sonication (see, e.g., U.S. Patent Application Publication No. U.S. 2010/0178304 and International App. No. WO2008/150861); and any combinations thereof. Content of all of the references listed above is incorporated herein by reference in their entirety.

In some embodiments, the conformation of the silk fibroin can be altered by water annealing. Without wishing to be bound by a theory, it is believed that physical temperature-controlled water vapor annealing (TCWVA) provides a simple and effective method to obtain refined control of the molecular structure of silk fibroin biomaterials. The silk fibroin materials can be prepared with control of crystallinity, from a low content, using conditions at 4° C. (α helix (alpha-helix) dominated silk fibroin I structure), to highest content of ~60% crystallinity at 100° C. (β-sheet (beta-sheet) dominated silk fibroin II structure). This physical approach covers the range of structures previously reported to govern crystallization during the fabrication of silk fibroin materials, yet offers a simpler, green chemistry, approach with tight control of reproducibility. Temperature controlled water vapor annealing is described, for example, in Hu et al., Regulation of Silk fibroin Material Structure By Temperature Controlled Water Vapor Annealing, Biomacromolecules, 2011, 12(5): 1686-1696, content of which is incorporated herein by reference in its entirety.

In some embodiments, alteration in the conformation of the silk fibroin can be induced by immersing in alcohol, e.g., methanol, ethanol, etc. The alcohol concentration can be at least 10%, at least 20%, at least 30%, at least 40%, at least 50%, at least 60%, at least 70%, at least 80%, at least 90% or 100%. In some embodiment, alcohol concentration is 100%. If the alteration in the conformation is by immersing in a solvent, the silk fibroin composition can be washed, e.g., with solvent/water gradient to remove any of the residual solvent that is used for the immersion. The washing can be repeated one, e.g., one, two, three, four, five, or more times.

In some embodiments, the alteration in the conformation of the silk fibroin can be induced with sheer stress. The sheer stress can be applied, for example, by passing the silk fibroin composition through a needle. Other methods of inducing conformational changes include applying an electric field, applying pressure, or changing the salt concentration.

The treatment time for inducing the conformational change can be any period of time to provide a desired silk fibroin II (beta-sheet crystallinity) content. In some embodiments, the treatment time can range from about 1 hour to about 12 hours, from about 1 hour to about 6 hours, from about 1 hour to about 5 hours, from about 1 hour to about 4 hours, or from about 1 hour to about 3 hours. In some embodiments, the sintering time can range from about 2 hours to about 4 hours or from 2.5 hours to about 3.5 hours.

When inducing the conformational change is by solvent immersion, treatment time can range from minutes to hours. For example, immersion in the solvent can be for a period of at least about 15 minutes, at least about 30 minutes, at least about 1 hour, at least about 2 hours, at least 3 hours, at least about 6 hours, at least about 18 hours, at least about 12 hours, at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, or at least about 14 days. In some embodiments, immersion in the solvent can be for a period of about 12 hours to about seven days, about 1 day to about 6 days, about 2 to about 5 days, or about 3 to about 4 days. In one embodiment, immersion in the solvent can be for a period of about minutes.

Without limitations, the silk fibroin in the anastomosis device can comprise a silk fibroin II beta-sheet crystallinity content of at least about 5%, at least about 10%, at least about 20%, at least about 30%, at least about 40%, at least about 50%, at least about 60%, at least about 70%, at least about 80%, at least about 90%, or at least about 95% but not 100% (i.e., all the silk fibroin is present in a silk fibroin II beta-sheet conformation). In some embodiments, silk fibroin in the anastomosis device is present completely in a silk fibroin II beta-sheet conformation, i.e., 100% silk fibroin II beta-sheet crystallinity.

Porosity

To improve controlled endothelialization and remodeling of the anastomosis device, the wall formulation can be modified to incorporate finely tuned nano- or micro-porosities. Without wishing to be bound by a theory, nano-porosity in the wall of the vessel anastomosis device can facilitate nutrient, oxygen, and waste exchange improving natural vessel healing. The porosity can be tuned in such a way that a controlled amount of fluid will be diffused to allow this beneficial exchange without harmful loss blood pressure or volume. Accordingly, in some embodiments, the anastomosis device can be porous, i.e., the bulk material (e.g., wall of the device) can comprise pores, such as nanopores or micropores.

For example, the bulk material of the anastomosis device can have a porosity of at least about 10%, at least about 20%, at least about 30%, at least about 40%, at least about 50%, at least about 60%, at least about 70%, at least about 80%, at least about 90%, or higher. One of skill in the art can adjust the porosity accordingly, based on a number of factors such as, but not limited to, desired physical or mechanical properties of the stent, release rates, molecular size and/or diffusion coefficient of the molecule distributed in the bulk material, and/or concentrations, amounts of silk fibroin in the bulk material. As used herein, the term "porosity" is a measure of void spaces in a material and is a fraction of volume of voids over the total volume, as a percentage between 0 and 100% (or between 0 and 1). Determination of porosity is well known to a skilled artisan, e.g., using standardized techniques, such as mercury porosimetry and gas adsorption, e.g., nitrogen adsorption.

The pores can be of any desired pore size. As used herein, the term "pore size" refers to a diameter or an effective diameter of the cross-sections of the pores. The term "pore size" can also refer to an average diameter or an average effective diameter of the cross-sections of the pores, based on the measurements of a plurality of pores. The effective diameter of a cross-section that is not circular equals the diameter of a circular cross-section that has the same cross-sectional area as that of the non-circular cross-section. In some embodiments, the pores can have a size distribution ranging from about 50 nm to about 1000 µm, from about 250 nm to about 500 µm, from about 500 nm to about 250 µm, from about 1 µm to about 200 µm, from about 10 µm to about 150 µm, or from about 50 µm to about 100 µm. In some embodiments, the anastomosis device can be swellable when hydrated. The sizes of the pores can then change depending on the water content in the stent. In some embodiment, the pores can be filled with a fluid such as water or air.

Methods for forming pores in silk fibroin-based scaffolds are known in the art and include, but are not limited, porogen-leaching methods, freeze-drying methods, and/or gas-forming method. Exemplary methods for forming pores in a silk fibroin-based material are described, for example, in U.S. Pat. App. Pub. Nos. US 2010/0279112 and US 2010/0279112; U.S. Pat. No. 7,842,780; and WO2004062697, content of all of which is incorporated herein by reference in its entirety.

Figure 8:
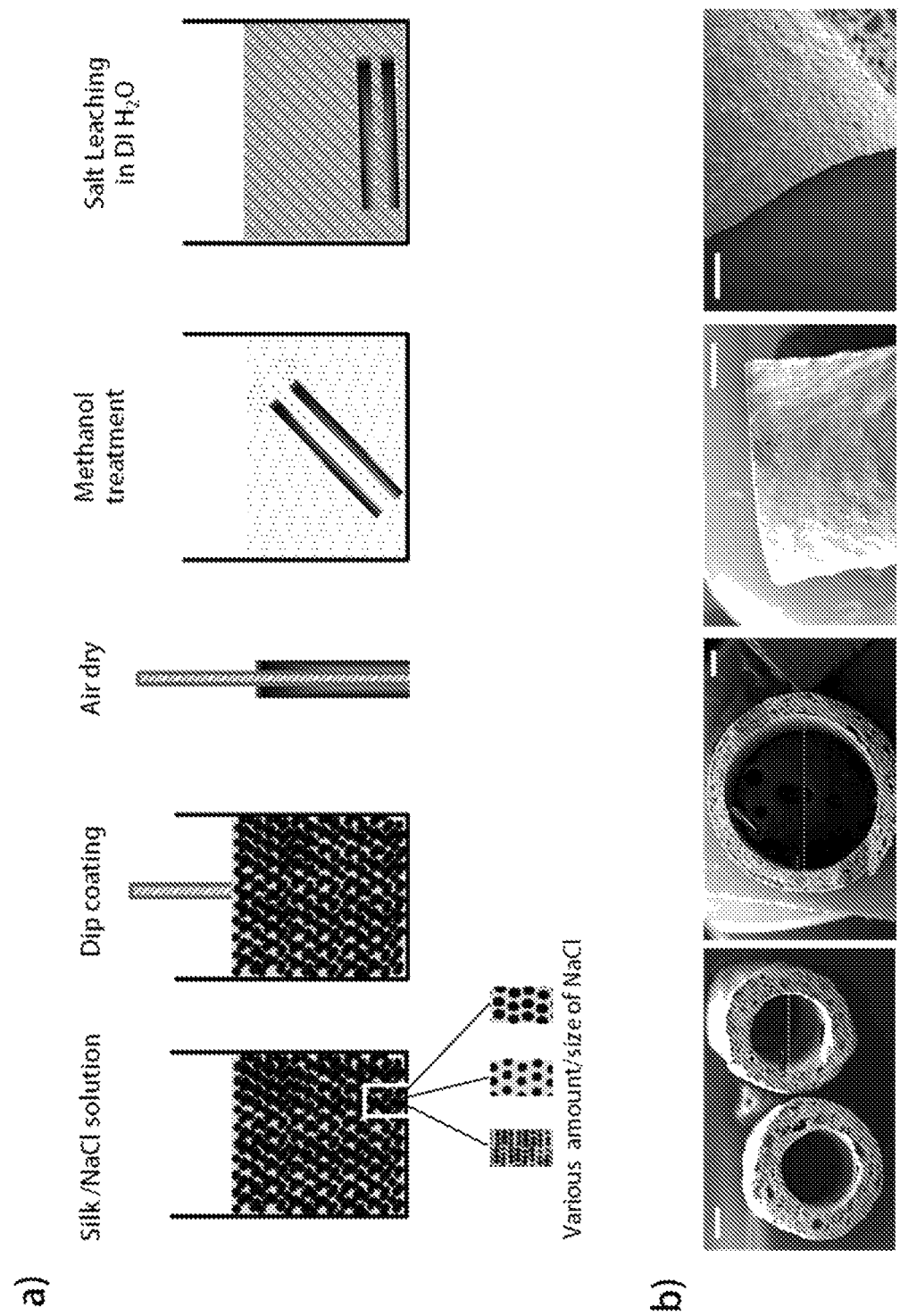
FIG. 8a shows a process flow for silk fibroin/NaCl blending and leaching method that can be used to incorporate nano-porosity into the anastomosis device walls according to some embodiments of the invention.
FIG. 8b shows a scanning electron micrographs (SEM) demonstrate morphology of the final tubes fabricated according to some embodiments of the invention.

FIG. 8A shows an embodiment of the porogen leaching method for forming the pores. As shown, sodium chloride crystals (NaCl) can be suspended in HFIP silk fibroin solution (5% to 20%) with the final concentration of NaCl ranging from <10 mg/ml to >250 mg/ml. The silk fibroin/NaCl blend can be coated onto Teflon rods of various diameters and dried completely. The silk fibroin/NaCl tubes can then be stabilized in 100% methanol for 10 to 20 minutes to induce beta-sheet crystallization of the silk fibroin. NaCl crystals are then leached out in deionized water.

Figure 9:
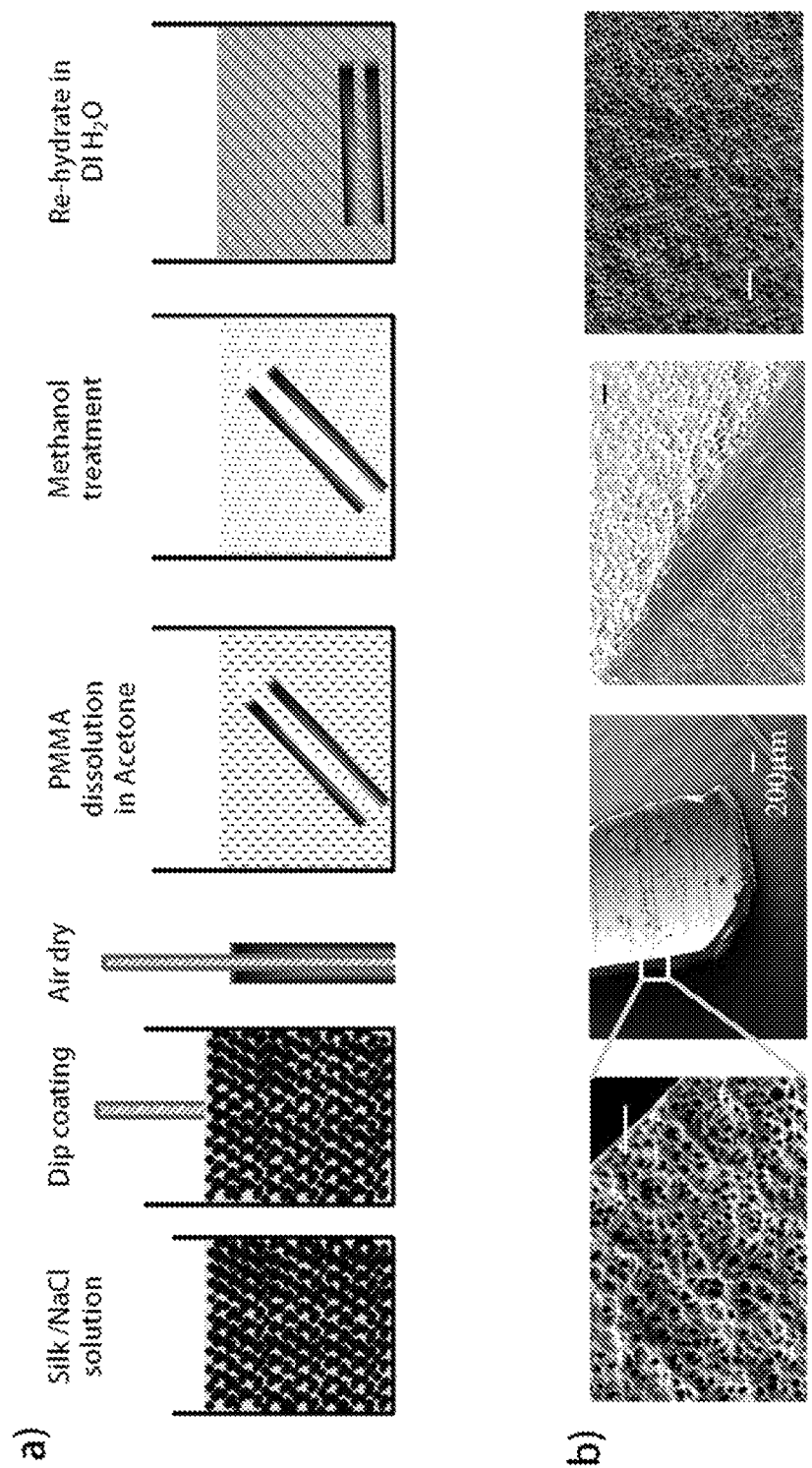
FIG. 9a shows a process flow for silk fibroin/PMMA blending and leaching method used to incorporate nano-porosity into the anastomosis device walls according to some embodiments of the invention.
FIG. 9b shows a SEM of the final material fabricated according to the method shown in FIG. 9a according to some embodiments of the invention.

FIG. 9A shows an embodiment of forming pores using particles as the porogen. As shown, poly(methyl methacrylate) (PMMA) nano-spheres (of various controlled diameters) can be blended with aqueous silk fibroin solution. The nano-spheres are spun down and re-suspended in an aqueous silk fibroin solution. The final concentration of nano-spheres in silk fibroin solution can be 1% or greater. To ensure a porous luminal surface of the device, PMMA spheres suspended in deionized water, can be first coated on to the rod surface followed by a coating of the silk fibroin/PMMA blend. Several layers of the blended solution can then be coated onto the Teflon rods as discussed above and dried. The silk fibroin/PMMA dried tubes are then immersed in acetone solution (50%-100%) to dissolve and leach out the PMMA spheres. The porous silk fibroin tubes can then be stabilized in 100% methanol for 10 to 20 minutes to induce beta-sheet crystallization of the silk fibroin and then re-hydrated in deionized water.

Though not meant to be bound by a theory, a device's porosity, structure, and mechanical properties can be controlled via different post-spinning processes such as vapor annealing, heat treatment, alcohol treatment, air-drying, lyophilization and the like. Additionally, any desirable release rates, profiles or kinetics of a molecule encapsulated in the anastomosis device can be controlled by varying processing parameters, such as anastomosis device thickness, silk fibroin molecular weight, concentration of silk fibroin in the bulk material, beta-sheet conformation structures, silk fibroin II beta-sheet crystallinity, or porosity and pore sizes.

Construction

The cylindrical portion of an anastomosis device can be made using any method known in the art for preparing a cylindrical silk fibroin matrix, e.g., silk fibroin tube. For example, tubes can be made using molding, dipping, electrospinning, gel spinning, and the like. Gel spinning is described in Lovett et al. (Biomaterials, 29(35):4650-4657 (2008)) and the construction of gel-spun silk fibroin tubes is described in PCT application no. PCT/US2009/039870, filed Apr. 8, 2009, content of both of which is incorporated herein by reference in their entirety. Construction of silk fibroin tubes using the dip-coating method is described in PCT application no. PCT/US2008/072742, filed Aug. 11, 2008, content of which is incorporated herein by reference in its entirety. Construction of silk fibroin tubes using the film-spinning method is described in PCT application No. PCT/US2013/030206, filed Mar. 11, 2013 and U.S. Provisional application No. 61/613,185, filed Mar. 20, 2012, content of both of which is incorporated herein by reference.

A number of different methods can be used to fabricate an anastomosis devices and/or components; for example, anastomosis devices can be prepared from bulk material solution using a number of different methods. In some embodiments, after fabrication, these components can be annealed in a humid environment for 6 hours at 80° C., to induce β-sheet formation, increase the mesh crystallinity and thereby improve mesh mechanical properties, resiliency, and water insolubility. Alternatively, following published protocols [3], silk fibroin components can be submerged in 99.9% (w/v) methanol for 5 minutes to induce crystallinity.

The device according to an embodiment of FIG. 1 can be fabricated by coating extruded dextrose rods with HFIP silk fibroin solution. Dextrose is caramelized then brought to a stable temperature of 105° F. Mechanical drawing of sugar rods can be controlled with stepper motors to increase consistency and repeatability. Rods can be fine-drawn to a diameter of 100 to 1000 µm as desired. Dextrose rods can be coated in silk fibroin solubilized in HFIP solution, e.g., 17% silk fibroin (w/v) solution in HFIP. Silk fibroin coating is crystallized via submersion in methanol or water annealing. Dextrose is leached in water, leaving a small diameter hollow silk fibroin tube. These tubes can be removed and sectioned to desired length, and each end can be beveled 45°.

The device according to an embodiment of FIG. 2 can be fabricated by dip-coating Teflon coated stainless steel rods. For example, Teflon coated stainless steel rods (650 to 4500 µm diameter) which increase in diameter by 250 µm can be dipped into aqueous silk fibroin:glycerol solution and allowed to dry producing a tubular film layer of application specific target thickness (e.g., 150 to 300 µm) which can be measured using a micrometer. The spherical tips which facilitate security and sealing of the anastomosis can be produced as compliant silk fibroin beads in a separate step. Beads can be produced on separate rods with diameter equivalent to the OD of the silk fibroin coated rods. Rods can be rotated using a modified lathe to ensure concentric spherical shape. Volumes (5 to 50 µL) of silk fibroin solution can be dispensed using a multichannel pipette onto the rotating rods such that they result in required bead size. Beads can be designed to have an outer diameter equivalent to 125% of the coated tube outer diameter. After depositing the beads on rotating rods, they can be placed in methanol before complete drying into film. This induces crystallization of the silk fibroin solution which leads to gelation into resilient beads which can then be removed and placed at appropriate distances around the coated tubes. They can be fixed in location using silk fibroin solution as an adhesive, and then crystallized by submerging in methanol forming a permanent bond. These tubes can be removed and sectioned to desired length.

The device according to an embodiment of FIG. 3 can be fabricated by separately fabricating a tubular component with microneedles protruding outward at one end and a tubular sheath.

The tubular component tubular component with microneedles protruding outward at one end can be fabricated by coating stainless steel rods (e.g., 650 to 4500 µm diameter) with aqueous silk fibroin solution (e.g., a silk fibroin:glycerol solution) and allowed to dry producing a tubular film layer of desired thickness (e.g., 250 µm) which can be measured using a micrometer. The rows of silk fibroin microneedles can be added in a second step by circumferentially bonding microneedle arrays. The microneedle arrays can be produced by covering an epoxy mold with silk fibroin solution then centrifuging into the mold to remove air. The backing of the microneedle arrays can be coated with a thin layer of aqueous silk fibroin solution (e.g., a silk fibroin:glycerol solution) and then wrapped around the tubular component. The arrays can be temporarily fixed circumferentially using a malleable stainless wire and allowed to dry for a period of time, e.g., for 24 hours. If present, glycerol stabilizes a non-soluble conformation of the silk fibroin protein thereby leaving a permanent non-soluble bond. The tubular sheath component can be fabricated by coating stainless steel rods (equivalent in diameter to the summed diameter of tubular component with microneedles, including the microneedles, with an aqueous silk fibroin solution (e.g., silk fibroin:glycerol solution) and allowed to dry producing a tubular film layer of the desired thickness, e.g. 150 µm, which can be measured using a micrometer.

The device according to an embodiment of FIG. 5 can be fabricated by separately fabricating the three different components of the device. Part 1, a tubular component with several circumferential rows of silk fibroin microneedles protruding outward at each end, can be fabricated by coating stainless steel rods (e.g., 650 to 4500 µm diameter) with an aqueous silk fibroin solution (e.g., a silk fibroin:glycerol solution) and allowed to dry producing a tubular film layer of desired thickness (e.g., 150 to 300 µm thickness), which is measured using a micrometer. These tubes can be removed and sectioned to desired length. The rows of silk fibroin microneedles can be added in a second step by circumferentially bonding microneedle arrays. The microneedle arrays can be produced by covering an epoxy mold with silk fibroin solution then centrifuging into the mold to remove air. The backing of the microneedle arrays can be coated with a thin layer of an aqueous silk fibroin solution (e.g., silk fibroin:glycerol solution) then wrapped around each end of the tubular component. The arrays can be temporarily fixed circumferentially using a malleable stainless wire and allowed to dry for a period of time, e.g., 24 hours. If present in the solution, glycerol stabilizes a non-soluble conformation of the silk fibroin protein thereby leaving a permanent non-soluble bond. Part 2 and Part 3, tubular sheaths, can be fabricated by coating stainless steel rods (equivalent in diameter to the summed diameter of Part 1 including the microneedles) with an aqueous silk fibroin solution (e.g., a silk fibroin:glycerol solution) and allowed to dry producing a tubular film layer of the desired thickness (e.g., 150 µm thickness), which can be measured using a micrometer.

The device according to an embodiment of FIG. 6 can be fabricated by separately fabricating the three different components of the device. Part 1, a tubular with spherical barb tips at each end, can be fabricated by coating stainless steel rods (e.g., 650 to 4500 µm diameter) with an aqueous silk fibroin solution (e.g., a silk fibroin:glycerol solution) and allowed to dry producing a tubular film layer of application specific target thickness (e.g., 150 to 300 µm) which can be measured using a micrometer. The spherical tips which facilitate security and sealing of the anastomosis can be produced as compliant silk fibroin beads in a separate step. Beads can be produced on separate rods with diameter equivalent to the OD of the silk fibroin coated rods. Rods can be rotated using a lathe to ensure concentric spherical shape. Volumes (5 to 50 µL) of silk fibroin solution can be dispensed using a multichannel pipette onto the rotating rods such that they result in required bead size. Beads can be designed to have an outer diameter equivalent to 125% of the coated tube outer diameter. After depositing the beads on rotating rods, they can be placed in methanol before complete drying into film. This induces crystallization of the silk fibroin solution which leads to gelation into resilient beads which can then be removed and placed at appropriate distances around the coated tubes. They can be fixed in location using silk fibroin solution as an adhesive, and then crystallized by submerging in methanol forming a permanent bond. These tubes can be removed and sectioned to desired length. Part 2 and Part 3, the helical sleeves, can be fabricated by coating a helical silicone rod with an aqueous silk fibroin solution (e.g., a silk fibroin:glycerol solution). The rod can be composed of platinum cure silicone rubber measuring a shore hardness of 10 A. The helical geometry can end in a cuff with an inner radius matching the helical amplitude. After the silk fibroin coating has dried, the rod diameter can be reduced by applying tensile stress and the silk fibroin coating can be twisted down and off of the silicone rod. The inner thread flank, of the helical, sheath can progress to the thread root at a curvature matching the exterior of the coupler end bead. The helical sheath can be sectioned in half into two pieces, preserving the cuff on one piece. The sectioned piece without the cuff is Part 2. The sectioned piece with the cuff is Part 3.

Device Properties

An anastomosis device disclosed herein can comprise any desired mechanical stiffness. For example, the anastomosis device can comprise an average mechanical stiffness of about 0.01 kN/m$^2$ to about 100 kN/m$^2$. In some embodiments, the anastomosis device can comprise an average mechanical stiffness of from about 0.05 kN/m$^2$ to about 75 kN/m$^2$, from about 0.1 kN/m$^2$ to about 50 kN/m$^2$, from about 0.25 kN/m$^2$ to about 25 kN/m$^2$, from about 0.5 kN/m$^2$ to about 10 kN/m², or from about 0.75 kN/m² to about 2 kN/m². In one embodiment, the anastomosis device has an average mechanical stiffness of about 1.2 kN/m².

The radial strength of the anastomosis device can also be optimized for any desired application. For example, the anastomosis device can have an average radial strength of from about 100 mmHg to about 1000 mmHg. In some embodiments, the anastomosis device has an average radial strength of from about 75 mmHg to about 750 mmHg, from about 50 mmHg to about 600 mmHg, from about 100 mmHg to about 500 mmHg, from about 150 mmHg to about 450 mmHg, from about 200 mmHg to about 450 mmHg, or from about 250 mmHg to about 350 mmHg. In some embodiments, the anastomosis device has an average radial strength of about 300 mmHg.

Compressive toughness is the capacity of a material to resist fracture when subjected to axially directed pushing forces. By definition, the compressive toughness of a material is the ability to absorb mechanical (or kinetic) energy up to the point of failure. Toughness is measured in units of joules per cubic meter ($Jm^{-3}$) and can be measured as the area under a stress-strain curve. In some embodiments, the anastomosis device has a compressive toughness of about 1 $kJm^{-3}$ to about 20 $kJm^{-3}$ or about 1 $kJm^{-3}$ to about 5 $kJm^{-3}$ at 6% strain as measured by the J-integral method.

Compressive strength is the capacity of a material to withstand axially directed pushing forces. By definition, the compressive strength of a material is that value of uniaxial compressive stress reached when the material fails completely. A stress-strain curve is a graphical representation of the relationship between stress derived from measuring the load applied on the sample (measured in Pascals) and strain derived from measuring the displacement as a result of compression of the sample. The ultimate compressive strength of the material can depend upon the target site of implantation. In some embodiments, the anastomosis device comprise a compressive strength (stress to yield point) of approximately 1 MPa to approximately 10 MPa.

Compressive elastic modulus is the mathematical description of the tendency of a material to be deformed elastically (i.e. non-permanently) when a force is applied to it. The Young's modulus (E) describes tensile elasticity, or the tendency of a material to deform along an axis when opposing forces are applied along that axis; it is defined as the ratio of tensile stress to tensile strain (measured in Pascals) and is otherwise known as a measure of stiffness of the material. The elastic modulus of an object is defined as the slope of the stress-strain curve in the elastic deformation region. The anastomosis device can comprise a compressive elastic modulus of between approximately 1 MPa and approximately 30 MPa at 5% strain.

In some embodiments, the anastomosis device can be bioresorbed after implantation into a subject. As used herein, the term "bioresorbed" or "bioresorption" refers to infiltration of endogenous tissue or cells into an implanted structure, e.g., stent, which permits integration of the implantable structure and tissues, where one or more components of the implanted structure is replaced by new tissue. For example, the anastomosis device can degrade as tissue surrounding the target site remodels or regenerates.

Figure 10:
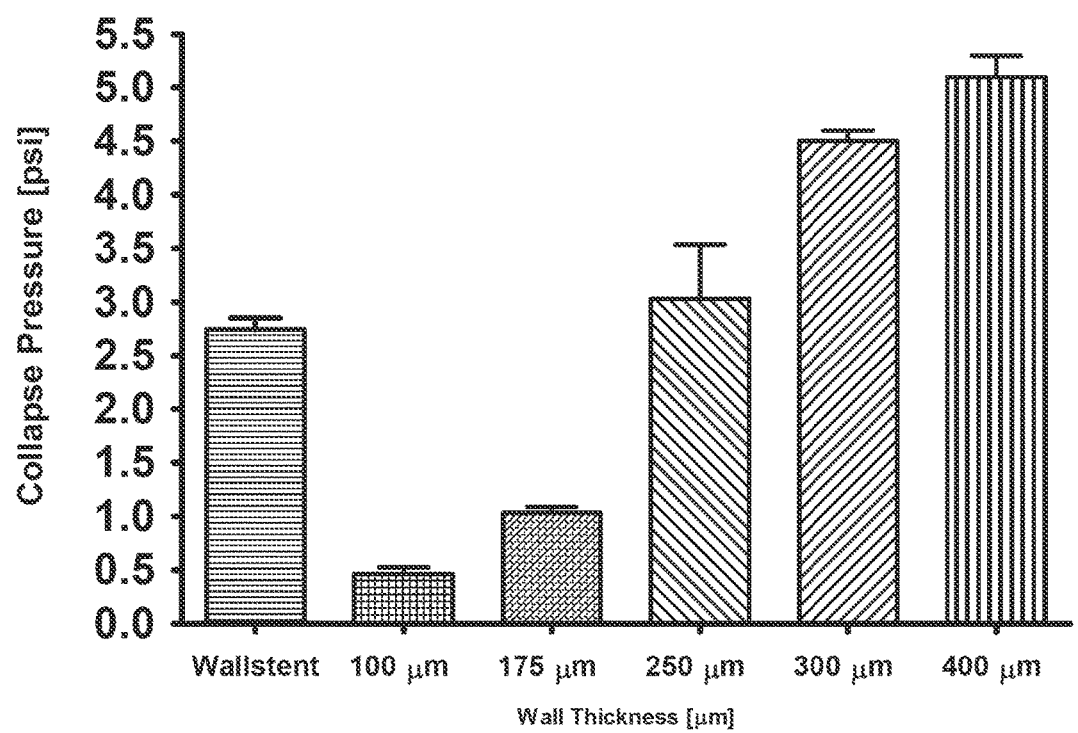
FIG. 10 shows a chart of the radial compressive resistance of the tubular component used in anastomosis device fabricated according to some embodiments of the invention.

Crush resistance of five different implant wall thickness are compared to a clinically available self-expanding metal stent (Boston Scientific Wallstent®) in FIG. 10. As seen, the collapse pressure increased with increasing wall thickness.

Multilayer Devices

In some embodiments, the cylindrical body portion of the anastomosis device can be a multilayered cylindrical body portion. If a multilayered anastomosis device comprises an additive and/or active agent, different layers of the body can comprises same or different additive or active agents. For example, some layers can comprise a first additive (or active agent) and some other layers can comprise a second additive (or active agent). In some embodiments, the outermost layer comprises no active agent. The number of layers in the multilayered cylindrical body portion of the anastomosis device can be any desired number. For example, the multilayered cylindrical body portion of the anastomosis device can comprise from 1 to 100, 1 to 75, 1 to 50, 1 25, or 1 to 20 layers.

Without limitations, thickness of each layer can range independently from nanometers to millimeters. For example, thickness of layer can be 1 nm to 1000 nm, 1 nm to 500 nm, 1 nm to 250 nm, 1 nm to 100 nm, 1 nm to 50 nm, 1 nm to 25 nm, 1 nm to 10 nm, 1 μm to 1000 μm, 1 μm to 500 μm, 1 μm to 250 μm, 1 μm to 100 μm, 1 μm to 50 μm, or 1 μm to 25 μm.

Further all layers can be of the same thickness, all of different thickness, or some of same and some of different thickness.

Particular Embodiments and Features

The anastomosis device designs according to the present invention can also incorporate other features of silk fibroin and silk fibroin based polymers, including the ability to load and deliver therapeutic compounds and up to 100% degradability of the anastomosis device material over time within the body.

In accordance with some embodiments of the invention, the bulk material can include a silk fibroin:glycerol blend in a dry weight ratio of 75:25. The bulk material can be fabricated as described below. Other plasticizers, in addition to or instead of glycerol, can be used. Other weight ratios can also be used.

In accordance with some embodiments, the bulk silk fibroin material can be formed from Cocoons of the silk fibroinworm *Bombyx mori* (supplied by Tajima Shoji Co., Yokohama, Japan). Sodium carbonate, lithium bromide, and Slide-a-Lyzer dialysis cassettes can be purchased from Pierce, Inc. (Rockford, Ill., US). Silk fibroin solutions can be prepared by processing the silk fibroin cocoons. The *B. mori* silk fibroin cocoons can be boiled in 0.02M aqueous $Na_2CO_3$ for 30 minutes to extract the sericin component and isolate the silk fibroin protein. The isolated silk fibroin can then be washed three times for 20 minutes in deionized water and allowed to dry for 48 hours at room temperature. The dried silk fibroin can be dissolved in 93M LiBr at 60° C. for 4 h, and the resulting 20% (w/v) solution can be dialyzed against water using a Slide-a-Lyzer dialysis cassette (molecular weight cutoff 3500) for two days to remove salts. The resulting concentration of aqueous silk fibroin ranged from 5-7% (w/v), which was calculated by weighing the remaining solid after drying. The aqueous silk fibroin solution can be concentrated by exposing the cassette membrane to ambient air for varying times to produce a 10-20% (w/v) silk fibroin aqueous solution. Deionized water can be blended with the silk fibroin solutions to bring concentrations below 5%. The silk fibroin solutions can be stored at 4° C. until use. Aqueous fibroin solution prepared as described above can be used to cast sheet and tubular films as described above. The films can be fabricated by blending aqueous fibroin with 99% (w/v) glycerol to produce blends of 75:25 (dry weight) silk fibroin:glycerol solution.

Other embodiments are within the scope and spirit of the invention. Features implementing functions may also be physically located at various positions, including being distributed such that portions of functions are implemented at different physical locations.

Further, while the description above refers to the invention, the description may include more than one invention.

EXEMPLIFICATION

Example 1

Fabrication of Certain Exemplary Devices

Materials

Cocoons of the silkworm *Bombyx mori* were supplied by Tajima Shoji Co. (Yokohama, Japan). Sodium carbonate, lithium bromide, Slide-a-Lyzer dialysis cassettes were purchased from Pierce, Inc. (Rockford, Ill., US).

Preparation of HFIP Silk Solutions

Silk fibroin solutions were prepared following published procedures [1]. In brief, *B. mori* silk cocoons were boiled in 0.02M aqueous $Na_2CO_3$ for 30 minutes to extract the sericin component and isolate the silk fibroin protein. Isolated silk fibroin was then washed three times for 20 minutes in deionized water and allowed to dry for 48 hours at room temperature. Dried silk was dissolved in 9.3M LiBr at 60° C. for 4 h, and the resulting 20% (w/v) solution was dialyzed against water using a Slide-a-Lyzer dialysis cassette (molecular weight cutoff 3500) for two days to remove salts. The ensuing concentration of aqueous silk fibroin ranged from 5-7% (w/v), which was calculated by weighing the remaining solid after drying. Silk solution was then lyophilized. The lyophilized silk was next dissolved in hexafluoroisopropanol (HFIP) to produce a 17% (w/v) silk solution.

Preparation of Aqueous Silk-Glycerol Solutions

Silk fibroin solutions were prepared following published procedures [1]. In brief, *B. mori* silk cocoons were boiled in 0.02M aqueous $Na_2CO_3$ for 30 minutes to extract the sericin component and isolate the silk fibroin protein. Isolated silk fibroin was then washed three times for 20 minutes in deionized water and allowed to dry for 48 hours at room temperature. Dried silk was dissolved in 9.3M LiBr at 60° C. for 4 h, and the resulting 20% (w/v) solution was dialyzed against water using a Slide-a-Lyzer dialysis cassette (molecular weight cutoff 3500) for two days to remove salts. The ensuing concentration of aqueous silk fibroin ranged from 5-7% (w/v), which was calculated by weighing the remaining solid after drying. This solution was then concentrated by exposing the cassette membrane to ambient air for varying times to produce 10-20% (w/v) silk fibroin aqueous solutions. Deionized water was blended with these silk solutions to bring concentrations below 5%. All silk fibroin solutions were stored at 4° C. until use. Aqueous fibroin solution prepared as described above was used to cast films. Films were fabricated as previously described [2], blending aqueous fibroin with 99% (w/v) glycerol to produce blends of 75:25 (dry weight) silk:glycerol solution.

Controlled Nutrient Exchange

To improve controlled endothelialization and remodeling of the anastomosis device, the wall formulation can modified to incorporate finely tuned nano- or micro-porosities. Nano-porosity in the wall of the vessel anastomosis device can facilitate nutrient, oxygen, and waste exchange improving natural vessel healing. The porosity can be tuned in such a way that a controlled amount of fluid will be diffused to allow this beneficial exchange without harmful loss blood pressure or volume. Two different techniques were developed to incorporate micro- to nano-size pores.

In the first technique, sodium chloride crystals (NaCl) were suspended in HFIP silk solution (5% to 20%) with the final concentration of NaCl ranging from <10 mg/ml to >250 mg/ml. The silk/NaCl blend was coated onto Teflon rods of various diameters and dried completely. The silk/NaCl tubes were then stabilized in 100% methanol for 10 to 20 minutes to induce beta-sheet crystallization of the silk. NaCl crystals were leached out in deionized water.

In the second technique, poly(methyl methacrylate) (PMMA) nano-spheres (of various controlled diameters) were blended with aqueous silk solution. The nano-spheres were spun down and re-suspended in an aqueous silk solution. The final concentration of nano-spheres in silk solution was 1% or greater. To ensure a porous luminal surface of the device, PMMA spheres suspended in deionized water, were first coated on to the rod surface followed by a coating of the silk/PMMA blend. Several layers of the blended solution were then coated onto the Teflon rods as mentioned above and dried. The silk/PMMA dried tubes were then immersed in Acetone solution (100%-50%) to dissolve and leach out the PMMA spheres. The porous silk tubes were then stabilized in 100% methanol for 10 to 20 minutes to induce beta-sheet crystallization of the silk and then re-hydrated in deionized water.

Example 2

Analysis of Certain Exemplary Devices

Prototypes are mechanically evaluated for uniaxial compressive and radial compressive strength. Three samples per group were tested in simulated physiological conditions in PBS at 37° C. Uniaxial compression testing was performed with a uniaxial mechanical tester (model 3366, Instron Inc., Norwood, Mass., US). The implants were positioned between two opposing parallel plates. Compressive force was measured during compression until the implant diameter was reduced to 70%. Radial strength was assessed using a pressure chamber. Implants were fitted in latex sleeves and external pressure was increased until collapse. Collapse pressure was measured in pounds per $inch^2$.

Anastomosis seal was evaluated using a peristaltic pump. Porcine carotid arteries were excised and mounted inline of a pump-driven aqueous flow loop using barb fittings, and secured circumferentially with silk sutures. The arteries were transected and anastomosed using each design for comparison. Flow was increased by 100 $mL \cdot min^{-1}$ each hour until reaching 1600 $mL \cdot min^{-1}$, which is 7 times greater than physiological flow and velocity.

Targeted vessel diameters are clinically evaluated prior to implantation. With this information, anastomosis devices can sized appropriately. Flow studies have found seals perform optimally when the device internal diameter (I.D.) is equal to the loaded I.D. of the blood vessel, and the blood vessel wall is displaced an additional 11.5% by the implant wall. For example, if the vessel I.D. is 2.6 mm, then an appropriately sized device would have an I.D. of 2.6 mm but an outer diameter (O.D.) of 2.9 mm. However, mechanical evaluation has shown the walls of these devices to produce superior strength when at a thickness of 250 to 300 μm. Do to this reason; optimal sizing was reconsidered to incorporate thicker implant walls. After reevaluation, optimal fitting in the blood vessel from the previous example exhibiting a loaded I.D. of 2.6 mm, would now call for a device I.D. of 2.5 mm but an outer diameter (O.D.) of 3 mm, producing an additional 15.5% dilation rather than 11.5%. Preliminary surgical implantations have revealed that certain embodiments, particularly those that use spherical tips as part of the anastomosis mechanism, require reconsideration of the implant dimensions to facilitate the procedure. In certain embodiments where the spherical tip over-dilates the target vessel in the range of 15%, the internal diameter of the implant should be equivalent to 80% of the sphere outer diameter. This facilitates implantation, sealing, and securing of the anastomosis. Preliminary in vitro flow testing of certain anastomosis device designs (e.g. as in FIGS. 3-4 and 6-7), has suggested compression of the load-dilated vessel wall to 90% results in a secure seal.

The silk:glycerol implant material facilities superior drug elution due to broad drug compatibility and aqueous processing which is not possible with other competitive polymer designs that require the use of harsh and toxic solvents. Our fabrication techniques allow for discrete laminar drug loading within the device body as well as surface treatments. This facilitates programmable elution during degradation. Our material is also compatible with most surface functionalization treatments.

Example 3

An Exemplary Sutureless Silk Anastomosis Device: Fabrication Mechanics, and In Vivo Testing The present Example describes certain sutureless silk anastomosis devices designed to reduce surgical time and difficulty, which may lead to less invasive cardiovascular anastomosis. The implant utilizes a barb-and-seat compression fitting composed of one male and two female components. The implant body is resorbable and capable of eluting heparin. Custom controlled extrusion equipment was designed in order to fabricate the implants. The devices were evaluated using crush resistance, retention strength, and leak resistance. Radial crush resistance is in the range of metal vascular implants (3-4 psi). Insertion force and retention strength of the anastomosis was dependent on fit sizing of the male and female components and subsequent vessel wall compression. Anastomotic burst strength was dependent on the amount of vessel wall compression, and capable of maintaining higher than physiological pressures. In initial screening using a porcine implant, the devices functioned for 28 days (the length of study) and histological sections revealed cellular infiltration within the laminar structure of the male component, as well as at the interface between the male and female components. Degradation and absorption of the implant wall were observed. The speed per anastomosis using this new device was much faster than current systems, providing significant clinical improvement.

Introduction

As described herein, manual suturing is the current gold standard for generating vascular anastomoses.[1-4] Reconstitution of blood supply via vessel anastomosis remains a technically challenging and time consuming procedure with a steep learning curve for surgeons. Suturing errors such as uneven spacing, inversion of suture walls, and misalignment of the vessel intima can lead to anastomotic leaks, thrombosis, prolonged hospital stays and death.[5-10] These and other factors have contributed to the persistent failure rates in 2-6% of cases, potential loss of reconstruction, and elevated health care costs.[11,12] There is increasing demand for an easy, time saving, less damaging but reliable procedure to form vascular anastomoses. This is particularly crucial in trauma, cardiac surgery, and organ transplant surgery where patient survival is dependent on clamp time or warm ischemia time.

The present invention encompasses the recognition that, by decreasing the level of technical dexterity required for anastomosis, pathways to less invasive tool and robotic facilitated anastomosis may become available. Furthermore, development of anastomosis devices which do not require highly skilled hands or lengthy surgical times will allow the possibility of temporary peripheral vessel bypass by minimally trained respondents in times of emergency such as direct combat casualty care.

A variety of vascular anastomosis mechanisms and devices have been pursued.[13] Each anastomosis mechanism imparts varying levels of security and implantation difficulty. The average reported anastomosis time for these devices ranges from 14 to 100 minutes and requires use of specialized tools and a high level of dexterity. Devices such as microclips,[14-16] ring staplers,[17-19] and magnets[20-22] have been used to improve sutureless anastomosis but due in part to the use of non-degradable materials have been found to induce chronic trauma to blood vessels after healing is complete.[4,14,16-20,23-30] The permanent nature of these implants raises increasing concerns for growing children or adolescents suffering from congenital disease or traumatic vascular injury.[31,32] Current experimental bioresorbable devices exhibit relatively weak anastomotic pull out strength compared to permanent alternatives.[26]

The present Example describes a fully resorbable, drug-eluting, sutureless anastomosis device for small to large diameter vessels, which can decrease complexity and ischemic time in vascular reconstructive surgical procedures. This device is formed from silk protein and can handle high pressures (2.800 mmHg) and flow rates, and facilitates extremely quick anastomosis procedures (~1 minute) with minimum dexterity. The device simplifies vascular anastomosis by providing a quick and feasible mechanical union without the need for specialized proprietary tools, piercing of vessel tissue, or tying of knots. The components fit concentrically within and around the vessel, which allows the device to align and complete the anastomosis procedure with single sliding motion.

Results and Discussion

Device Fabrication and Anastomosis Strategy

Silk fibroin was used as the structural material to generate the anastomosis devices, due to its strength and degradability. The silk material can also be autoclaved for sterilization without loss of mechanical integrity.[33] Glycerol was used in the material and is a simple metabolizable nontoxic sugar alcohol ubiquitous in food and pharmaceutical industries. When blended, glycerol stabilizes an intermediate conformation of crystallized silk which produces a more flexible yet stable and strong film.[34]

Figure 12:
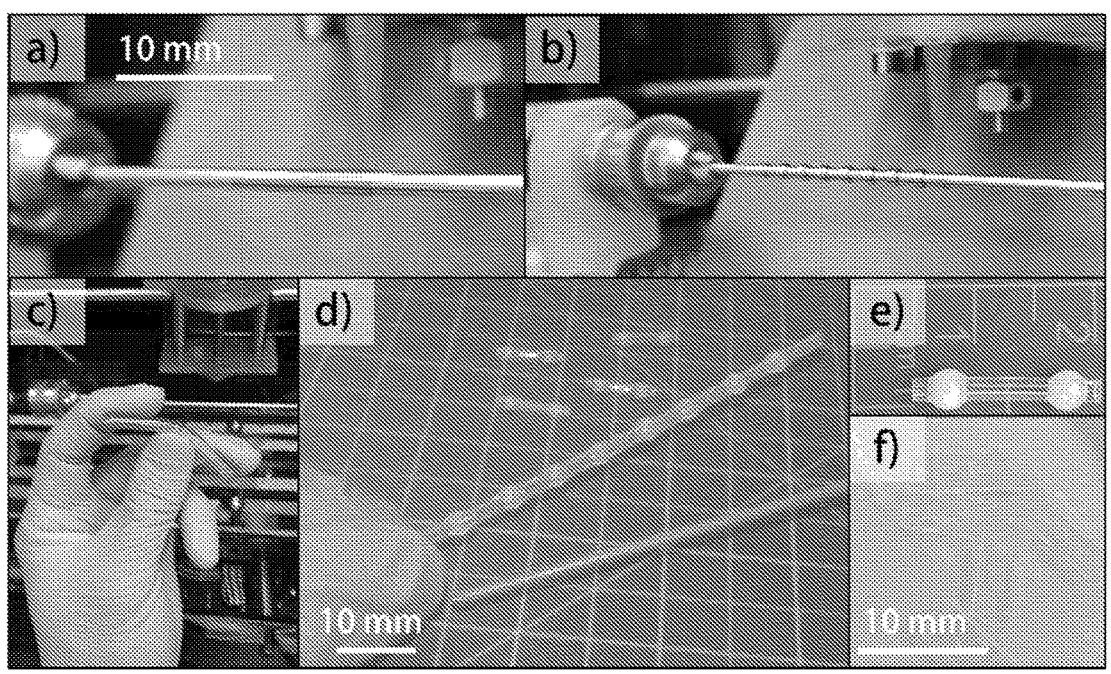
FIG. 12. Process flow of device fabrication: a) Coating of rods for clip and coupler components; b) Spherical barb tip deposition for coupler components; c) Removal of tubes from rods for clip components; d) Removal of tubes with spherical barbs from rods for couplers; e) Initial trimming of coupler components; f) Initial trimming of clip components from tube, and creation of seats using biopsy punch.

A micro-stepped extrusion system was developed to precisely deposit layers of silk glycerol around Teflon-coated stainless steel rods to fabricate the tubular film components (FIG. 12). The silk deposition technique was optimized to provide consistent outcomes and control over the fabrication process.

Figure 13:
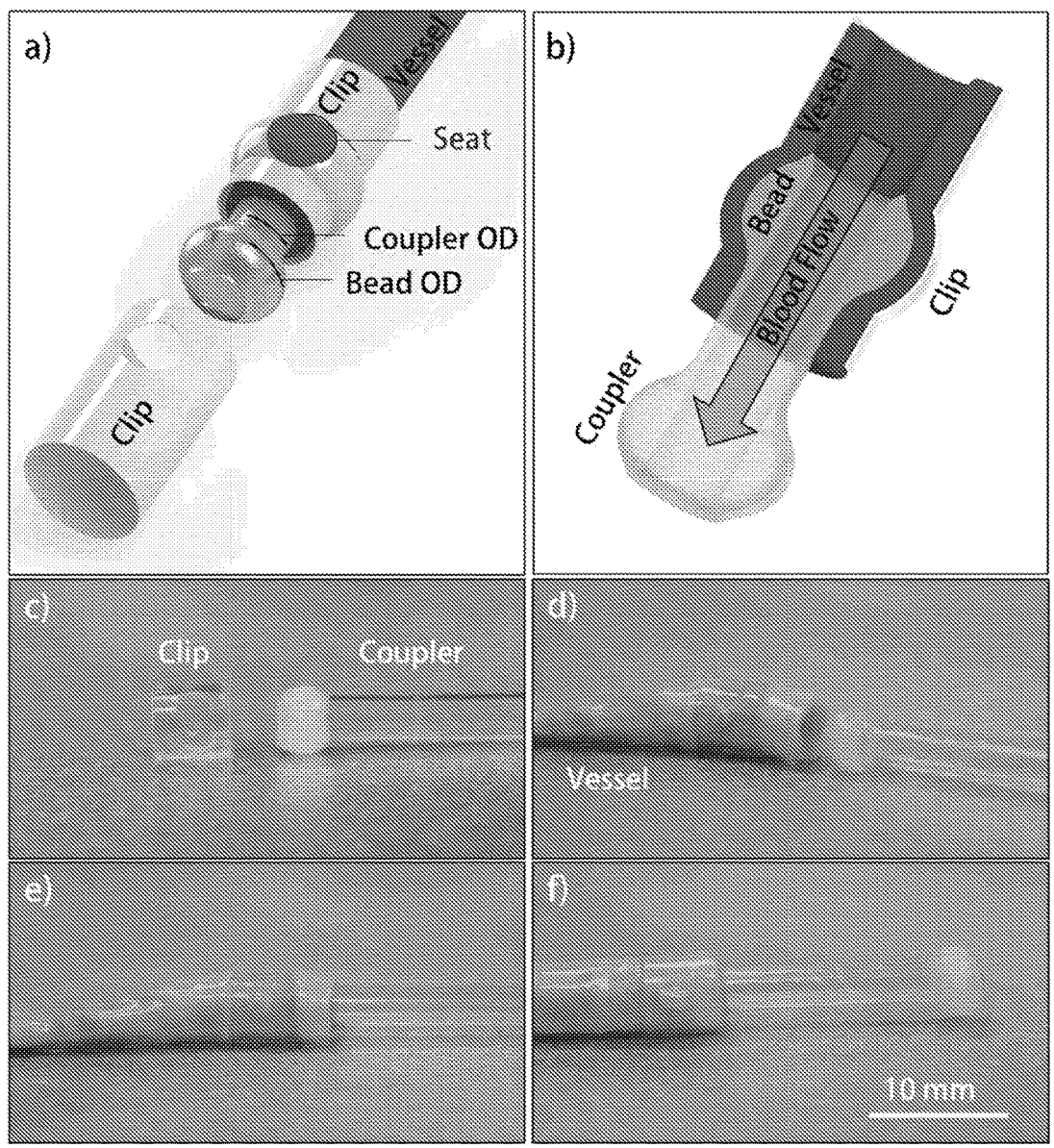
FIGS. 13. (A-F) (a) Schematic of assembled components (b) cross-section view; (c-f) method ofanastomosis, (c, d) first the clip was inserted over the vessel followed by (d, e) inserting the coupler into the vessel. (e, f) Finally, the clip is then slid toward the coupler and locked into place by aligning the seats over around the barbs.

The device was designed based on targeted blood vessel diameters, vessel wall thickness, and swelling ratio of the hydrated device. The anastomosis strategy used three resorbable components; two identical tubular clip sheaths with two opposing holes and the third component is a tubular coupler terminating with ellipsoid barbs at each end. The holes in the clip act as a recessed seat for receiving the barbs of the coupler which subsequently forms the anastomotic mechanical union (FIG. 13). The anastomosed vessels were secured between the coupler and the two clips and upon restoration of blood flow, blood passed from the proximal vessel segment through the lumen of the silk implant and then into the distal vessel segment (FIG. 13*b*). Couplers with an outer diameter of 3 mm (approximately 300 µm wall thickness) were used for in vitro studies to match the luminal diameter of porcine femoral vessels.

Figure 14:
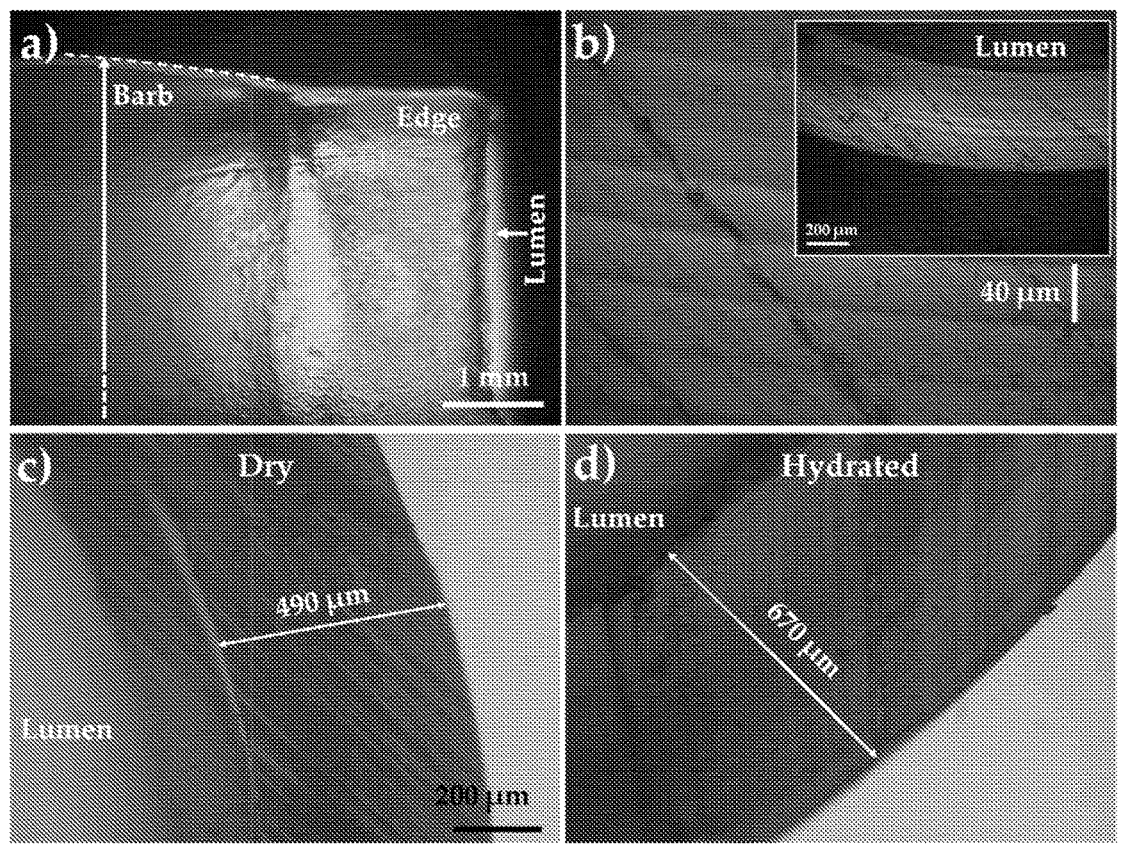
FIG. 14 Phase contrast images of (a) the coupler device barb and edge of the luminal opening; (b) high and low magnification of the hydrated coupler device cross-section showing FIG. 15 Mounting method for (a-b) mechanical testing of compression to insertion; (c) tensile testing procedure; (d) radial compressive resistance of the tubular component used in anastomosis device fabrication. Crush resistance of 5 different implant wall thickness are compared to femoral vein (F.V.) and artery (F.A.) and a clinically available metal self-expanding stent (MSES) (Boston Scientific Wallstent); (e) Effect of 50% vessel wall compression on insertion force and pull-out retention strength.

The implant body produced from silk was stiff in the dry state yet progressively softened when hydrated. This property eases implantation and then allows the implant to exhibit softer properties after implantation, avoiding stress shielding and minimizing the risk of long-term chronic irritation. Unlike tyrosine-derived polycarbonate, salicylate, and magnesium alloys, hydration of this silk material swells slightly after hydration in physiological conditions (FIG. 14).[35] The outer diameter and sidewall thickness of the coupler increased approximately 12% and 30%, respectively, after hydration. This property improved vessel fit and more secure, in contrast to the shrinking observed with polylactic acid implants.[36] The design of this device was limited by the degree of flow resistance due to the thickness of the implant walls. The resistance to fluid flow and pressure change across the implant as a function of wall thickness was estimated by Poiseuille using the equations: $R=8L\eta/\pi r^4$ and $\Delta P=Q8L\eta/\pi r^4$, respectively where R=resistance, L=implant length, η=viscosity, r=the implant luminal radius, ΔP=pressure change and Q=the volumetric flow rate. The resistance and pressure change are inversely proportional to the luminal radius raised to the fourth power, thus a small change in radius has a significant impact. Although the implants are not likely to experience pressures in the peak aortic range of 140 mmHg or 19 kPa, we estimated the affect that this pressure would have on radial displacement using tensile mechanical analysis of the implant material. A stress of 25.6±0.7 kPa resulted in a $2e^{-3}\pm 7e^{-5}$% uniaxial strain, or radial displacement of $3.2e^{-4}$% considering $\Delta r=\Delta x/2\pi$, where Δx is the change in strain. These small radial displacements are not large enough to invalidate the estimations produced using Poiseuille's equation for our purpose. The luminal diameter of the anastomosis device did not deform significantly under physiological pressures, thus we estimated that pressure drop due to the implant was mainly a result of the reduction in luminal cross-sectional area by the sidewalls of the device (Table 1).

TABLE 1

Flow resistance and subsequent pressure drop caused by reduction of the cross-sectional area of the vessel lumen, by the implant walls.

| Vessel Lumen [mm] | Blood Flow [ml/min] | Implant Wall Thickess [µm] | | | | | | |
|---|---|---|---|---|---|---|---|---|
| | | 0 | 100 | 175 | 250 | 300 | 400 | 500 |
| | | Pressure Drop [mmHg] | | | | | | |
| 1 | 200 | 35.7 | 87.1 | 200 | 571 | 1,393 | 22,287 | NA |
| 1.5 | 200 | 7.04 | 12.5 | 20.4 | 35.7 | 54.4 | 149 | 571 |
| 2 | 200 | 2.23 | 3.4 | 4.81 | 7.04 | 9.28 | 17.2 | 35.7 |
| 2.5 | 200 | 0.91 | 1.27 | 1.67 | 2.23 | 2.74 | 4.27 | 7.04 |
| 3 | 50 | 0.11 | 0.15 | 0.18 | 0.23 | 0.27 | 0.38 | 0.56 |
| 3 | 200 | 0.44 | 0.58 | 0.72 | 0.91 | 1.07 | 1.52 | 2.23 |
| 3 | 350 | 0.77 | 1.02 | 1.27 | 1.6 | 1.88 | 2.66 | 3.9 |
| 3.5 | 50 | 0.06 | 0.08 | 0.09 | 0.11 | 0.13 | 0.17 | 0.23 |
| 3.5 | 200 | 0.24 | 0.3 | 0.36 | 0.44 | 0.5 | 0.67 | 0.91 |
| 3.5 | 350 | 0.42 | 0.53 | 0.63 | 0.77 | 0.88 | 1.17 | 1.6 |
| 4 | 50 | 0.03 | 0.04 | 0.05 | 0.06 | 0.07 | 0.09 | 0.11 |
| 4 | 200 | 0.14 | 0.17 | 0.2 | 0.24 | 0.27 | 0.34 | 0.44 |
| 4 | 350 | 0.24 | 0.3 | 0.35 | 0.42 | 0.47 | 0.6 | 0.77 |
| 4.5 | 200 | 0.09 | 0.1 | 0.12 | 0.14 | 0.15 | 0.19 | 0.24 |
| 5 | 200 | 0.06 | 0.07 | 0.08 | 0.09 | 0.1 | 0.11 | 0.14 |

Blood Viscosity of 0.0035 (Pa · s)
Implant length of 1 cm
Systolic Flow of 50 ml/min
Ave Flow of 200 ml/min
Peak Diastolic Flow of 350 ml/min An implant wall thickness of 300 µm produced the maximum radial strength per millimeter of mercury unit pressure drop within the 4 mm vessel model, targeted for in vivo implantation, and produced similar results for smaller caliber vessels. Additionally, the implant wall thickness of 300 µm produced the highest radial strength to flow resistance ratio when estimated for average and peak physiological flows within the vessel model. These results supported the design of a 300 µm implant wall thickness for use in the porcine femoral vein.

Minimizing Technical Difficulty of Anastomosis
Anastomosis Procedure Time

A three-piece design facilitated faster anastomosis times compared to other reported strategies (Table 2). Average reported time to complete double-sided anastomosis via manual suturing was reported in the range of 17 to 55 minutes.[4,17,37] As an alternative to sutures, device manufacturers such as Medtronic and LeMaire, Inc. have developed nitinol (U-clip)[14-16] and titanium (AnastoClip VCS/GC)[28-30] clips which are crimped to anchor vessel ends circumferentially in an interrupted pattern. The average reported time to complete anastomosis for both ends of a vascular graft ranges from 14 to 18 minutes.[14-16,28-30] In contrast to anastomosis clips, manufacturers such as Vascular Therapies and Synovis have developed stapling cartridges (One-shot Vascular Therapies)[25] and ring pin staples (Synovis)[17-19] which use a minimal number of components. These devices complete anastomosis with a single crimping motion but require an intricate loading process which extend the average procedure from 14 to 30 minutes.[17-19,25] The average double sided anastomotic time using the new silk devices was approximately 1 minute.

TABLE 2

Comparison of available anastomosis strategies.

| Device | Anastomosis Mechanism | Time [a] | Materials | Ref |
|---|---|---|---|---|
| Handmade Sutures | Standard interrupted or non-interrupted vessel piercing technique with knots. | 17-55 | Nylon, Polyester, Silk, Catgut, etc. | [4,17,37] |
| Medtronic U-clip | Inserted through vessels similar to sutures trailing a needle. Needle guide is removed, and then each U-clip curls to simulate knots. | 18 | Nitinol | [14-16] |
| Vascular Therapies One-shot | Unique stapling cartridge utilizing six square points. Vessels are loaded and anastomosis is completed using a specialized tool. | 30 | Stainless steel | [25] |
| LeMaire Inc. AnastoClip VCS/GC | Interrupted, vessel wall penetrating or non-penetrating version clips applied with a specialized tool. | 14 | Titanium | [28-30] |
| Synovis Ring Pin Stapler | Blood vessel or graft ends are pulled through then everted onto the pins of the coupler rings. The rings are then compressed with a specialized stapling instrument. | 14 | HIDP-E [b] Stainless Steel Titanium | [17-19] |
| Magnamosis Magnetic Rings | Magnetic rings provide non-piercing compression anastomosis. Rings can be delivered endoluminally. | 100 | NdFeB [c] Teflon | [20-22] |
| Baxter Healthcare Tissucol | Adhesive assists in anastomosis sealing, and reduces time by reducing the number of sutures and knots. | 25 | Fibrin Glue Nylon Sutures | [23] |
| Spiked stent-graft | Stent-graft outer surface contains metal spikes which, when dilated, penetrate the vessel walls to anchor the implant. | 20 | Stainless Steel Teflon | [4] |
| Hooked device | Proximal vessel end must be completely inverted then wrapped around implant and secured on sharp hooks. Distal vessel is next pulled over and secured on hooks. | 11 | PLGC [d] | [26] |
| Silk Coupler and Clip | Non-piercing 3-piece compression fitting | 1 | Silk Fibroin | |

[a] Reported anastomosis time, rounded in minutes, required to anastomose both ends of a vascular graft using this system
[b] High-density polyethylene
[c] Neodymium-iron-boron
[d] Poly(lactide-co-glycolide-co-caprolactone)

Simplified Mechanism and Assembly Feedback

The quick procedure provided by the present device was due to the implementation of novel anastomotic strategies made available through the use of silk. The slide and seat assembly design which allowed the components to concentrically self-align and complete the formation of the concentric seal was dependent on the flexibility and radial strength of the polymer body. Additionally, the assembly provided tactile confirmation of anastomosis in the form of a steep decrease followed by increased insertion resistance, as the coupler barb was positioned into the clip recesses and became fully seated. These qualities reduced technical dexterity requirements during device implantation.

Device Mechanical Properties
Radial Strength

The functional design of the device compression fitting requires radial strength capable of maintaining radial tension at the coupler bead and clip seat interface. Radial crush resistance of the implant within a latex pressure chamber was dependent on wall thickness (FIG. 15d). The maximum crush resistance of 4.48 psi was obtained from the couplers of approximately 300 μm wall thickness, which was nearly 45% higher than self-expanding metallic vascular implants. Further increases in the wall thickness marginally increased the crush pressure but would significantly increase flow resistance.

Assembly Force and Retention Strength

Figure 15:
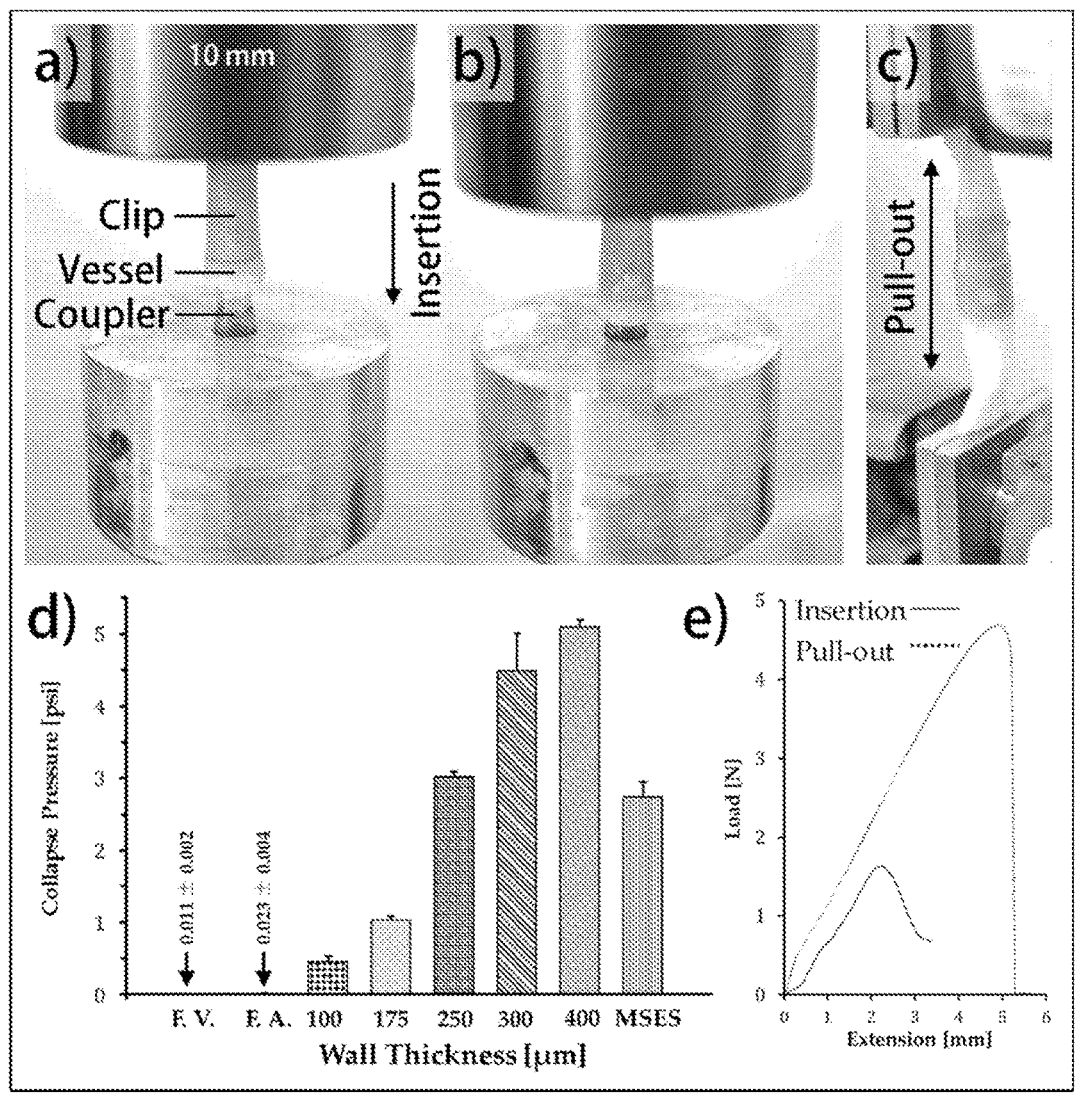

For assembly, the coupler outer diameter was matched to that of each blood vessel lumen, but mated with tubular clips of various internal diameters to achieve various compression strengths. The insertion force and retention strength were dependent on fit sizing of the male and female components and subsequent vessel wall compression (FIG. 15). The fitment pairing mechanically demonstrated the function of the directional barb-and-seat geometry of the implant assembly which was designed to require more force to disassemble compared to initial assembly force. The 90% compressed vessel wall required the highest insertion force and may severely damage the vessel. The 50% vessel compression yielded similar pull-out force compared to 75% compression, however, the insertion force for the later was significantly higher. A full table of insertion force and retention strength per fitment is provided in Table 3.

TABLE 3

Effect of vessel wall compression on insertion force and pull-out retention strength.

| Wall Compression [%] | Insertion Force [N][a] | Retention Strength [N] |
|---|---|---|
| 25 | 0.36 ± 0.21 | 0.48 ± 0.10 |
| 50 | 1.2 ± 0.06 | 4.4 ± 0.49 |
| 75 | 3.9 ± 0.85 | 4.7 ± 0.76 |
| 90 | 3.3 ± 0.48 | 11.6 ± 1.9 |

Peak Pressure Leak Resistance

Figure 16:
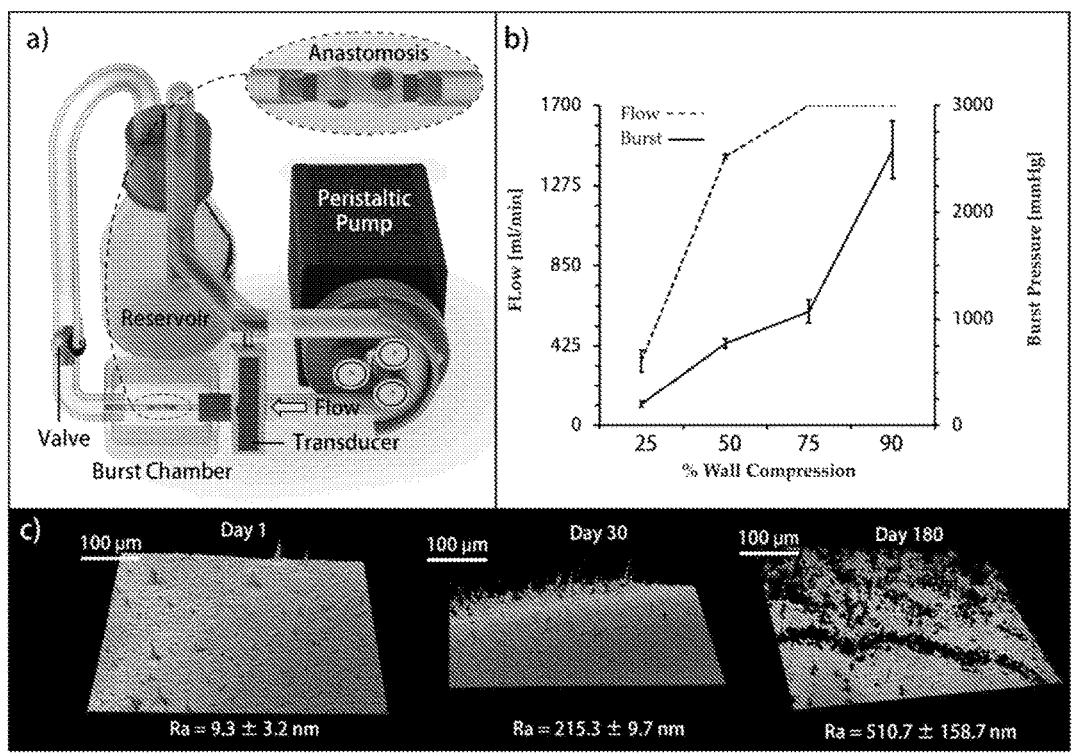
FIGS. 16 (A-C) (a) Bench top flow loop and burst chamber designed for this work; (b) maximum supported flow rate and burst pressure per compression fitting tightness; (c) Interferograms measuring implant luminal surface roughness after 1, 30, and 180 days of aqueous storage.
Figure 17:
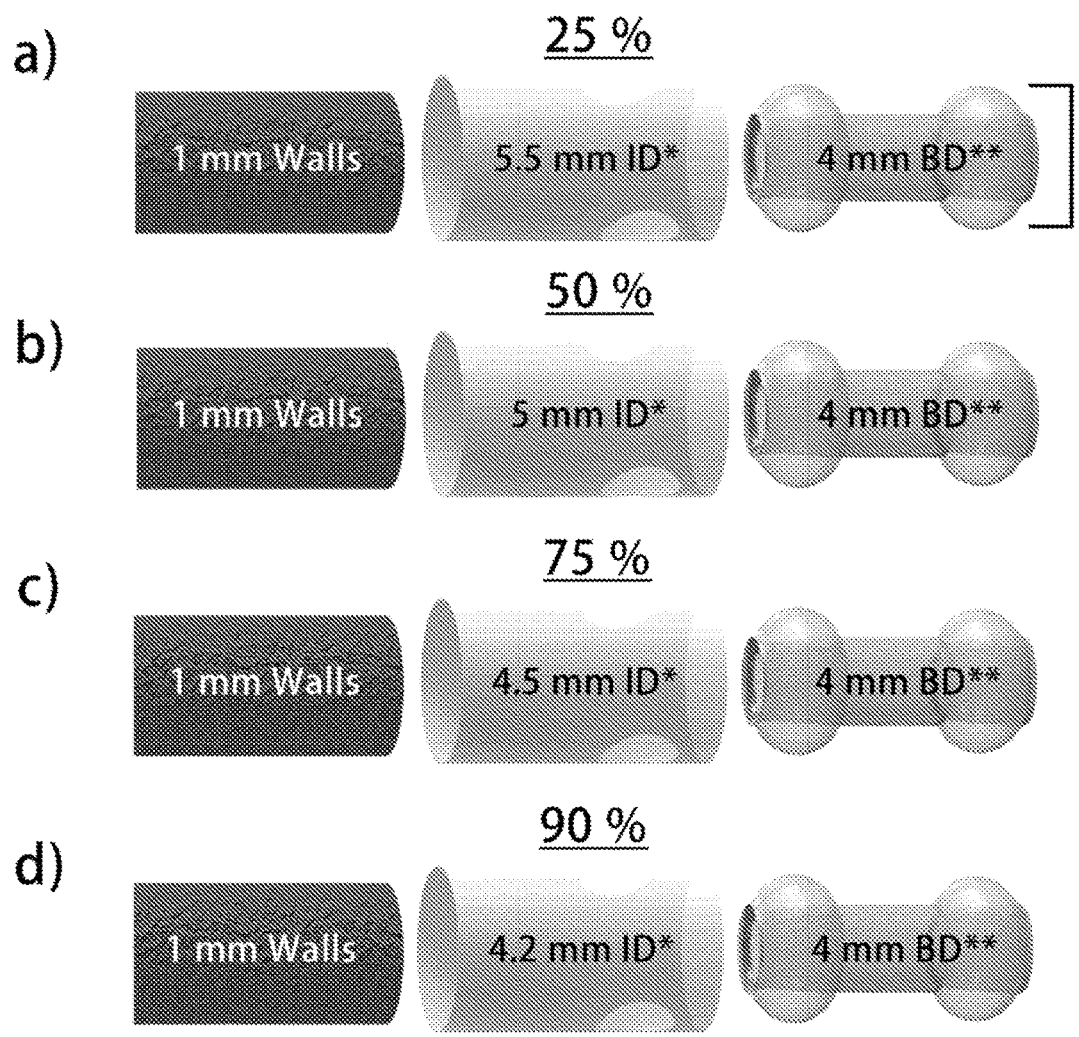
FIGS. 17 (A-D) Schematic comparing the sizes of components used to produce the four fitments which varied in tightness. *ID is the inner diameter of the clip. **BD is the outer diameter of the ellipsoid barb tips.

The stability of the anastomotic seal was also dependent on the percent compression of the vessel wall (FIG. 16). The luminal cross-sectional area of the coupler was not changed in order to preserve consistent flow resistance (FIG. 17). At the lower vessel compression (approximately 25%) the failure occurred due to slippage of the coupler past the seat, while at 50% compression and above the mechanism of failure was tearing of the seat of the external clip. Although all compression settings failed at pressures greater than average physiologically relevant pressure, the 25% compression fitting demonstrated the potential to fail at reported peak physiological pressures.[38,39] A minimum wall compression greater than 25%, such as 50%, would be often recommended to confidently support peak pressures as well as resist failure due to longitudinal strains physiologically relevant to a mobile animal.

Anti-Thrombotic Drug Elution

The erosion of the device progresses from the luminal surface due to direct contact with fluid flow (water or blood). In accordance with the present invention, deposition of multiple layers of silk could be used to entrap various drugs (antiplatelet, antiproliferative) in each layer of the coupler sidewall which would elute as the couplers erode in vivo.

This feature is characteristic of certain silk vascular tubes. The present invention encompasses the recognition that this approach presents a unique opportunity to locally deliver multiple drugs over several time scales to treat a variety of clinical conditions. Furthermore, the present invention encompasses the recognition that the ambient processing conditions of silk facilitate the incorporation of sensitive drugs. This feature provides a clear advantage to using resorbable polymer-based devices over metal-based implants.

Figure 18:
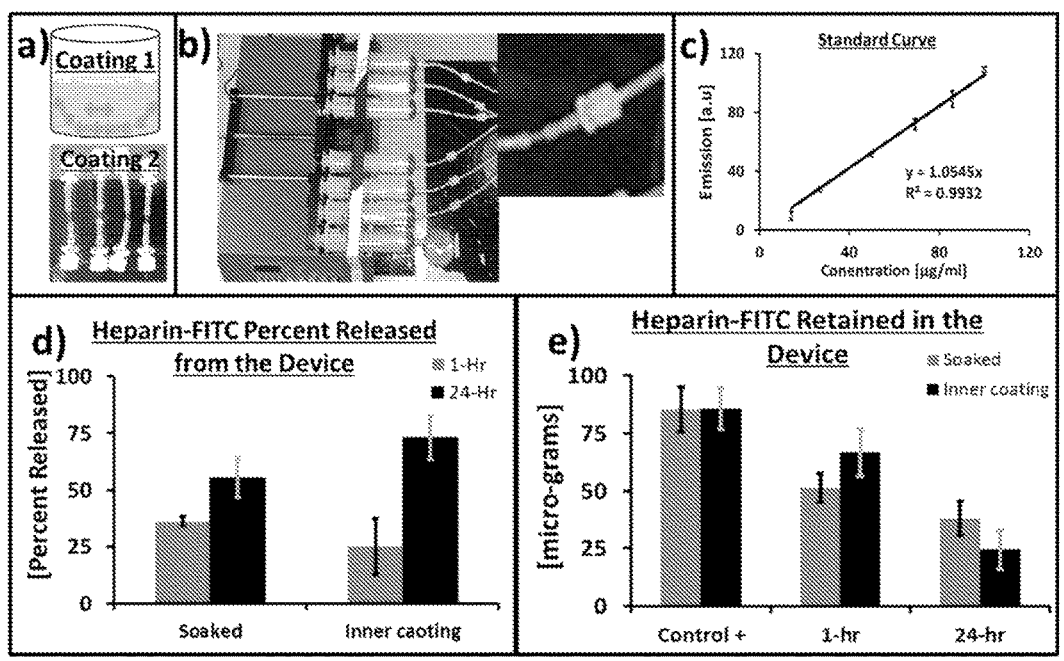
FIGS. 18 (A-E) (a) Schematic describing the procedure of loading devices with Heprain (top) bulk loading via hydration in hepariniized solution (bottom) inner wall coating; (b) perfusion system used to perform the release studies; (c) standard curve; (d) total quantity of Heprain released from the devices over 24 hours time period; (e) amount of remant drug retained in the devices at 0, 1, or 24 hours.

In the present study, we coated the luminal surfaces with heparinized-silk or hydrated the devices with heparinized solution and performed the release kinetics of the same drug for up to 24 hours. The hydrated heparin-loaded devices rapidly released most of the drug, while the dry luminally-coated couplers exhibited delayed release (FIG. 18). This delay in release was likely due to the absorption of the drug during the drying process of the lumen coating. Once the coupler lumen had hydrated during the study the release rate of the remaining drug was similar. By the 24 hour time point, the luminally-coated devices released approximately 20% more heparin than the devices loaded via hydration with heparin solution.

Silk degrades into amino acids over the course of weeks to years with no known bioburdlens.[33,40] In contrast to other common degradable polymers (collagens or polyesters such as PLGA), silk has been reported to be less immunogenic and inflammatory[41,42] and has been reported to be used successfully as implants in small diameter blood vessels in a number of animal studies[40,41,43] and as sutures for decades (FDA approved).

Surface Texture and Storage Life

The resorbable nature of silk has an impact on surface texture which may dictate implant shelf-life and storage strategies. FIG. 16 shows interferograms of the luminal surface of couplers stored in deionized water for up to six months. The average roughness of the as-made device was approximately 10 nm and after six months of storage, the surface roughness was still in sub-micron ranges. Surface roughness can have a large effect on platelet deposition but the roughness of the silk implant body was negligible at the time of initial fabrication, and remained minimal and within the range of current stents at the storage time point of 1 month.[44,45]

Sutureless Resistance to Strains In Vivo

Anastomosis of Porcine Femoral Vein

Figure 19:
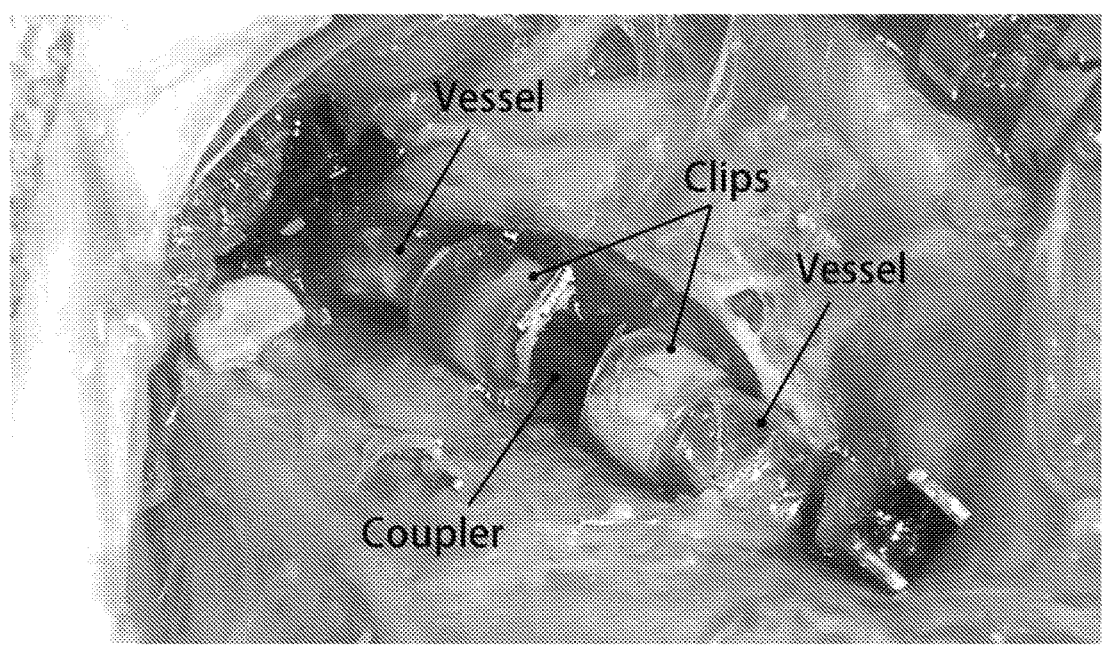
FIG. 19 Digital photograph of the completed anastomosis of a transected porcine femoral vein segments using the sutureless silk device.

Porcine animal models allowed a more accurate design and analysis of implant geometries appropriate for humans, and thus allowed insight into surgical strategies and to the hurdles of human size implantation procedures. The femoral vessels, which span from the knee to groin, are large vessels subjected to significant mechanical strains in mobile animals. These strains are transferred to the anastomosis device and can be a source of failure. The anastomosis device was implanted into a porcine femoral vein and evaluated for mechanical performance related to the sutureless anastomotic seal in vivo for 4 weeks (FIG. 19). The coupler had a wall thickness of 250 µm and the outer diameters of the coupler body and ellipsoid tips measured 3.5 mm and 4.75 mm, respectively, when fully hydrated. The coupler was inserted into a 3.5 to 4.5 mm femoral vein with approximately 600 µm wall thickness. The clips had an inner diameter of 5.15 mm which produced approximately 70.8% compression of the vessel wall. The seat diameters were 3 mm.

Initial implantation of the coupler into the femoral vein was impeded by vessel retraction after transection. The couplers were designed to function with minimal axial length. Anastomoses of the gap, which developed between vessel stumps, required a large amount of axial strain to be applied to the device. However, our design can be fabricated in various lengths to provide dual function as a vascular graft between vessel segments.

Animal Behavior and Mobility

At day 1, 12 hours after surgical anastomosis of the femoral vein, the incisions were intact with minimal swelling and did not exhibit elevated temperatures. Before the 24 hour mark, the animal was ambulatory and capable of weight bearing in both hind legs. The animal could support himself up from seated position without assist and could ambulate steadily, with ten minutes of walking as the limit before sitting. Behavior was otherwise favorable and included taking treats, matt chewing, and socializing with other pigs. Ketofen, Buprenex, and a Fentanyl patch were administered to control pain and subsequent limping. Gabapentin was used to address the potential nerve irritation/inflammation. At day 3 medication was reduced to one dose of Ketophen and limping was no longer observed when the animal was ambulatory and behavior remained favorable. Restored mobility did not compromise the incisions which remained intact and appeared to be healing optimally. At day 10 after surgery there appeared to be seromas under the incisions at the femoral implant sites. A hand-held Doppler ultrasound unit was used to verify flow distal to the graft implant sites to confirm the swellings were not hematomas due to catastrophic leakage from the anastomosis. The swellings soon disappeared within hours without any interventional treatment and all incisions were clear of redness and continued healing.

The main goal was to demonstrate the mechanical integrity of the resorbable sutureless compression anastomosis system. The anastomosis device was implanted in vivo into a porcine femoral vein, without long-term supplementation with antithrombotics or antiproliferatives. The device successfully maintained anastomosis of the vessel for the length of the 28 day study.

Histology

The influence of the device on vascular outcomes at the site of anastomosis was assessed relevant to endothelialization and smooth muscle hyperplasia. Upon excision, the device was found completely covered with new tissue completing the anastomosis.

Histological sections revealed cellular infiltration within the laminar structure of the male component, as well as at the interface between the male and female components (FIG. 20). Histological sections exhibited artifacts in the form of shrinking of the implant walls and separation of neointimal tissue from the implant. However, initial stages of degradation and absorption of the implant wall were also observed. The degree of neointimal tissue was consistent with what was seen for metal and polymeric[46,47] vascular implants, such as stents[47-49] and grafts,[50-52] implanted in the absence of long-term antiproliferative or antithrombotic drug therapies or, in some cases, with delivery of suboptimal therapeutics.[48,49,53,54]

Antiproliferatives, and standard drug therapies were excluded from our initial study to generate an understanding of the baseline occlusion in the absence of commonly administered treatments. Preliminary observations of neointimal tissue development in the absence of drug therapies will provide an understanding necessary to formulating a drug therapy optimized specifically to the device. Hematoxylin and Eosin (H & E) staining of the occlusion developed within the device demonstrated the organization and the presence of recanalization (FIG. 20a). Factor VIII immunohistochemistry demonstrated that the recanalization was lined with endothelial cells (FIG. 20b). Collagen deposition was revealed using Trichrome staining (FIG. 20c). Cells within the occlusion and recanalization were positive for smooth muscle actin suggesting the occlusion was a result of smooth muscle hyperplasia (FIG. 20d). Future drug therapies accompanying the device will likely include everolimus to target hyperplasia in order to compare the present data.

CONCLUSIONS

The majority of vascular anastomotic failures are thought to be due to technical errors as manual suturing demands a high degree of technical skill and dexterity. The present Example describes a mechanically sufficient yet quicker sutureless anastomosis mechanism using resorbable materials capable of drug-elution. The design and material addressed determined advancements and limitations of competitive approaches. The silk material facilitated fabrication without the need for toxic solvents and can be fabricated in a variety of diameters and lengths to support various anastomosis scenarios. The axial retention and burst strength were evaluated, as was the resistance generated by the implant geometry. Anastomoses formed using the device were secure, and supported burst pressures and flow-rates one order of magnitude beyond physiological peaks. The device successfully maintained anastomosis of the femoral vein in vivo for the length of the 28 day study. The robust performance of the compression style seal leaves opportunity for future design improvements favoring flexibility and permeability of the device body. It will be appreciated that provided technologies are applicable to neointimal tissue growth. In some embodiments, provided technologies will include administering antiproliferative and/or antithrombotic therapies, for example according to industry standards.

The speed per anastomosis using the device was one of the fasted reported, and a fraction of the time compared to modern clinically available options. Much of the observed time savings can be attributed to the minimalistic component system with an intuitive self-aligning concentric design, the single circumferentially lined seal, and the positive tactile confirmation of completion. The device has the potential to decrease complexity of procedures, and to minimize ischemia and surgical times, while providing confidence in the anastomotic seal. The design may also support strategies compatible with the use of less invasive catheter or robotic mediated procedures.

EXPERIMENTAL SECTION

Materials

Cocoons of the silkworm *Bombyx mori* were supplied by Tajima Shoji Co. (Yokohama, Japan). Sodium carbonate, lithium bromide, and Glycerol MW 92.09, were purchased from Sigma-Aldrich Corp. (St. Louis, Mo., US). Porcine femoral vessels from 6-9 month old 250 lb. Yorkshire pigs were ordered from Animal Technologies, Inc. (Tyler, Tex., US). Heparin and Fluorescein conjugated Heparin was purchased from Invitrogen Life Technologies (Grand Island, N.Y., US).

Preparation of Aqueous Silk-Glycerol Solutions

Aqueous silk fibroin solutions were prepared following published procedures.[55] Aqueous fibroin solutions were blended with 99% (w/v) glycerol, as previously described,[34] to produce blends of 80:20 (dry weight) silk:glycerol solution.

Fabrication of Device Components

The anastomosis device design was composed of two parts as described in FIG. 12. Part 1 was an intraluminal coupler, which was a cylindrical tube with spherical barb tips at each end. The tubular component of the coupler was fabricated by coating aqueous silk:glycerol (20% dry wt. glycerol) solution on to the Teflon coated stainless steel rods (0.65 to 6 mm diameter) using a microstep controlled extruder and lathe (FIG. 12a). The coating was allowed to dry and each coating produced a 40 µm thick tubular film layer (FIG. 14) and subsequent layers were deposited to achieve the target (150 to 300 µm) thickness. Lower concentrations of silk:glycerol can be used to generate thinner layers. The ellipsoid barb tips were produced in a separate step by dispensing 5 to 50 µl of silk:glycerol solution onto the previously coated rods. The final outer diameter of the barbs were equivalent to approximately 125% of the outer diameter of the coated rods (FIG. 12b). Part 2 (FIG. 12f) was a tubular sheath clip fabricated by same technique to achieve thickness of 250 µm. Two or more opposing holes were excised from the sheath using a biopsy punch to form a recess seat. The holes were sized according the dimensions of the ellipsoid tip to be received.

Surface Analysis

A scanning white-light interferometer (New View 600, Zygo Co., Middlefield, Conn., US) was used to measure topography, and profile. A 10× interferometric objective was used to scan the film in the Z-axis 5 µm below and above the surface plane to produce a 3D interferogram. Roughness ($R_a$) was measured along a 500 µm linear section on the luminal surface of 5 implants per time point (1, 30, or 180 days storage in sterile DI $H_2O$). $R_a$ was expressed as $R_a = 1/n\Sigma_{i=1}^{n}|\gamma_i|$ where $\gamma_i$ is the difference in height between any measured point and the calculated mean sample height.

Swelling of Components

Five devices with 6 mm outer diameter were subjected to dehydration for seven days at ambient conditions, then rehydration in deionized water for 24 hours. Changes in diameter and wall thickness were measured using cylindrical class ZZ plug gauges (model 102100200, Vermont gauge, Swanton, Vt., US) and an electronic micrometer (model 293-831, Mitutoyo Corp., Aurora, Ill., US).

Mechanical Analysis

The coupler-vessel insertion force and anastomotic pull-out force was measured using uniaxial mechanical tester (model 3366, Instron Inc., Norwood, Mass., US). Insertion and pull-out tests were performed in triplicate at room temperature and repeated using four different assembly fitments which ranged in tightness. Tightness was measured as the amount of vessel wall compression produced between the outer diameter of the spherical bead tip of the coupler, and the inner diameter of the clip lumen. The four ranges were assembly fitments producing 25%, 50%, 75%, or 90% compression of the blood vessel wall (FIG. 17). Forces were measured in Newtons. In the insertion force test the anastomosis clip over cadaver vessel segments was concentrically aligned over the fixed coupler and the construct was compressed in between two parallel plates in line with the load cell (FIG. 15). The construct was compressed at a rate of 1 mm/min until the holes of tubular sleeve received the spherical barbs of the coupler thereby completing the assembly procedure (FIG. 15B). Pull-out force was measured by pulling the proximal and distal anastomosed vessel segments in opposing directions (FIG. 15C). Radial strength was assessed using a pressure chamber. A coupler was placed within a sealed latex sleeve. The external pressure was increased in steps until coupler collapse. Collapse pressure was measured in pounds per inch2.

Analysis of Anastomotic Seal

Anastomotic seal was evaluated using a peristaltic pump and polyethylene terephthalate (PET) tubing. Anastomosis was performed as mentioned above by securing couplers into the proximal and distal ends of the vessel segment and free end of each coupler was tightly fit into PET tubing to close the flow loop (FIG. 16a). Phosphate buffered saline was flowed through the flow loop with an increased in flow rate by 4 mL·min$^{-1}$ each second until anastomotic failure was reached. A butterfly valve placed inline distal to the anastomosis to restrict the flow and to increase the line pressure until anastomotic failure was reached. Experiments were performed in triplicate.

Heparin Release Kinetics

Coupler devices were soaked in fluorescein conjugated heparin solution (0.5 mg/ml in deionized water) using two different techniques. Either the luminal surface of the couplers were coated with fluorescein conjugated heparin solution or the coupler devices were completely submerged into the solution for 24 hours (FIG. 18a). After equilibration for 24 hours, the couplers were rinsed with deionized water and secured between two segments of silicon tubing mounted in line with a standard perfusion system to mimic dynamic flow conditions for drug release (FIG. 18b). The devices were perfused at a rate of 2 ml/min for 1 hour and 1 ml/hr for 24 hours using deionized water. The perfused silk couplers were removed from the perfusion system and then dissolved in lithium bromide solution to quantify the remnant drug. The dissolved samples and standards (known amount of fluorescein conjugated heparin in silk/lithium bromide solution) were measured (at 495 nm excitation and 515 nm emission) using a plate reader (Molecular Device, LLC, model: SpectraMax M12, Sunnyvale, Calif.) and plotted in micro-grams. The error bars represent the standard deviation and n=5 per condition and time point.

In Vivo Implantation

Implantations were conducted according to the recommendations of IACUC at an approved DLAM facility. The surgical procedures were performed according to our IACUC approved protocol (B2012-130 A-4). Surgeries were performed on a 30 kg male Yorkshire pig. Telazol mixture (Telazol, 8 mg/kg+Ketamine, 4 mg/kg+Xylazine, 4 mg/kg) was administered as a pre-anesthetic. Sedation was supplemented via Isoflurane gas mask at 3-4%. The vascular site was prepped and draped in a sterile manner after an adequate anesthetic plane is obtained. A 6-8 cm incision from the inguinal region down the medial aspect of the hind leg was performed to access the common femoral vein. The vascular bundle was identified as it entered the quadriceps musculature. Proximal and distal control was obtained with application of vascular clamps. The femoral vein was transected and the lumens were then flushed with dilute heparinized saline. Anastomosis was performed as described previously in FIG. 13 (see also FIG. 21). Upon removal of clamps (first distal then proximal) and restoration of blood flow, blood passes from the proximal vessel segment through the lumen of the silk implant then into the distal vessel segment. No sutures were used to assist anastomosis. The incision was then closed in layers with 4-0 Monocryl deep dermal and subcuticular sutures.

Implanted Device Retrieval

At the terminal time point of 4 weeks the pig had grown to 70 kg. The animal was anesthetized as mentioned above and a 6-8 cm incision from the inguinal region down the medial aspect of the hind leg was made to access and excise the region of the femoral vein which contained the implanted anastomosis device. Both proximal and distal control of the vein was obtained with application of vascular clamps. We first transected the segment of the vessel distal to the implant to observe for bleeding (i.e. perfusion) and thus ensure patency. The distal segment was then clamped. Next, the segment of the vessel proximal to the implant was clamped and transected to enable removal the implant while inducing temporary ischemia. The implant and vessel construct was then be prepped for histological analysis and stored in formalin. The wounds were left open. Euthasol IV (Pentobarbital 390 mg/Phenytoin 50 mg), at 0.22 mL/kg, was administered intravenously immediately following these procedures.

Histological Staining

The retrieved segment of vessel and coupler was cross-sectioned transversely such that each section consists of concentric layers of: scar-implant-vein-implant-scar. The vein/implant construct was bisected for embedding in paraffin. After embedding was complete, the blocks were further sectioned from the proximal to the distal end to produce six cross-section slides every 2 mm. The sections received one of six treatments, three of which were stained with H&E, trichrome, or Verhoeffs Elastic Stain. The remaining three were treated for immunohistochemistry (IHC). The IHC treatments were Factor VIII, CD31, or Smooth Muscle Actin.

EXAMPLES REFERENCES

[1] E. L Chang, M. G. Galvez, J. P. Glotzbach, C. D. Hamou, S. El-ftesi, C. T. Rappleye, K.-M. Sommer, J. Rajadas, O. J. Abilez, G. G. Fuller, M. T. Longaker, G. C. Gutner, *Nat. Med.* 2011, 17, 1147.

[2] J. G. Motwani, E. J. Topol, *Circulation* 199, 97, 916.

[3] S. M. Schwartz, D. deBlois, E. R. M. O'Brien, *Circ. Res.* 1995, 77, 445.

[4] S. Abou Tasm, J.-F. Garbé, M. Boufi, J.-P. Bossavy, J.-B. Ricco, *J. Vasc. Surg.* 2012, 55, 210.

[5] A. E. Beris, M. G. Lykissas, A. V Korompilias, G. I. Mitsionis, M. D. Vekris, I. P. Kostas-Agnantis, *Arch. Orthop. Trauma Surg.* 201, 130, 1141.

[6] F. M. Ameli, J. L. Provan, C. Williamson, P. M. Keuchler, *J. Cardiovasc. Surg. (Torino)*, n.d., 28, 695.

[7] M. Ojha, R. L. Leask, K. W. Johnston, T. E. David, J. Butany, *Ann. Thorac. Surg.* 2000, 70, 1338.

[8] M. D. Mary E. Charlson, M. D. O. Wayne Isom, *N. Engl. J. Med.* 2003, 348, 1456.

[9] B. N. French, N. B. Rewcastle, *Stroke* 1977, 8, 597.

[10] T. Zubilewicz, J. Wronski, A. Bouriez, P. Terlecki, A. M. Guinault, B. Muscatelli-Groux, J. Michalak, D. Méllière, J. P. Becquemin, E. Allaire, *Med. Sci. Monit.* 2001, 7, 316.

[11] J. J. Disa, P. G. Cordeiro, D. A. Hidalgo, *Plast. Reconstr. Surg.* 1999, 104, 97.

[12] D. T. Bui, P. G. Cordeiro, Q.-Y. Hu, J. J. Disa, A. Pusic, B. J. Mehrara, *Plast. Reconstr. Surg.* 2007, 119, 2092.

[13] G. Pratt, W. Rozen, A. Westwood, A. Hancock, D. Chubb, M. W. Ashton, I. S. Whitaker, *Microsurgery* 2012, 32, 68.

[14] R. C. Baynosa, R. Stutman, R. C. Mahabir, W. A. Zamboni, K. T. Khiabani, *J. Reconstr. Microsurg.* 2008, 1, 39.

[15] J. Taylor, R. Katz, N. Singh, *Microsurgery* 2006, 26, 550.

[16] A. K. Bigdeli, I. Kaczmnaek, S. Eifett, A. Beirs-Fernandez, S. Kober, K. Nikolaou, M. Oberhoffer, C. Vicol, *Eur. J. Cardiothorac. Surg.* 2011, 40, e93.

[17] W. M. Rozen, I. S. Whitaker, R. Acosta, *Anticancer Res.* 2010, 30, 1293.

[18] I. Ducic, B. J. Brown, S. S. Rao, *Microsurgery* 2011, 31, 360.

[19] G. Ye, H.-G. Mo, Z.-H. Wang, S.-H. Yi, X.-W. Wang, Y.-F. Zhang, *J. Urol.* 2006, 175, 636.

[20] D. Erdmann, R. Sweis, C. Heitmann, K. Yasui, K. C. Olbrich, L. S. Levin, a A. Sharkawy, B. Klitzman, *J. Vasc. Surg.* 2064, 40, 505.

[21] R. Jamshidi, J. T. Stephenson, J. G. Clay, K. O. Pichakron, M. R. Harrison, *J. Pediatr. Surg.* 2009, 44, 222.

[22] J. Wall, M. Diana, M. Leroy, V. Derujiter, K. D. Gonzales, V. Lindner, M. Harrison, J. Marescaux, *Endoscopy* 2013, 45, 643.

[23] A. B. Cho, T. H. Wei, L. R. Torres, R. M. Júnior, G. M. Rugiero, M. A. Aita, *Microsurgery* 2669, 29, 24.

[24] L. Wiklund, L. F. Bonilla, E. Berglin, *J. Thorac. Cardiovasc. Surg.* 2005, 129, 146.

[25] L. Liu, J. Liu, M. Zhu, S. Hu, *Ann. Thorac. Surg.* 2006, 82, 303.

[26] K. Ueda, T. Mukai, S. Ichinose, Y. Koyama, K. Takakuda, *Microsurgery* 2010, 30, 494.

[27] M. Taylor, L. Bumanlag, . . . *Am. Leather . . .* 2009, 104, 79.

[28] C. J. Zeebregts, W. M. Kirsch, J. J. van den Dungen, Y. H. Zhu, R. van Schilfgaarde, *Am. J. Surg.* 2064, 187, 751.

[29] C. J. Zeebregts, *Br. J. Surg.* 2005, 92, 654.

[30] P. Aarnio, O. Järvinen, P. Varjo, *Int. J. Angiol.* 2000, 9, 62.

[31] B. H. Goldstein, R. Hirsch, M. E. Zussman, J. a Vincent, A. J. Torres, J. Coulson, R. E. Ringel, R. H. Beekman, *Am. J. Cardiol.* 2012, DOI 10.1016/j.amjcard.2012.06.063.

[32] I. Gonzalez, D. Kenny, S. Slyder, Z. M. Hijazi, *Pediatr. Cardiol.* 2012, DOI 10.1007/s00246-012-0439-9.

[33] G. H. Altman, F. Diaz, C. Jakuba, T. Calabro, R. L. Horan, J. Chen, H. Lu, J. Richmond, D. L. Kaplan, *Biomalerials* 2003, 24, 401.

[34] S. Lu, X. Wang, Q. Lu, X. Zhang, J. a Kluge, N. Uppal, F. Omeneto, D. L. Kaplan, *Biomacromolecules* 2010, 11, 143.

[35] B. D. Lawrence, S. Wharram, J. a Kluge, G. G. Leisk, F. G. Omenetto, M. I. Rosenblatt, D. L. Kaplan, *Macromol. Biosci.* 2010, 10, 393.

[36] J. a Ormiston, P. W. S. Serruys, *Circ. Cardiovasc. Interv.* 2009, 2, 255.

[37] M. S. Alghoul, C. R. Gordon, R. Yetman, G. M. Buncke, M. Siemionow, A. M. Afifi, W. K. Moon, *Microsurgery* 2011, 31, 72.

[38] C. Stick, U. Hiedl, E. Witzleb, *Eur. J. Appl. Physiol. Occup. Physiol.* 1993, 66, 434.

[39] H. P. von Schroeder, R. D. Coutts, E. Billings, M. T. Mai, M. Aratow, *Clin. Orthop. Relat. Res.* 1991, 218.

[40] X. Wang, X. Zhang, J. Castellot, I. Herman, M. Iafrati, D. L. Kaplan, *Biomaterials* 2008, 29, 894.

[41] B. Panilaitis, G. H. Altman, J. Chen, H.-J. Jin, V. Karageorgiou, D. L. Kaplan, *Biomaterials* 2003, 24, 3079.

[42] L. Meinel, S. Hofmann, V. Karageorgiou, C. Kirker-Head, J. McCool, G. Gronowicz, L. Zichner, R. Langer, G. Vunjak-Novakovic, D. L. Kaplan, *Biomaterials* 2005, 26, 147.

[43] F. Huang, L. Sun, J. Zheng, *Artif. Organs* 2008, 32, 932.

[44] J. Linneweber, P. M. Dohmen, U. Kertzscher, U. Kerzscher, K. Affeld, Y. Nosé, W. Konertz, *Artif. Organs* 2007, 31, 345.

[45] A. Dibra, A. Kastrati, J. Mehilli, J. Pache, R. von Oepen, J. Dirschinger, A. Schömig, *Catheter. Cardoivasc. Interv. Off. J. Soc. Card. Angiogr. Interv.* 2005, 65, 374.

[46] W. J. van der Giessen, a M. Lincoff, R. S. Schwartz, H. M. van Beusekom, P. W. Serruys, D. R. Holmes, S. G. Ellis, E. J. Topol, *Circulation* 1996, 94, 1690.

[47] C. Macaya, *Vasc. Health Risk Manag.* 2012, 8, 125.

[48] M. Hamilos, J. Sarma, M. Ostojic, T. Cuisset, G. Sarno, N. Melikian, A. Ntalianis, O. Muller, E. Barbato, B. Beleslin, D. Sagic, B. De Bruyne, J. Bartunek, W. Wijns, *Circ. Cardiovasc. Interv.* 2008, 1, 193.

[49] T. Palmerini, G. Biondi-Zoccai, D. Della Riva, C. Stettler, D. Sangiorgi, F. D'Ascenzo, T. Kimura, C. Briguori, M. Sabatè, H.-S. Kim, A. De Waha, E. Kedhi, P. C. Smits, C. Kaiser, G. Sardella, A. Marullo, A. J. Kirtane, M. B. Leon, G. W. Stone, *Lancet* 2012, 379, 1393.

[50] V. Mickley, *Nephrol. Dial. Transplant.* 2004, 19, 309.

[51] V. Farooq, P. W. Serruys, Y. Zhang, M. Mack, E. Ståhle, D. Rholmes, T. Feldman, M.-C. Morice, A. Colombo, C. V Bourantas, T. de Vries, M.-A. Morel, K. Ddawkins. A. Kappetein, F. W. Mohr, *J. Am. Coll. Cardiol.* 2013, DOI 10.1016/j.jacc.2013.07.106.

[52] N. Vasić, L. Davidović, D. Marković, M. Sladojević, *Vojosanit. Pregl.* 2013, 70, 740.

[53] M. M. Wong, B. Winkler, E. Karamariti, X. Wang, B. Yu, R. Simpson, T. Chen, A. Margariti, Q. Xu, *Arterioscler. Thromb. Vasc. Biol.* 2013, 33, 2397.

[54] T. Tada, K. Kadota, S. Kubo, M. Ozaki, M. Yoshino, K. Miyake, H. Eguchi, N. Ohashi, Y. Hayakawa, N. Saito, S. Otsuru, D. Hasegawa, Y. Shigemoto, S. Habera, H. Tanaka, Y. Fuku, N. Oka, H. Kato, H. Yamamoto, T. Goto, K. Mitsudo, *Circulation* 2011, 124: A1491.

[55] M. L. Lovett, C. Cannizaro, L. Daheron, B. Messmer, *Biomaterials* 2007, 28, 5271.

REFERENCES

1. Lovett M L, Cannizzaro C, Daheron L. Messmer B. Silk fibroin microtubes for blood vessel engineering. Biomaterials. 2007; 28(35):5271-9.
2. Lu S, Wang X, Lu Q, Zhang X, Kluge J a, Uppal N, et al. Insoluble and flexible silk films containing glycerol. Biomacromolecules. 2010 Jan. 11; 11(1):143-50.
3. Zhang X, Wang X, Keshav V, Wang X, Johanas J T, Leisk G G, t al. Dynamic culture conditions to generate silk-based tissue-engineered vascular grafts. Biomaterials. 2009 July; 30(19):3213-23.
4. Chang E l, Galvez M G, Glotzbach J P, Hamou C D, El-ftesi S, Rappleye C T, et al. Vascular anastomosis using controlled phase transitions in poloxamer gels. Nature medicine. 2011 September; 17(9): 1147-52.
5. Motwani J G, Topol E J. Aortocoronary saphenous vein graft disease: pathogenesis, predisposition, and prevention. Circulation. 1998 Mar. 10; 97(9):916-31.
6. Schwartz S M, deBlois D, O'Brien E R M. The Intima: Soil for Atherosclerosis and Restenosis. Circulation Research. 1995 Sep. 1; 77(3):445-65.
7. Abou Taum S, Garbé J-F, Boufi M, Bossavy J-P, Ricco J-B. Experimental study of a novel mechanical connector for sutureless open arterial anastomosis. Journal of vascular surgery. 2012 January; 55(1):210-5.
8. Disa J J, Cordeiro P G, Hidalgo D A. Efficacy of conventional monitoring techniques in free tissue transfer: an 11-year experience in 750 consecutive cases. Plastic and reconstructive surgery. 1999 July; 104(1):97-101.
9. Bui D T, Cordeiro P G, Hu Q-Y, Disa J J, Pusic A. Mehrara B J. Free flap reexplortion: indications, treatment, and outcomes in 1193 free flaps. Plastic and reconstructive surgery. 2007 June; 119(7):2092-100.
10. Beris A E, Lykissas M G, Korompilias A V, Mitsionis G I, Vekris M D, Kostas-Agantis I P. Digit and hand replantation. Archives of orthopaedic and trauma surgery. 2010 September; 130(9):1141-7.
11. Ameli F M, Provan J L, Williamson C, Keuchler P M. Etiology and management of aorto-femoral bypass graft failure. The Journal of cardiovascular surgery. 28(6):695-700.
12. Ojha M. Leask R L, Johnston K W. David T E, Butany J. Histology and morphology of 59 internal thoracic artery grafts and their distal anastomoses. The Annals of thoracic surgery. 2000 October; 70(4):1338-44.
13. Mary E. Charlson M D. O. Wayne Isom M D. Care after Coronary-Artery Bypass Surgery. The New England Journal of Medicine. 2003; 348:1456-63.
14. French B N. Rewcastle N B. Recurrent stenosis at site of carotid endarterectomy. Stroke. 1977; 8(5):597-605.
15. Zubilewiez T, Wronski J, Bourriez A, Terlecki P, Guinault A M, Muscatelli-Groux B, et al. Injury in vascular surgery—the intimal hyperplastic response. Medical science monitor. 2001; 7(2):316-24.
16. Pratt G, Rozen W, Westwood A, Hancock A, Chubb D, Ashton M W. et al. Technology-assisted and sutureless microvascular anastomoses: Evidence for current techniques. Microsurgery. 2012; 32(1):68-76.
17. Cho A B, Wei T H, Torres L R, Junior R M, Rugiero G M, Aita M A. Fibrin glue application in microvascular anastomosis: comparative study of two free flaps series. Microsurgery. 2009 January; 29(1):24-8.
18. Erdmann D, Sweis R, Heitmmmann C, Ysui K, Olbrich K C, Levin L S, at al. Side-to-side sutureless vascular anastomosis with magnets. Journal of vascular surgery. 2004 September; 40(3):505-11.
19. Wiklund L, Bonills L F, Berglin E. A new mechanical connector for distal coronary artery anastomoses in coronary artery bypass grafting: a randomized, controlled study. The Journal of thoracic and cardiovascular surgery. 2005 January; 129(1):146-50.
20. Liu L, Liu J, Zhu M, Hu S. Experimental study of one-shot vascular anastomostic device for proximal vein graft anastomoses. The Annals of thoracic surgery. 2006 July; 82(1):303-6.
21. Ueda K, Mukai T, Ichinose S, Koyama Y, Takakuda K, Bioabsorbable device for small-caliber vessel anastomosis. Microsurgery. 2010 September; 30(6):494-501.
22. Alghoul M S, Gordon C R, Yetman R, Buncke G M, Siemionow M, Afifi A M, et al. From simple interrupted to complex spiral: a systematic review of various suture techniques for microvascular anastomoses. Microsurgery. 2011 January; 31(1):72-80.
23. Ormiston J a, Serruys P W S. Bioabsorbable coronary stents. Circulation. Cardiovascular interventions. 2009 June; 2(3):255-60.
24. Erbel R, Di Mario C, Bartunek J, Bonnier J, De Bruyne B, Eberli F R, et al. Temporary scaffolding of coronary arteries with bioabsorbable magnesium stems: a prospective, non-randomised multicentre trial. Lancet. 2007 Jun. 2; 369(9576): 1869-75.
25. Camici G G. What is an optimal stent? Biological requirements of drug eluting stents. Kardiovaskulare Medizin. 2008; (11):22-5.
26. Nishio S, Kosuga K, Igaki K, Okada M, Kyo E. Long-Term (>10 Years) Clinical Outcomes of First-in-Human Biodegradable Poly-l-Lactic Acid Coronary StentaClinical Perspective Igaki-Tamai Stens. Circulation. 2012; 125(19):2343-53.
27. NIHR HSC. Bioresorbable stems for occlusive coronary artery disease. Birmingham: NIHR Horizon Scanning Centre (NIHR HSC). Horizon Scanning Review. 2012;
28. Gonzalo N, Macaya C. Absorbable stent focus on clinical applications and benefits. Vascular health and risk management. 2012 January; 8:125-32.
29. Van der Giessen W J, Lincoff a M, Schwartz R S, Van Beusekom H M. Serruys P W, Holmes D R, et al. Marked inflammatory sequelae to implantation of biodegradable and nonbiodegradable polymers in porcine coronary arteries. Circulation. 1996 Oct. 1; 94(7):1690-7.
30. Huang F, Sun L, Zheng J. In vitro and in vivo characterization of a silk fibroin-coated polyester vascular prosthesis. Artificial organs. 2008 December; 32(12):932-41.
31. Wang X, Zhang X, Castellot J, Herman I, Iafrati M, Kaplan D L. Controlled release from multilayer silk biomaterial coatings to modulate vascular cell responses. Biomaterials. 2008 March; 29(7):894-903.
32. Panilaitis B, Altman G H, Chen J, Jin H-J, Karageorgiou V, Kaplan D L. Macrophage responses to silk. Biomaterials. 2003 Aug.; 24(18):3079-85.
33. Lawrence B D, Wharram S, Kluge J a, Leisk G G, Omenetto F G, Rosenblatt M I, et al. Effect of hydration on silk film material properties. Macromolecular bioscience. 2010 Apr. 8; 10(4):393-403.
34. Rockwood D N, Preds R C, Yücel T, Wang X, Lovett M L, Kaplan D L, Materials fabrication from *Bombyx mori* silk fibroin. Nature protocols. 2011 October; 6(10):1612-31.
35. Meinel L, Hofmann S, Karageorgiou V, Kirker-Head C, McCool J, Gronowiez G, et al. The inflammatory responses to silk films in vitro and in vivo. Biomaterials. 2005 January; 26(2):147-55.
36. Altman G H, Diaz F, Jakuba C, Calabro T, Horan R L, Chen J, et al. Silk-based biomaterials. Biomaterials. 2003 February; 24(3):401-16.
37. Vepari C, Kaplan D L, Silk as a biomaterial. Progress in polymer science. 2007; 32(8-9):991-1007.
38. Murphy A R, John P S, Kaplan D L. Modification of silk fibroin using diazonium coupling chemistry and the effects on hMSC proliferation and differentiation. Biomaterials. 2008; 29(19):2829-38.
39. Murphy A R, Kaplan D L. Biomedical applications of chemically-modified silk fibroin. Journal of materials chemistry. 2009 Jun. 23; 19(36):6443-50.
40. Sofia S. McCarthy M B, Gronowiez G, Kaplan D L. Functionalized silk-based biomaterials for bone formation. Journal of biomedical materials research. 2001 January; 54(1):139-48.
41. Ziberman M, Nelson K D, Eberhart R C, Mechanical properties and in vitro degradation of bioresorbable fibers and expendable fiber-based stents. Journal of biomedical materials research. Part B, Applied biomaterials. 2005 August; 74(2):792-9.
42. Ramcharitar S, Searuys P W. Fully biodegradable coronary stems: progress to date. American journal of cardiovascular drugs: drugs, devices, and other interventions. 2008 January; 8(5):305-14.

43. Pritchard E M, Szybala C, Boison D, Kaplan D L. Silk fibroin encapsulated powder reservoirs for sustained release of adenosine. Journal of controlled release: official journal of the Controlled Release Society. 2010 Jun. 1; 144(2):159-67.
44. Lu S, Wang X, Lu Q, Hu X, Uppal N, Omenetto F G, et al. Stabilization of enzymes in silk films. Biomacromolecules. 2009 May 11; 10(5):1032-42.
45. Lu Q, Wang X, Hu X, Cebe P, Omenetto F G, Kaplan D L. Stabilization and release of enzymes from silk finms. Macromolecular bioscience. 2010 Apr. 8; 10(4):359-68.
46. Zhang W, Wang X, Wang S, Zhao J, Xu L, Zhu C, at al. The use of injectable sonication-induced silk hydrogel for VEGF(165) and BMP-2 delivery for elevation of the maxillary sinus floor. Biomaterials. 2011 December; 32(35):9415-24.
47. Saitow C, Kaplan D L, Castellot J J. Heparin stimulates elastogenesis: application to silk-based vascular grafts. Matrix biology: journal of the International Society for Matrix Biology. 2011 June; 30(5-6):346-55.
48. Wang X, Wenk E, Zhang X, Meinel L, Vunjak-Novakovic G, Kaplan D L. Growth factor gradients via microsphere delivery in biopolymer scaffolds for osteochondral tissue engineering. Journal of controlled release: official journal of the Controlled Release Society. 2009 Mar. 4; 134(2):81-90.
49. Wang X, Week E, Matsumoto A, Meinel L, Li C, Kaplan D L. Silk microspheres for encapsulation and controlled release. Journal of controlled release: official journal of the Controlled Release Society. 2007 Feb. 26; 117(3):360-70.

What is claimed is:

1. An anastomosis device for promoting vascular healing comprising:
a hollow tube that extends along a longitudinal axis from a first end to a second end,
the hollow tube comprising a blend that comprises silk fibroin and a plasticizer that is programmably biodegradable and/or resorbable, the hollow tube having a compressive strength within a range of 1 MPa to 10 MPa,
wherein an outside diameter of the hollow tube at its first and second ends is larger than an inside diameter of a human blood vessel and wherein when the blend is exposed to physiological conditions the hollow tube swells, such that when the device is implanted to at least one end of the human blood vessel, the device provides securing or sealing to fluid flow.

2. The anastomosis device according to claim 1, further comprising at least one non-piercing suture adapted to be wrapped around the at least one end of the human blood vessel to secure it to the hollow tube.

3. The anastomosis device according to claim 1, wherein at least one the ends of the hollow tube further comprises a spherical enlarged portion.

4. The anastomosis device according to claim 1, wherein the first end of the hollow tube includes at least one barb extending substantially transverse to the longitudinal axis of the hollow tube and adapted to penetrate at least a portion of the human blood vessel; and the device further comprising a first sleeve adapted to fit over the human blood vessel when the human blood vessel is fitted over the first end of the hollow tube and penetrated by the at least one barb to capture the human blood vessel between the first end and the first sleeve.

5. The anastomosis device according to claim 1, wherein the blend further comprises an additive.

6. The anastomosis device according to claim 1, wherein the hollow tube is or comprises a cylindrical body portion that is a multilayered cylindrical body portion.

7. The anastomosis device according to claim 1, wherein the hollow tube is or comprises a cylindrical body portion that has an average mechanical stiffness of 1.2 kN/m.

8. The anastomosis device according to claim 1, wherein the hollow tube is or comprises a cylindrical body portion that has an average radial strength of 300 mmHg.

9. The anastomosis device according to claim 1, wherein the blend comprises micropores.

10. The anastomosis device according to claim 1, wherein the blend further comprises an active agent.

11. The anastomosis device according to claim 1, wherein the blend further comprises an anti-restenosis agent.

12. A method comprising:
implanting the anastomosis device of claim 1 at a target site in a subject.

13. The method of claim 12, wherein the hollow tube based blend material swells upon implantation at the target site, thereby reducing anastomosis device malapposition post-implantation.

14. The method of claim 12, wherein the anastomosis device degrades as a tissue surrounding the target site remodels or regenerates.

15. A cell scaffold comprising the anastomosis device of claim 1, wherein the plasticizer is glycerol and the blend further comprises a cell.

16. A method for joining a first human blood vessel to a second human blood vessel, the method comprising steps of:
providing the anastomosis device of claim 1;
inserting the first end of the hollow tube into a terminal end of a first human blood vessel and the second end of the hollow tube into a terminal end of a second human blood vessel.

17. The method according to claim 16, further comprising wrapping a non-piercing suture around at least one of the first human blood vessel and the second human blood vessel to secure at least one of the first human blood vessel and the second human blood vessel to the hollow tube.

18. The method according to claim 16, further comprising a step of positioning an outer sleeve over the first end of the hollow tube after the first end of the hollow tube has been inserted into the terminal end of the first human blood vessel to capture the first human blood vessel between an outside diameter of the first end of the hollow tube and an inside diameter of the outer sleeve.

19. The anastomosis device according to claim 1, wherein at least one of the first end and the second end is beveled.

20. The anastomosis device according to claim 1, wherein an outer surface of at least one of the ends of the hollow tube further comprises threads, wherein the device further comprises at least one spherical enlarged portion having threads adapted to receive the threads from the at least one of the ends of the hollow tube, and wherein when the spherical enlarged portion is inserted into the end of the human blood vessel it is configured to be screwed onto threading of the spherical enlarged portion.

* * * * *